(12) United States Patent
Vilaboa et al.

(10) Patent No.: US 11,597,708 B2
(45) Date of Patent: Mar. 7, 2023

(54) INHIBITORS OF HEAT SHOCK FACTORS AND USES THEREOF

(71) Applicant: HSF Pharmaceuticals SA, La Tour-de-Peilz (CH)

(72) Inventors: Nuria Vilaboa, Madrid (ES); Richard W Voellmy, La Tour-de-Peilz (CH)

(73) Assignee: HSF PHARMACEUTICALS SA, Tour-de-Peilz (CH)

( * ) Notice: Subject to any disclaimer, the term of this patent is extended or adjusted under 35 U.S.C. 154(b) by 552 days.

(21) Appl. No.: 16/501,272

(22) PCT Filed: Sep. 12, 2017

(86) PCT No.: PCT/EP2017/072930
§ 371 (c)(1),
(2) Date: Mar. 14, 2019

(87) PCT Pub. No.: WO2018/050656
PCT Pub. Date: Mar. 22, 2018

(65) Prior Publication Data
US 2021/0221778 A1    Jul. 22, 2021

Related U.S. Application Data

(60) Provisional application No. 62/495,501, filed on Sep. 16, 2016, provisional application No. 62/499,650, filed on Feb. 2, 2017.

(51) Int. Cl.

| | |
|---|---|
| *C07D 277/46* | (2006.01) |
| *A61P 35/00* | (2006.01) |
| *C07D 213/75* | (2006.01) |
| *C07D 215/42* | (2006.01) |
| *C07D 231/40* | (2006.01) |
| *C07D 261/14* | (2006.01) |
| *C07D 263/48* | (2006.01) |
| *C07D 277/56* | (2006.01) |
| *C07D 277/82* | (2006.01) |
| *C07D 285/135* | (2006.01) |
| *C07D 333/36* | (2006.01) |
| *C07D 417/04* | (2006.01) |
| *C07D 417/12* | (2006.01) |
| *C07D 417/14* | (2006.01) |

(52) U.S. Cl.
CPC ............ *C07D 277/46* (2013.01); *A61P 35/00* (2018.01); *C07D 213/75* (2013.01); *C07D 215/42* (2013.01); *C07D 231/40* (2013.01); *C07D 261/14* (2013.01); *C07D 263/48* (2013.01); *C07D 277/56* (2013.01); *C07D 277/82* (2013.01); *C07D 285/135* (2013.01); *C07D 333/36* (2013.01); *C07D 417/04* (2013.01); *C07D 417/12* (2013.01); *C07D 417/14* (2013.01)

(58) Field of Classification Search
CPC ............................... C07D 277/46; A61P 35/00
See application file for complete search history.

(56) References Cited

U.S. PATENT DOCUMENTS 3,919,201 A * 11/1975 Evans .................. C07D 513/04
546/198
2019/0055232 A1    2/2019 Gibson et al.

FOREIGN PATENT DOCUMENTS

| WO | WO 01/97786 | 12/2001 |
|---|---|---|
| WO | WO 2005/105777 | 11/2005 |

OTHER PUBLICATIONS

Evans, Delme (1974) : STN International CAPLUS database, (Columbus, Ohio), Accession No. 1974: 133418.*
Vilaboa et al. (2017) New inhibitor targeting human transcription factor HSF1: effects on the heat shock response and tumor cell survivial. Nucl. Acids Res. 45: 5797-5817.
Wensbo et al. (1995) Indol-3-acetic acids and hetero analogs by one-pot synthesis including Heck cyclization. Tetrahedron 51: 10323-10342.
Kabachnyi et al. (1985) Production of surface-active agents with pronunced pharmacological activity. Pharmaceutical Chemistry J. 19: 33-35.
Islip et al. (1973) Antiparasitic 5-nitrothiazoles and 5-nitro-4-thiazolines. J. Med. Chem. 16: 1030-1034.

* cited by examiner

*Primary Examiner* — Golam M Shameem
(74) *Attorney, Agent, or Firm* — Richard Voellmy

(57) ABSTRACT

The present disclosure relates to a class of mammalian heat shock factor (HSF) inhibitors, to pharmaceutical compositions comprising these inhibitors as well as to methods for using the inhibitors. The inhibitors inhibit stress-induced expression from heat shock gene promoters. Furthermore, the inhibitors are cytotoxic to a variety of human cancer cells types.

7 Claims, 9 Drawing Sheets
Specification includes a Sequence Listing.

INHIBITORS OF HEAT SHOCK FACTORS AND USES THEREOF

TECHNICAL FIELD

The present disclosure relates to heat shock factor inhibitors and uses thereof in the treatment of diseases and other conditions that depend on or are enhanced by heat shock factor activity.

BACKGROUND OF THE INVENTION

Heat shock genes were discovered more than 50 years ago as genes whose activity is increased in cells exposed to elevated temperature (often about 5° C. above normal). Ritossa, F. (1962) Cellular and Molecular Life Sciences 18: 571-573. Protein products of these genes, heat shock proteins (HSP), were identified some ten years later. Because their functions were unknown at the time, HSPs were classified according to their subunit molecular weights (in kDa) and have been referred to as HSP90, HSP70, HSP60, etc. Further investigation of heat-inducible genes and proteins revealed that the group also included genes encoding proteins with previously known functions such as heme oxidase, ubiquitin, FKBP52, MDR1, LDH-A, etc. It also was found that there existed homologous genes encoding proteins (HSC) highly related to HSPs, the activity of which genes did not increase in response to heat. As more was learned about the functions of HSPs, the latter finding began to make sense: many HSPs act as molecular chaperones and play important roles in normal protein homeostasis (proteostasis) and trafficking. Hence, an unheated cell maintains substantial levels of HSCs and HSPs. When it is heated, it activates, or enhances the activity of, inducible heat shock genes (hsp genes) resulting in elevated levels of HSPs. The latter reaction is referred to as the heat shock protein response. Because not only heat treatment but also exposure to a wide range of noxious chemicals activates inducible hsp genes, the terms "stress protein genes", "stress proteins" and "stress protein response" are used frequently in lieu of "heat shock protein genes", "heat shock proteins" and "heat shock protein response".

Exposure of cells to above-normal temperatures (heat stress) or chemical stress leads to a degradation of protein quality control and can result in activation of apoptotic mechanisms. Elevated levels of HSPs resulting from forced over-expression or a mild stress exposure (stress pre-conditioning) inhibit apoptotic mechanisms and counteract degradation of protein quality control. Stress pre-conditioning has been shown to produce a transient tolerance that permits cells to weather severe stress conditions that would normally be lethal. Over-expression of HSPs was found to produce "therapeutic" effects in various disease models, e.g., in models of ischemia of the heart or the brain, or neurodegenerative conditions such as Parkinson's and polyglutamine diseases. It is noted that Alzheimer's, Parkinson's and all ataxias are considered to be diseases of protein folding. It is therefore not surprising that provision of extra HSPs, i.e., of extra chaperoning capacity, can be an effective means for attenuating or preventing these diseases. Akerfelt, M., Morimoto, R. I. and Sistonen, L. (2010) Nat. Rev. Mol. Cell Biol. 11: 545-555; Parsell, D. A. and Lindquist, S. 1993. Annu. Rev. Genet. 27: 437-496.

Expression of genes is mediated by so-called promoters, which are gene-associated sequence regions capable of interacting with transcription factors and components of the transcription machinery. Stress induction of hsp genes is conferred by so-called HSE sequences present within the promoters of these genes (hsp promoters). HSEs are binding sites for heat shock factors (also referred to as heat shock transcription factors) (HSF), in particular HSF1. HSF1 is a ubiquitously expressed transcription factor that is normally present in an inactive form but is reversibly activated when a cell experiences a heat or chemical stress. Vertebrate cells typically also express one or more other HSF, e.g., HSF2, HSF3 (avian) or HSF4. Akerfelt, M., Morimoto, R. I. and Sistonen, L. (2010) Nat. Rev. Mol. Cell Biol. 11: 545-555; Voellmy, R., and Boellmann, F. (2007) Adv. Exp. Med. Biol. 594: 89-99.

HSFs, including HSF1, are not essential for the normal life of a mammalian cell or even a mammalian organism, although mice lacking HSF1, HSF2 or HSF4 show important phenotypes. Jin, X. et al. (2011) Meth. Mol. Biol. 787: 1-20. Mammalian cells or organisms not expressing HSF1 are incapable of induced HSP expression as well as have an elevated sensitivity to stress. McMillan, D. R. et al. (1998) J. Biol. Chem. 273: 7523-7528; Xiao, X. et al. (1999) EMBO J. 18: 5943-5952; Christians, E. S. and Benjamin, I. J. (2006) Handb. Exp. Pharmacol. 172: 139-152.

Work carried out over the last ten plus years qualified HSF1 as a new and promising target for cancer therapy. HSF1 was shown to be critically important for effective tumorigenesis in several different animal tumor models. HSF1 was also found to play an essential role in the maintenance (viability) of a variety of different human tumor cell lines, including breast (of different p53 status, HER2 over-expression, estrogen sensitivity and metastatic potential), cervical, prostate, nerve sheath and kidney cancer lines and melanoma. Dai, C. et al. (2007) Cell 130: 1005-1018; Khaleque, M. et al. (2005) Oncogene 24: 6564-6573; Meng, L. et al. (2010) Oncogene 29: 5204-13; Nakamura, Y. et al. (2010) J. Dermatol. Sci. 60: 187-192; Solimini, N. et al. (2007) Cell 130: 986-988; Whitesell, L. and Lindquist, S. (2009). Expert Opin. Ther. Targets 13: 469-478; Zhao, Y. et al. (2009) Oncogene 28: 3689-3701. More recently, HSF1 was shown to regulate a transcriptional program specific to highly malignant cells, which program differs from that triggered by heat stress. Mendillo, M. L. et al. (2012) Cell 150: 549-562.

To the extent that this is known to date, HSF1 activity is controlled by interactions with a number of other proteins and the activities of modifying enzymes (protein kinases, etc.). Of the known proteins or enzymes affecting HSF1 activity, none is specific to HSF1. Targeting any one of the latter proteins or enzymes with an intention to also inhibit HSF1 activity is expected to have pleiotropic effects that are likely manifested in excessive general toxicity of inhibitor compounds. Hence, the most desirable anti-cancer agents that act by inhibiting HSF1 activity would be compounds that directly and specifically interact with the transcription factor. Whitesell, L. and Lindquist, S. (2009); Voellmy, R. (2006) Handb. Exp. Pharmacol. 172: 43-68. The present disclosure relates to the discovery of HSF inhibitors and their uses, e.g., as anti-cancer agents.

SUMMARY OF THE INVENTION

An inhibitor of HSF (also referred to herein as HSF inhibitor, inhibitor of HSF or $I_{HSF}$) is defined herein as a small molecule compound that is capable of inhibiting the prototypical function of a mammalian, especially human, HSF1, which function is to mediate stress-induced (e.g., heat-induced) expression (i.e., transient accumulation transcripts and/or protein products) of genes that are functionally linked to stress-inducible promoters (i.e., HSE-containing promoters). The latter genes are also referred to as HSF target genes. (They are target genes of multiple HSF, since HSF1, 2 and 4 are generally capable of binding HSE sequences). The term "small molecule" shall have the specific meaning defined in this specification.

In one embodiment, the HSF inhibitor is further defined as a small molecule that inhibits the transcription-enhancing activity of a mammalian (or, more particularly, human) HSF1 but not of a (not naturally occurring) chimeric mammalian HSF1 containing a heterologous DNA-binding domain. Hence, the HSF inhibitor interacts with the HSF DNA-binding domain to exert its effect on the prototypic HSF function.

In a more particular embodiment, the HSF inhibitor is further characterized as a small molecule that binds to the DNA-binding domain of a mammalian, in particular human, HSF1. This binding is direct, i.e., it is to a feature of the surface of the HSF1 DNA-binding domain, but not to a protein or other molecule that associates with the latter HSF domain. As is explained below, the HSF inhibitor may also be capable of binding the DNA-binding domain of other mammalian HSF.

In another embodiment, the HSF inhibitor is further characterized as a small molecule that fits pharmacophore A4 which was established based on relevant features of predicted cavity A of the DNA-binding domain of human HSF1 using methods well known in the art. Cavity A of human HSF1 is defined by amino acid residues Val70, Leu73, Asn74, Phe78, Arg79, Lys80, Thr97, Glu98 and Phe99, with reference to the amino acid sequence of HSF1 shown in UniProtKB-Q00613 (HSF1_HUMAN), also listed in SEQ ID NO: 1. It is noted that cavity A can be readily identified in other mammalian HSF, given the high degree of sequence conservation among mammalian HSF. Recent structural information on human HSF1, the crystal structures 5D5U and 5D5V and the NMR structure 2LDU, and on human HSF2, the crystal structures 5D8K and 5D8L, indicate that a cavity resembling the predicted cavity A is present in both HSF1 and HSF2, although shapes differ slightly. However, the NMR structure of 2LDU has 20 different solutions that adhere to the NMR data, showing the residues which line the cavity can be modelled in different positions. Given that a number of protein conformations can be generated that satisfy the NMR data, more conformations are potentially available and predicted cavity A represents a feasible conformation. Based on the similarities between the crystal structures for HSF1 and HSF2, it may be expected that HSF inhibitors that satisfy the constraints of pharmacophore A4 are not only inhibitors of HSF1 but also of other HSF, in particular, mammalian, including human, HSF2.

The 3-point pharmacophore A4 is defined by a first hydrogen bond acceptor point, a second hydrogen bond acceptor point and a lipophilic point, whereby the distance between first and second hydrogen bond acceptor points is 9.495 Å (angstrom), the distance between the first hydrogen bond acceptor point and the lipophilic point is 7.992 Å and the distance between the second hydrogen bond acceptor point and the lipophilic point is 5.153 Å. The radius around each pharmacophoric point was set to 2.0 Å ("inclusion sphere"), meaning that a small molecule must have an appropriate feature within the inclusion sphere of each pharmacophoric point to be regarded as an inhibitor of HSF of this particular embodiment. A preferred inhibitor of HSF of this particular embodiment has an overall "FitValue" score of at least 1.0. If a relevant feature of a small molecule hits the center of the inclusion sphere around a pharmacophoric point exactly, it receives a FitValue of 1.0. FitValues decrease from 1.0 to 0 from the center to the periphery of an inclusion sphere. The maximal overall FitValue score is 3.0 (1.0 for each pharmacophoric point). Inhibitors of HSF of this particular embodiment are referred to as (having been) designed to bind to cavity A of a mammalian HSF.

In another particular embodiment, the HSF inhibitor is further characterized as a small molecule that exerts its inhibitory effect on prototypical HSF function, e.g., on induced hsp gene expression in the case of HSF1, without affecting the DNA-binding ability of the HSF. In another particular embodiment, the HSF inhibitor is further characterized as a small molecule that, although designed to bind to the DNA-binding domain of a mammalian HSF, in particular a human HSF, exerts its inhibitory effect on prototypical HSF function, e.g., on induced hsp gene expression in the case of HSF1, without affecting the DNA-binding ability of the HSF. Hence, the inhibitor does not inhibit the DNA-binding activity of the HSF but some other aspect relevant to HSF function that somehow involves or can be influenced by the HSF DNA-binding domain. In a further particular embodiment, the inhibitor of HSF is further characterized as a small molecule that interferes with the assembly of transcription complexes on HSF target genes in a mammalian cell.

In another embodiment, the inhibitor of HSF is an acrylamide derivative of formulae (II), (V), (IX) or (X). More specific embodiments of inhibitors of formula (II) are described by formulae (IV), (VI) and (VIII). More specific embodiments of inhibitors of formula (V) are described by formula (VII). More specific embodiments of inhibitors of formula (IX) are described by formula (XI), and of inhibitors of formula (X) by formula (XII).

Some or all of the latter characteristics may be combined in an inhibitor of HSF of the present disclosure, i.e., it may be characterized as a small molecule that interacts with an HSF DNA-binding domain, does not interfere with the binding of the inhibited HSF to its target genes, binds, and/or has been designed to bind, in cavity A, interferes with the assembly of transcription complexes on HSF target genes, is capable of binding to the DNA-binding domain of mammalian or human HSF1 and, expectedly, other HSF, and/or is an acrylamide derivative of formulae (II), (V), (IX) or (X).

Therefore, an inhibitor of HSF of the present disclosure can be, in the alternative, a compound of formula II

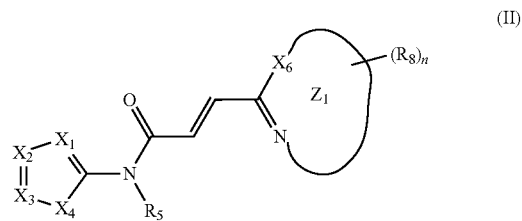

or a salt thereof, wherein n is 0-8, preferably 0-4 (0, 1, 2, 3 or 4);

$X_1$ is N or C(—$R_1$);

$X_2$ is C(—$R_2$), N, or S or O (double bond between $X_3$ and $X_4$ instead of between $X_2$ and $X_3$);

$X_3$ is C(—$R_3$) or N;

$X_4$ is S or O, or C(—$R_4$) or N if $X_2$ is O or S (double bond between $X_3$ and $X_4$ instead of between $X_2$ and $X_3$);

$X_6$ is O, S, N, NH, ($C_1$-$C_4$)alkylN, CH or C((($C_1$-$C_4$)alkyl), $CH_2$ or CH((($C_1$-$C_4$)alkyl);

R₁ is H, halo, (C₁-C₄)alkyl; halo(C₁-C₄)alkyl, H being preferred;

R₂, R₃, R₅ and R₈ are independently selected, and each can be H or any substituent, provided that its presence is compatible with the small molecule nature of the inhibitor and, statistically, no more than 10% of any ionizable group it may contain is ionized at neutral pH;

whereby R₂ and R₃ can form a substituted or unsubstituted 5 to 8 membered aromatic or non-aromatic ring or heterocycle including X₂ and X₃:

R₄ is H, halo, (C₁-C₄)alkyl; halo(C₁-C₄)alkyl, H being preferred;

and Z₁ is a 5-8 membered, non-aromatic heterocycle.

In alternative embodiments, substituents R₂, R₃, R₅ and R₈ in formula II (or in any of formulae I, III XII in which one or more of these substituents are indicated) are independently selected from the group consisting of H, hydroxy, formyl, alkylcarbonyl, alkoxy, alkylthio, alkylthioalkyl, alkoxyalkoxy, alkoxycarbonyl, alkoxyalkenyl, alkoxyalkynyl, alkoxycarbonylalkoxy, alkyl, alkenyl, alkenyloxy, alkenylthio, alkynyl, alkynylthio, cycloalkyl, cycloalkylthio, cycloalkylalkoxy, cycloalkylalkylthio, cycloalkenylalkoxy, cycloalkenylalkylthio, alkylSO₂—, acryl, arylalkyl, aryloxy, arylthio, arylalkenyl, arylalkynyl, arylcarbonyl, arylalkoxycarbonyl, heteroaryl, heterocycle, heterocyclealkyl, heterocyclealkenyl, heterocyclealkoxy, heterocyclealkylthio, heterocyclealkynyl, heterocyclecarbonyl, heterocycleoxycarbonyl, cyano, cyanoalkyl, cyanoalkoxy, cyanoalkylthio, cyanoalkynyl, cyanoalkenyl, cyanoalkenylalkoxy, cyanoalkenylalkylthio, halogen, haloalkyl, trihaloalkyl, trihaloalkoxy, hydroxyalkyl, hydroxyalkenyl, hydroxyalkynyl, hydroxyalkoxy, hydroxyalkylthio, dihydoxyalkoxy, dihydoxyalkylthio, nitro, R_f—O—, R_f—S—, HO—N=CH—(CH2)_{0, 1 or 2}-, R_aR_bN—, R_aR_bNalkyl-, R_aR_bNalkenyl-, R_aR_bNalkynyl-, R_aR_bNC(O)—, R_aR_bNC(O)alkynyl-, R_aR_bNC(O)alkoxy-, R_aR_bNSO₂alkoxy-, and R_w—O—N=CH—, wherein alkyl may be optionally substituted with O= and R_tN=; R_a and R_b are each individually selected from the group consisting of hydrogen, alkyl, alkenyl, alkenylcarbonyl, alkylsulfonyl, alkylcarbonyl, alkoxycarbonyl, alkoxycarbonylalkyl, alkoxycarbonylalkylcarbonyl, alkynyl, aryl, arylalkyl, arylalkenyl, arylcarbonyl, aryloxycarbonyl, arylalkyloxycarbonyl, heteroaryl, heterocycle, heterocyclealkyl, heterocyclealkenyl, heterocyclecarbonyl, heterocyclealkylcarbonyl, haloalkyl, trihaloalkyl, trihaloalkylcarbonyl, haloalkylcarbonyl, heterocycleoxycarbonyl hydroxyalkyl, and hydroxyalkylcarbonyl; R_t is selected from the group consisting of hydrogen, alkyl and HO—; R_f is selected from the group consisting of alkyl, cycloalkyl, cycloalkylalkyl, alkoxyalkyl, alkylthioalkyl, and haloalkyl; R_w is selected from the group consisting of hydrogen, alkylcarbonyl-NH-alkyl-NHC(O)-alkyl, alkyl, alkyl(alkyl)N-alkyl-NHC(O)-alkyl, hydroxyalkyl-NHC(O)-alkyl, heterocyclealkyl-NHC(O)-alkyl, heterocycle-NHC(O)-alkyl, and heteroarylalkyl-NHC(O)-alkyl.

In further alternative embodiments, substituents R₂, R₃, R₅ and R₈ in formula II (or in any of formulae I, III XII in which one or more of these substituents are indicated) are independently selected from the group consisting of H, hydroxy, formyl, alkylcarbonyl, alkoxy, alkylthio, alkylthioalkyl, alkoxyalkoxy, alkoxycarbonyl, alkoxyalkenyl, alkoxyalkynyl, alkoxycarbonylalkoxy, alkyl, alkenyl, alkenyloxy, alkynyl, cycloalkyl, cycloalkylalkoxy, cycloalkenylalkoxy, alkylSO₂—, acryl, arylalkyl, aryloxy, arylalkenyl, arylalkynyl, arylcarbonyl, arylalkoxycarbonyl, heteroaryl, heterocycle, heterocyclealkyl, heterocyclealkenyl, heterocyclealkoxy, heterocycle alkynyl, heterocyclecarbonyl, heterocycleoxycarbonyl, cyano, cyano alkyl, cyanoalkoxy, cyanoalkylthio, cyanoalkynyl, cyanoalkenyl, cyanoalkenylalkoxy, halogen, haloalkyl, trihaloalkyl, trihaloalkoxy, hydroxyalkyl, hydroxyalkenyl, hydroxyalkynyl, hydroxyalkoxy, dihydoxyalkoxy, nitro, R_f—O—, HO—N=CH—(CH2)_{0, 1 or 2}-, R_aR_bN—, R_aR_bNalkyl-, R_aR_bNalkenyl-, R_aR_bNalkynyl-, R_aR_bNC(O)—, R_aR_bNC(O)alkynyl-, R_aR_bNC(O)alkoxy-, R_aR_bNSO₂alkoxy-, and R_w—O—N=CH—, wherein alkyl may be optionally substituted with O= and R_tN=; R_a and R_b are each individually selected from the group consisting of hydrogen, alkyl, alkenyl, alkenylcarbonyl, alkylsulfonyl, alkylcarbonyl, alkoxycarbonyl, alkoxycarbonylalkyl, alkoxycarbonylalkylcarbonyl, alkynyl, aryl, arylalkyl, arylalkenyl, arylcarbonyl, aryloxycarbonyl, arylalkyloxycarbonyl, heteroaryl, heterocycle, heterocyclealkyl, heterocyclealkenyl, heterocyclecarbonyl, heterocyclealkylcarbonyl, haloalkyl, trihaloalkyl, trihaloalkylcarbonyl, haloalkylcarbonyl, heterocycleoxycarbonyl hydroxyalkyl, and hydroxyalkylcarbonyl; R_t is selected from the group consisting of hydrogen, alkyl and HO—; R_f is selected from the group consisting of alkyl, cycloalkyl, cycloalkylalkyl, alkoxyalkyl, alkylthioalkyl, and haloalkyl; R, is selected from the group consisting of hydrogen, alkylcarbonyl-NH-alkyl-NHC(O)-alkyl, alkyl, alkyl(alkyl)N-alkyl-NHC(O)-alkyl, hydroxyalkylNHC(O)-alkyl, heterocyclealkyl-NHC(O)-alkyl, heterocycle-NHC(O)-alkyl, and heteroarylalkylNHC(O)-alkyl.

More specifically, an inhibitor of HSF can be, in the alternative, a compound of formula IV or a salt thereof, whereby R₂, R₃, R₅, R₈, X₆ and Z₁ are as defined before for the inhibitors of formula II.

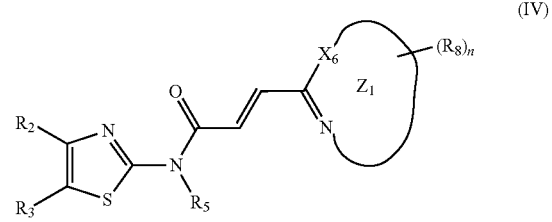

(IV)

An inhibitor of HSF can be, in the alternative, a compound of formula V or formula VI or a salt thereof, whereby n, R₂, R₅, R₈, X₆ and Z1 are as defined before; X₅ is O, S or N(—R₆); R₆ is H or is selected from halogen, OH, SH, NH₂ and Z₂ whereby Z₂ is a residue comprising from 1 to 4 carbon atoms; R₇ is —OH, —SH, —NH₂, —O—Z₂, —S—Z₂, —NH—Z₂ or —N—(Z₂)₂; X₇ is CH or N (preferably, 3 or less of the X₇ being N, and most preferably only one of the X₇ being N); R₁₀ is defined as R₅; and s is 0, 1, 2, 3 or 4.

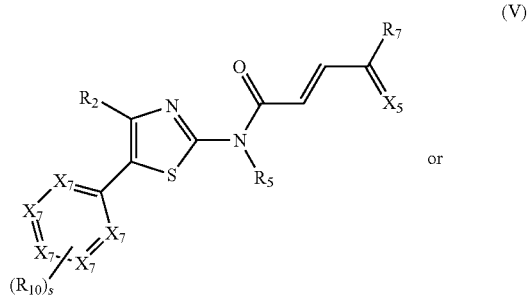

(V)

or

-continued (VI)

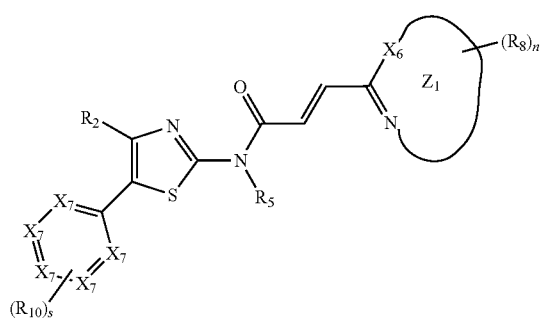

More specifically, an inhibitor of HSF can be, in the alternative, a compound of formula VII or formula VIII or a salt thereof, whereby n, s, $R_2$, $R_5$, $R_6$, $R_7$, $R_8$, $R_{10}$, $X_5$, $X_6$, $X_7$ and $Z_1$ are as defined before.

(VII)

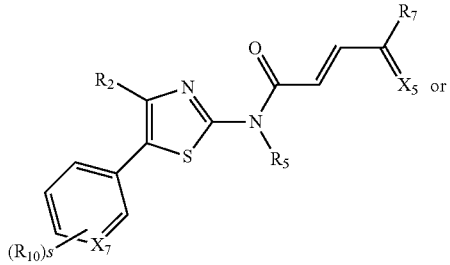

(VIII)

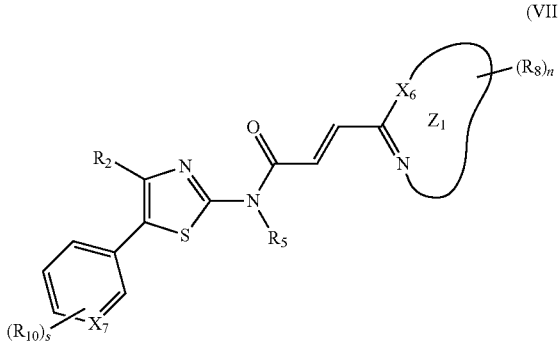

An inhibitor of HSF can be (E)-3-(5,6-dihydro-4H-[1,3]oxazin-2-yl)-N-methyl-N-(5-(pyridin-3-yl-thiazol-2-yl)acrylamide or a salt thereof.

An inhibitor of HSF can be, in the alternative, a compound of formula IX or formula X or a salt thereof, whereby n, $R_5$, $R_6$, $R_7$, $R_8$, $X_5$, $X_6$ and $Z_1$ are as defined before; r is 0-4 and $R_{11}$ is defined as $R_5$; with the proviso that, if r is 0, $R_5$, $R_7$ and $X_5$ cannot be simultaneously H, methoxy and O, respectively.

(IX)

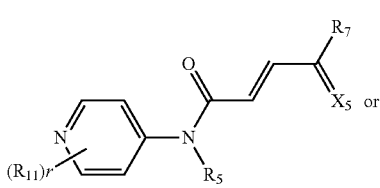

(X)

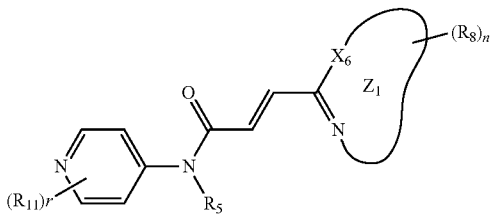

More specifically, an inhibitor of HSF can be, in the alternative, a compound of formula XI or formula XII or a salt thereof, whereby n, $R_5$, $R_6$, $R_7$, $R_8$, $X_5$, $X_6$ and $Z_1$, are as previously defined; o is 0-4; $R_{12}$ and $R_{13}$ are as $R_5$ and $X_8$ is CH or N. Preferably, 3 or less of the $X_8$ are N, and most preferably only one $X_8$ is N.

(XI)

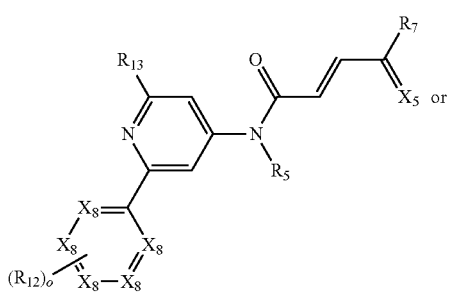

(XII)

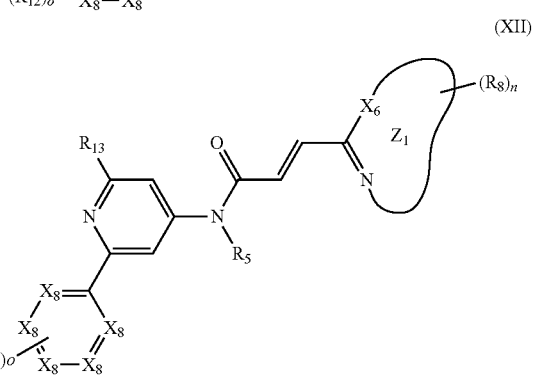

The present disclosure also relates to a pharmaceutical composition for treatment or prophylaxis in a mammalian (in particular a human) subject or for use in the treatment or prophylaxis of a disease or condition that is mediated or enhanced by the activity of an HSF, in particular an HSF1, the composition comprising an effective amount of an inhibitor of the mammalian (in particular human) HSF or a pharmaceutically acceptable salt or prodrug thereof. In a particular embodiment, the inhibitor of the mammalian (in particular human) HSF is a small molecule that interacts with the DNA-binding domain of the HSF and/or binds the DNA-binding domain of the HSF. In another particular embodiment, the inhibitor of HSF is a small molecule that mediates its inhibitory effect on the function of the HSF without inhibiting the binding of the HSF to its target genes. In yet another particular embodiment, the inhibitor of the mammalian (in particular human) HSF is a small molecule that binds and/or has been/is designed to bind in cavity A of the DNA-binding domain of the mammalian HSF. In a further particular embodiment, the inhibitor of the mammalian (in particular human) HSF is a small molecule that interferes with the assembly of transcription complexes on HSF target genes. The inhibitor of the HSF can be an acrylamide derivative of formula (I), (II), (IX) or (X). More particularly, the inhibitor of the HSF can be an acrylamide derivative of formula (II), (V), (IX) or (X). Some or all of the latter particular characteristics (also referred to as "properties") may be combined in the inhibitor of the HSF.

The disease treated can be a hyperproliferative disease. The hyperproliferative disease can be a cancer, or more specifically, a cancer selected from the group consisting of a cervical cancer, a breast cancer, a lung cancer, a prostate cancer, an ovarian cancer, a neuroblastoma, a peripheral nerve sheath cancer, a leukemia, a myeloma, a liver cancer and an osteosarcoma.

In another embodiment, the present disclosure relates to a method for inhibiting or reducing the function of an HSF, in particular HSF1, in a mammalian cell, preferably a human cell, comprising exposing the cell to an effective concentration of an inhibitor of the HSF, which inhibitor is characterized below. The mammalian cell can be a cell in culture or a cell of a mammalian organism. As mentioned before, in the case of HSF1, the term "function of an HSF" typically refers to the ability of HSF1 to mediate the induced expression of genes that are functionally linked to inducible, HSE-containing promoters, and the term "effective concentration" refers to a concentration that detectably reduces the induced expression of at least one such gene, whereby expression can be measured either at the transcript or the protein product level.

In a further embodiment, the disclosure relates to a method for reducing the viability of a mammalian, in particular a human, hyperproliferative cell, preferably a cancer cell, comprising exposing the cell to an effective concentration of an HSF inhibitor, which inhibitor is characterized below. An effective concentration is a concentration that detectably reduces the viability of the mammalian hyperproliferative cell as measured by a suitable assay. The hyperproliferative cell being exposed to the HSF inhibitor can be a cultured cell or a cell that is resident in a mammalian, in particular a human, subject, i.e., in a cancer of the subject. The cancer cell can be a cell of any cancer or, more specifically, of a cervical cancer, a breast cancer, a lung cancer, a prostate cancer, an ovarian cancer, a neuroblastoma, a peripheral nerve sheath cancer, a leukemia, a myeloma, a liver cancer or an osteosarcoma. More generally, the disclosure relates to a method for the prevention or treatment of a disease or condition mediated or enhanced by an HSF, the method comprising administering to a subject in need thereof an effective amount of an HSF inhibitor, which inhibitor is characterized below. Cancers are among the latter diseases. In the latter method, the HSF that enhances or mediates the disease or condition can be an HSF1.

In another embodiment, the disclosure relates to the use of an HSF inhibitor as characterized below in the treatment or prophylaxis in a mammalian subject, particularly a human subject, of a disease or condition that is mediated or enhanced by the activity of an HSF. The HSF that enhances or mediates the disease or condition can be an HSF1. The disease can be a hyperproliferative disease. The hyperproliferative disease can be a cancer, in particular a cervical cancer, a breast cancer, a lung cancer, a prostate cancer, an ovarian cancer, a neuroblastoma, a peripheral nerve sheath cancer, a leukemia, a myeloma, a liver cancer or an osteosarcoma. The HSF inhibitor used in any of the afore-mentioned methods (or uses) for inhibiting or reducing HSF function, reducing the viability of a hyperproliferative cell or treating or preventing a disease mediated or enhanced by an HSF is a small molecule having one or more of the following properties:

(a) it interacts with the DNA-binding domain of a mammalian HSF1 and/or another mammalian HSF that it inhibits;
(b) it has been designed to bind in cavity A of the DNA-binding domain of a mammalian HSF1 and/or the HSF it inhibits;
(c) it mediates its inhibitory effect on the function of a mammalian HSF1 or other mammalian HSF without inhibiting the binding of the HSF1/HSF to target genes;
(d) it interferes with the assembly of transcription complexes on HSF target genes;
(e) it is an acrylamide derivative of formula (I), (II), (IX) or (X).

For the sake of clarity, it is noted that some or all of the latter particular characteristics may be combined in an HSF inhibitor used in any of the afore-mentioned methods.

More specific embodiments of the inhibitors of formula (I) are described by formulae (III), (V) and (VII). More specific embodiments of the inhibitors of formula (II) are described by formulae (IV), (VI) and (VIII), a specific representative of formula (VI) being (E)-3-(5,6-dihydro-4H-[1,3]oxazin-2-yl)-N-methyl-N-(5-(pyridin-3-yl-thiazol-2-yl)acrylamide. More specific embodiments of the inhibitors of formula (IX) are described by formula (XI), and of formula (X) by formula (XII).

Therefore, an HSF inhibitor used in any of the afore-mentioned methods for inhibiting or reducing HSF function, reducing the viability of a hyperproliferative cell or treating or preventing a disease mediated or enhanced by an HSF can be, in the alternative, a compound of formula I or formula II

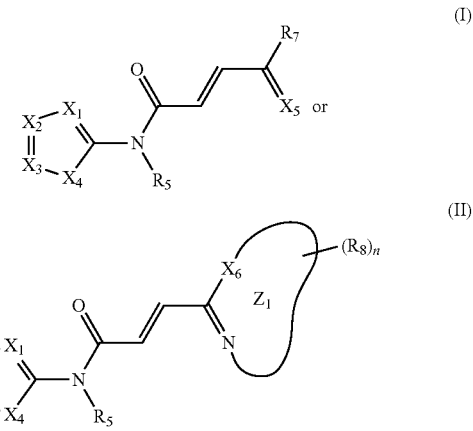

or a salt thereof, whereby
n is 0-8, preferably 0-4 (0, 1, 2, 3 or 4); $X_1$ is N or C(—$R_1$);
$X_2$ is C(—$R_2$), N, or S or O (double bond between $X_3$ and $X_4$ instead of between $X_2$ and $X_3$);
$X_3$ is C(—$R_3$) or N;
$X_4$ is S or O, or C(—$R_4$) or N if $X_2$ is O or S (double bond between $X_3$ and $X_4$ instead of between $X_2$ and $X_3$);
$X_5$ is O, S or N(—$R_6$);
$X_6$ is O, S, N, NH, ($C_1$-$C_4$)alkylN, CH or C(($C_1$-$C_4$)alkyl), $CH_2$ or CH(($C_1$-$C_4$)alkyl);
$R_1$ is H, halo, ($C_1$-$C_4$)alkyl; halo($C_1$-$C_4$)alkyl, H being preferred;
$R_2$, $R_3$, $R_5$ and $R_8$ are independently selected, and each can be H or any substituent, provided that its presence is compatible with the small molecule nature of the inhibitor and, statistically, no more than 10% of any ionizable group it may contain is ionized at neutral pH;

whereby $R_2$ and $R_3$ can form a substituted or unsubstituted 5 to 8 membered aromatic or non-aromatic ring or heterocycle including $X_2$ and $X_3$ as in formulae I A and I B below:

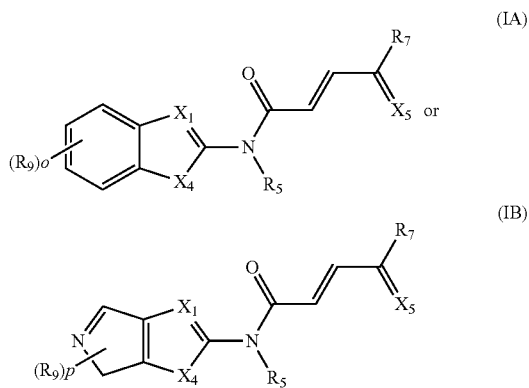

$R_4$ is H, halo, $(C_1-C_4)$alkyl; halo$(C_1-C_4)$alkyl, H being preferred; $R_6$ is H or is selected from halogen, OH, SH, $NH_2$ and $Z_2$, whereby $Z_2$ is a residue comprising from 1 to 4 carbon atoms; $R_7$ is —O—$Z_2$, —S—$Z_2$, —NH—$Z_2$ or —N—$(Z_2)_2$; $R_9$ is selected from (H), alkenyl, alkoxy, alkoxyalkyl, alkoxyalkynyl, alkoxycarbonyl, alkoxycarbonylalkyl, alkoxy-NH.dbd.C(alkyl)-, alkyl, alkylcarbonyl, alkylcarbonylalkyl, alkylcarbonyloxy, alkylsulfonyl, alkylthio, alkynyl, aryl, arylalkoxy, arylalkyl, arylcarbonyl, aryloxy, cyano, cyanoalkyl, cycloalkyl, cycloalkylalkyl, formyl, halogen, haloalkyl, hydroxy, hydroxyalkyl, hydroxycycloalkyl, mercapto, nitro, oxo, phenyl, and $R_{ss}R_{tt}N$—, $R_{ss}R_{tt}N$ carbonyl, $R_{ss}R_{tt}N$ alkyl, wherein $R_{ss}$ and $R_{tt}$ are each independently selected from the group consisting of hydrogen, alkyl, alkylcarbonyl, alkoxycarbonyl, and alkyl$SO_2$—; and $Z_1$ is a 5-8 membered heterocycle.

In alternative embodiments, substituents $R_2$, $R_3$, and $R_5$ in formula I or $R_2$, $R_3$, $R_5$ and $R_8$ in formula II (or in any of formulae III XII in which one or more of these substituents are indicated) are independently selected from the group consisting of (H), hydroxy, formyl, alkylcarbonyl, alkoxy, alkylthio, alkylthioalkyl, alkoxyalkoxy, alkoxycarbonyl, alkoxyalkenyl, alkoxyalkynyl, alkoxycarbonyl-alkoxy, alkyl, alkenyl, alkenyloxy, alkenylthio, alkynyl, alkynylthio, cycloalkyl, cycloalkylthio, cycloalkylalkoxy, cycloalkylalkylthio, cycloalkenylalkoxy, cycloalkenylalkylthio, alkyl$SO_2$—, acryl, arylalkyl, aryloxy, arylthio, arylalkenyl, arylalkynyl, arylcarbonyl, arylalkoxycarbonyl, heteroaryl, heterocycle, heterocyclealkyl, heterocyclealkenyl, heterocyclealkoxy, heterocyclealkylthio, heterocyclealkynyl, heterocyclecarbonyl, heterocycleoxycarbonyl, cyano, cyanoalkyl, cyanoalkoxy, cyanoalkylthio, cyanoalkynyl, cyanoalkenyl, cyanoalkenylalkoxy, cyanoalkenylalkylthio, halogen, haloalkyl, trihaloalkyl, trihaloalkoxy, hydroxyalkyl, hydroxyalkenyl, hydroxyalkynyl, hydroxyalkoxy, hydroxyalkylthio, dihydoxyalkoxy, dihydoxyalkylthio, nitro, $R_f$—O—, $R_f$—S—, HO—N=CH—$(CH2)_{0, 1 \, or \, 2}$-, $R_aR_bN$—, $R_aR_b$Nalkyl-, $R_aR_b$Nalkenyl-, $R_aR_b$Nalkynyl-, $R_aR_b$NC(O)—, $R_aR_b$NC(O)alkynyl-, $R_aR_b$NC(O)alkoxy-, $R_aR_b$N$SO_2$alkoxy-, and $R_w$—O—N=CH—, wherein alkyl may be optionally substituted with O= and $R_tN$=; $R_a$ and $R_b$ are each individually selected from the group consisting of hydrogen, alkyl, alkenyl, alkenylcarbonyl, alkylsulfonyl, alkylcarbonyl, alkoxycarbonyl, alkoxycarbonylalkyl, alkoxycarbonylalkylcarbonyl, alkynyl, aryl, arylalkyl, arylalkenyl, arylcarbonyl, aryloxycarbonyl, arylalkyloxycarbonyl, heteroaryl, heterocycle, heterocyclealkyl, heterocyclealkenyl, heterocyclecarbonyl, heterocyclealkylcarbonyl, haloalkyl, trihaloalkyl, trihaloalkylcarbonyl, haloalkylcarbonyl, heterocycleoxycarbonyl hydroxyalkyl, and hydroxyalkylcarbonyl; $R_t$ is selected from the group consisting of hydrogen, alkyl and HO—; $R_f$ is selected from the group consisting of alkyl, cycloalkyl, cycloalkylalkyl, alkoxyalkyl, alkylthioalkyl, and haloalkyl; R, is selected from the group consisting of hydrogen, alkylcarbonyl-NH-alkyl-NHC(O)-alkyl, alkyl, alkyl(alkyl)N-alkyl-NHC(O)-alkyl, hydroxyalkyl-NHC(O)-alkyl, heterocyclealkyl-NHC(O)-alkyl, heterocycle-NHC(O)-alkyl, and heteroarylalkyl-NHC(O)-alkyl.

In further alternative embodiments, substituents $R_2$, $R_3$, and $R_5$ in formula I or $R_2$, $R_3$, $R_5$ and $R_8$ in formula II (or in any of formulae III XII in which one or more of these substituents are indicated) are independently selected from the group consisting of (H), hydroxy, formyl, alkylcarbonyl, alkoxy, alkylthio, alkylthioalkyl, alkoxyalkoxy, alkoxycarbonyl, alkoxyalkenyl, alkoxyalkynyl, alkoxycarbonyl-alkoxy, alkyl, alkenyl, alkenyloxy, alkynyl, cycloalkyl, cycloalkylalkoxy, cycloalkenylalkoxy, alkyl$SO_2$—, acryl, arylalkyl, aryloxy, arylalkenyl, arylalkynyl, arylcarbonyl, arylalkoxycarbonyl, heteroaryl, heterocycle, heterocyclealkyl, heterocyclealkoxy, heterocyclealkynyl, heterocyclecarbonyl, heterocycleoxycarbonyl, cyano, cyanoalkyl, cyanoalkoxy, cyanoalkynyl, cyanoalkenyl, cyanoalkenylalkoxy, halogen, haloalkyl, trihaloalkyl, trihaloalkoxy, hydroxyalkyl, hydroxyalkenyl, hydroxyalkynyl, hydroxyalkoxy, dihydoxyalkoxy, nitro, $R_f$—O—, HO—N=CH$(CH2)_{0, 1 \, or \, 2}$-, $R_aR_bN$—, $R_aR_b$Nalkyl-, $R_aR_b$Nalkenyl-, $R_aR_b$Nalkynyl-, $R_aR_b$NC(O)—, $R_aR_b$NC(O)alkynyl-, $R_aR_b$NC(O)alkoxy-, $R_aR_b$N$SO_2$alkoxy-, and $R_w$—O—N=CH—, wherein alkyl may be optionally substituted with O= and $R_tN$=; $R_a$ and $R_b$ are each individually selected from the group consisting of hydrogen, alkyl, alkenyl, alkenylcarbonyl, alkylsulfonyl, alkylcarbonyl, alkoxycarbonyl, alkoxycarbonylalkyl, alkoxycarbonylalkylcarbonyl, alkynyl, aryl, arylalkyl, arylalkenyl, arylcarbonyl, aryloxycarbonyl, arylalkyloxycarbonyl, heteroaryl, heterocycle, heterocyclealkyl, heterocyclealkenyl, heterocyclecarbonyl, heterocyclealkylcarbonyl, haloalkyl, trihaloalkyl, trihaloalkylcarbonyl, haloalkylcarbonyl, heterocycleoxycarbonyl hydroxyalkyl, and hydroxyalkylcarbonyl; $R_t$ is selected from the group consisting of hydrogen, alkyl and HO—; $R_f$ is selected from the group consisting of alkyl, cycloalkyl, cycloalkylalkyl, alkoxyalkyl, alkylthioalkyl, and haloalkyl; R, is selected from the group consisting of hydrogen, alkylcarbonyl-NH-alkyl-NHC(O)-alkyl, alkyl, alkyl(alkyl)N-alkyl-NHC(O)-alkyl, hydroxyalkylNHC(O)-alkyl, heterocyclealkyl-NHC(O)-alkyl, heterocycle-NHC(O)-alkyl, and heteroarylalkylNHC(O)-alkyl.

An HSF inhibitor used in any of the afore-mentioned methods for inhibiting or reducing HSF function, reducing the viability of a hyperproliferative cell or treating or preventing a disease mediated or enhanced by an HSF can be, in the alternative, a compound of formula III or formula IV or a salt thereof, whereby n, $R_2$, $R_3$, $R_5$, $R_6$, $R_7$, $R_8$, $X_5$, $X_6$, $Z_1$ and $Z_2$ are as defined before for the inhibitors of formulae I and II.

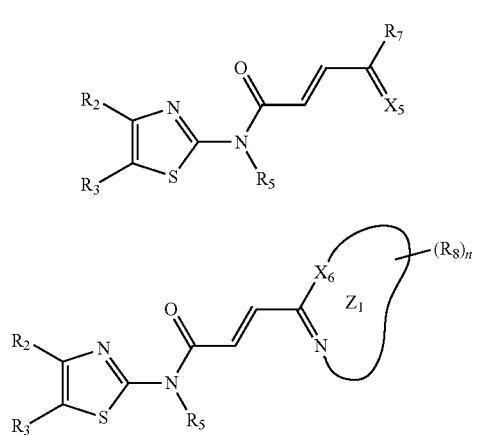

(III)

(IV)

An HSF inhibitor used in any of the afore-mentioned methods for inhibiting or reducing HSF function, reducing the viability of a hyperproliferative cell or treating or preventing a disease mediated or enhanced by an HSF can be, in the alternative, a compound of formula V or formula VI or a salt thereof, whereby n, $R_2$, $R_5$, $R_6$, $R_7$, $R_8$, $X_5$, $X_6$, $Z_1$ and $Z_2$ are as defined before for the inhibitors of formulae I and II; $X_7$ is CH or N (preferably, 3 or less of the $X_7$ being N, and most preferably only one of the $X_7$ being N); $R_{10}$ is defined as $R_5$; and s is 0, 1, 2, 3 or 4.

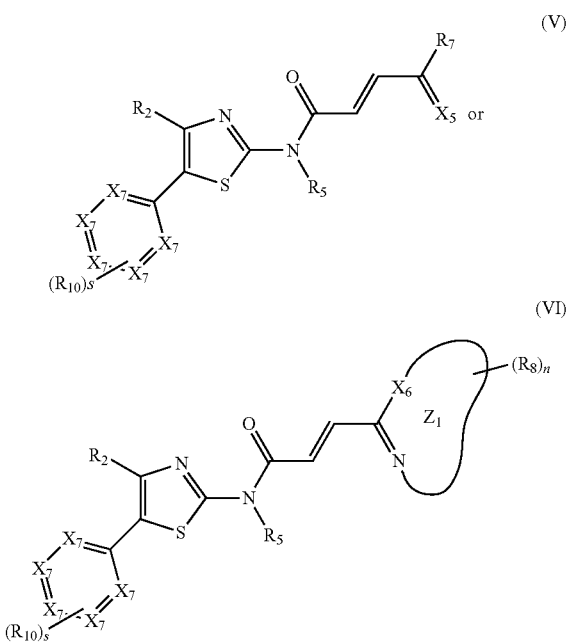

(V)

(VI)

An HSF inhibitor used in any of the afore-mentioned methods for inhibiting or reducing HSF function, reducing the viability of a hyperproliferative cell or treating or preventing a disease mediated or enhanced by an HSF can be, in the alternative, a compound of formula VII or formula VIII or a salt thereof, whereby n, $R_2$, $R_5$, $R_6$, $R_7$, $R_8$, $X_5$, $X_6$, $Z_1$ and $Z_2$ are as defined before for the inhibitors of formulae I and II, and s, $X_7$ and $R_{10}$ are as defined as before for the inhibitors of formulae V and VI.

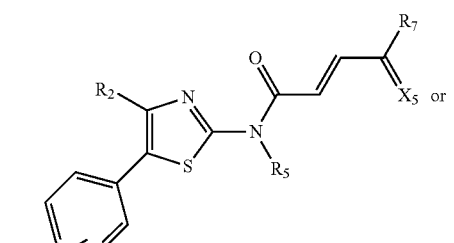

(VII)

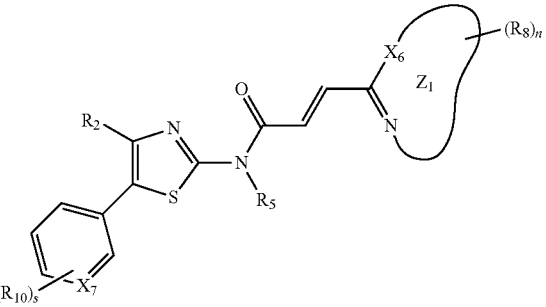

(VIII)

An HSF inhibitor used in any of the afore-mentioned methods for inhibiting or reducing HSF function, reducing the viability of a hyperproliferative cell or treating or preventing a disease mediated or enhanced by an HSF can be (E)-3-(5,6-dihydro-4H-[1,3]oxazin-2-yl)-N-methyl-N-(5-(pyridin-3-yl-thiazol-2-yl)acrylamide or a salt thereof.

An HSF inhibitor used in any of the afore-mentioned methods for inhibiting or reducing HSF function, reducing the viability of a hyperproliferative cell or treating or preventing a disease mediated or enhanced by an HSF can be, in the alternative, a compound of formula IX or formula X or a salt thereof, whereby n, $R_5$, $R_6$, $R_7$, $R_8$, $X_5$, $X_6$, $Z_1$ and $Z_2$ are as defined before, r is 0-4 and $R_{11}$ is defined as $R_5$.

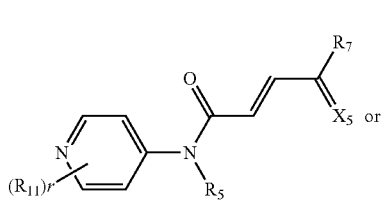

(IX)

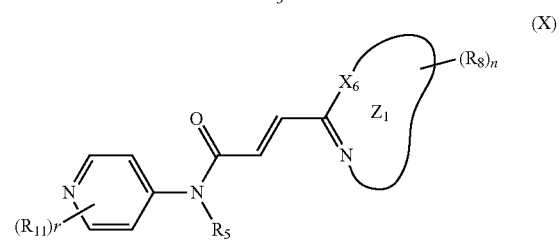

(X)

An HSF inhibitor used in any of the afore-mentioned methods for inhibiting or reducing HSF function, reducing the viability of a hyperproliferative cell or treating or preventing a disease mediated or enhanced by an HSF can be, in the alternative, a compound of formula XI or formula XII or a salt thereof, whereby n, $R_5$, $R_6$, $R_7$, $R_8$, $X_5$, $X_6$, $Z_1$ and $Z_2$ are as previously defined; o is 0, 1, 2, 3 or 4; $R_{12}$ and $R_{13}$ are as $R_5$; and $X_8$ is CH or N. Preferably, 3 or less of the $X_8$ are N, and most preferably only one $X_8$ is N

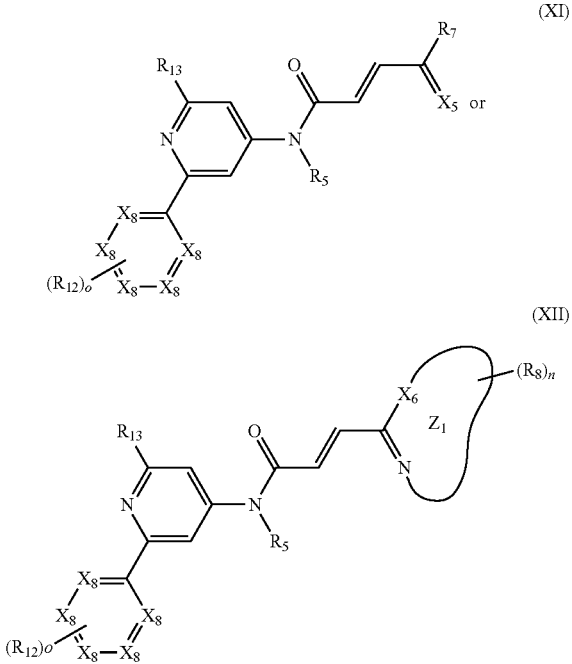

In a different embodiment, the present disclosure further relates to a method for identifying an HSF inhibitor that interacts with (i.e., binds to or acts through) the DNA-binding domain of a mammalian HSF1, the method comprising screening a group of compounds for a compound that inhibits in cultured mammalian cells the stress-induced transcriptional activity of wildtype HSF1 but not of a chimeric HSF1 having a DNA-binding domain from a different transcription factor or DNA-binding protein. The group of compounds may contain small molecules or other compounds such as nucleic acids, aptamers, biologicals, etc. In the latter method, the wildtype HSF1 can be a human HSF1 and the chimeric HSF1 can be derived from a human HSF1. The latter method for identifying an HSF inhibitor that binds to or acts through the HSF1 DNA-binding domain may make use of a mammalian cell line stably transformed with an expressible gene for a chimeric HSF1 comprising a heterologous DNA-binding domain, a first reporter gene responsive to the chimeric HSF1 and a second reporter gene responsive to endogenous HSF1. The cell line can be a human cell line, and the gene for a chimeric HSF1 can be derived from a human HSF1 gene. The cell line can be HeLa-derived cell line Z74.

DETAILED DESCRIPTION

Definitions

Figure 1:
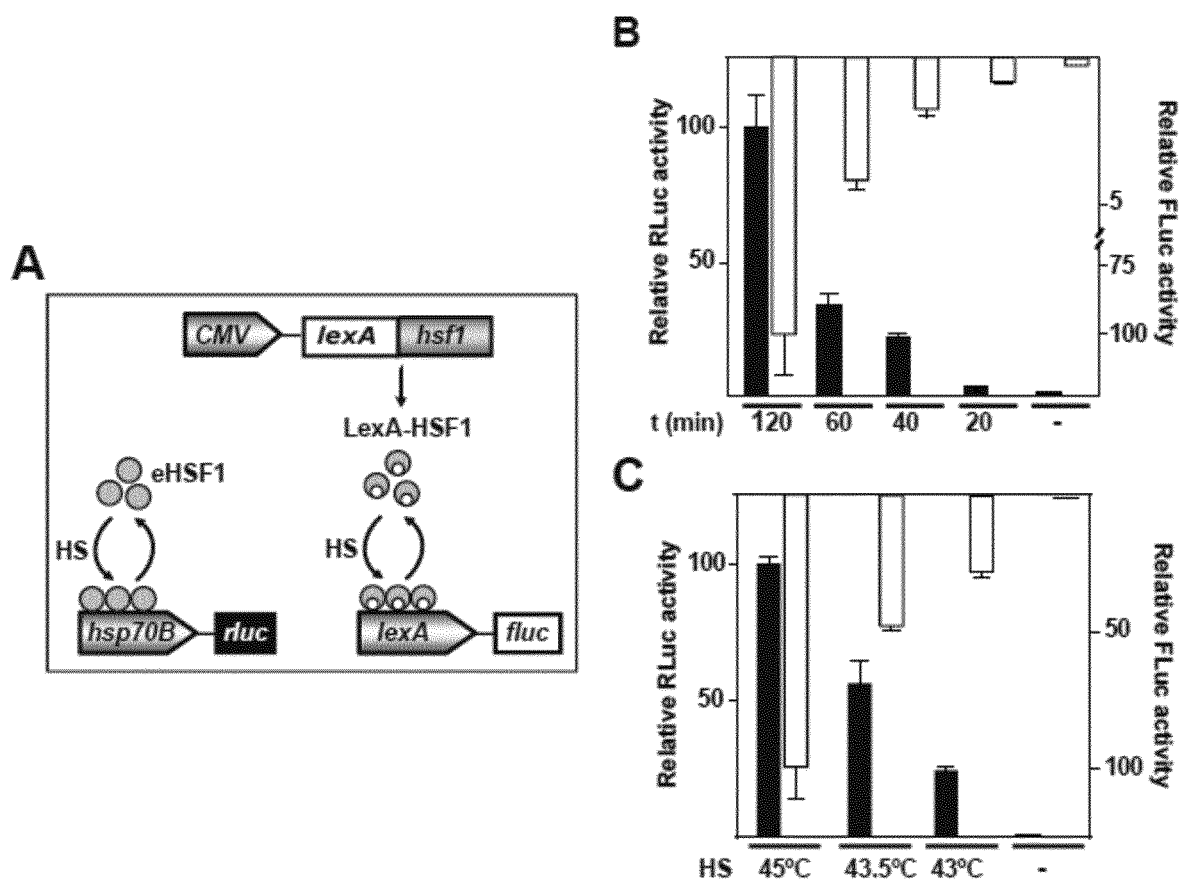
FIG. 1. Characterization of Z74 cells. (A) Z74 cells contain an rluc gene linked to a hsp70B gene promoter controlled by endogenous HSF1 (eHSF1), an expressible gene for chimeric transcription factor LexA-HSF1, and a fluc gene driven by a promoter responsive to LexA-HSF1. (B, C) Transient heat stimulates the transcriptional activities of eHSF1 and LexA-HSF1, which results in an enhanced expression of fluc and rluc genes, respectively. Cells were untreated (−), heat-treated at 43° C. (HS) for the indicated time periods (B) or heated at different temperatures for 30 min (C). RLuc (filled bars) and FLuc activities (empty bars) were assayed 6 h after heat treatment. CMV: cytomegalovirus early promoter.

Unless otherwise defined, all terms shall have their ordinary meaning in the relevant art. The following terms are defined and shall have the following meanings:

The term "alkenyl," as used herein, refers to a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenyloxy," as used herein, refers to an alkenyl group as defined herein, appended to the parent molecular moiety through an oxy group, as defined herein. Representative examples include, but are not limited to, ethoxy, 2-propoxy, 2-methyl-2-propoxy, 3-butoxy, and the like.

The term "alkoxy," as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkyl," as used herein, refers to an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxyalkoxy," as used herein, refers to an alkoxy group, as defined herein, appended to the parent molecular moiety through an alkoxy group, as defined herein.

The term "alkoxyalkenyl," as used herein, refers to an alkoxy group, as defined herein, appended to the parent molecular moiety through an alkene group.

The term "alkoxyalkynyl," as used herein, refers to an alkoxy group, as defined herein, appended to the parent molecular moiety through an alkyne group.

The term "alkoxycarbonyl," as used herein, refers to an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkoxy," as used herein, refers to an alkoxycarbonyl group, as defined herein, appended to the parent molecular moiety through an alkoxy group, as defined herein.

The term "alkyl," as used herein, refers to a straight or branched chain hydrocarbon containing from 1 to 10 carbon atoms. The term "alkyl," as related to the compounds of the present disclosure, refers to $C_1$-alkyl, $C_2$-alkyl, $C_3$-alkyl, $C_4$-alkyl, $C_5$-alkyl, $C_6$-alkyl, $C_7$-alkyl, $C_8$-alkyl, $C_9$-alkyl or $C_{10}$-alkyl. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkyl(alkyl)N—," as used herein, refers to a nitrogen atom, appended to the parent molecular moiety which is substituted with two alkyl group, as defined herein.

The term "alkyl(alkyl)N-alkyl-," as used herein, refers to an alkyl(alkyl)N—, as defined herein, appended to the parent molecular moiety through an alkyl group, as defined herein.

The term "alkyl(alkyl)N-alkyl-NHC(O)—," as used herein, refers to an alkyl(alkyl)N-alkyl, as defined herein, appended to the parent molecular moiety through an NHC (O)— group, as defined herein.

The term "alkyl(alkyl)N-alkyl-NHC(O)-alkyl," as used herein, refers to an alkyl(alkyl)N-alkyl-NHC(O)—, as defined herein, appended to the parent molecular moiety through an alkyl group, as defined herein.

The term "alkylcarbonyl," as used herein, refers to an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonyl-NH—," as used herein, refers to an alkylcarbonyl group, as defined herein, appended to the parent molecular moiety through an unsubstituted nitrogen atom, as defined herein.

The term "alkylcarbonyl-NH-alkyl," as used herein, refers to an alkylcarbonyl-NH— group, as defined herein, appended to the parent molecular moiety through an alkyl group, as defined herein.

The term "alkylcarbonyl-NH-alkyl-NHC(O)—," as used herein, refers to an alkylcarbonyl-NH-alkyl group, as defined herein, appended to the parent molecular moiety through a —NHC(O)group, as defined herein.

The term "alkylcarbonyl-NH-alkyl-NHC(O)-alkyl," as used herein, refers to an alkylcarbonyl-NH-alkyl-NHC (O)— group, as defined herein, appended to the parent molecular moiety through an alkyl group, as defined herein.

The term "alkylsulfonyl," as used herein, refers to an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio," as used herein, refers to an alkyl group, as defined herein, appended to the parent molecular moiety through a sulfur atom.

The term "alkylthioalkyl," as used herein, refers to an alkylthio group, as defined herein, appended to the parent molecular moiety through an alkyl group, as defined herein.

The term "alkynyl," as used herein, refers to a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl," as used herein, means a phenyl group or a bicyclic aryl ring or a tricyclic aryl ring. The aryl groups of the present disclosure can be attached to the parent molecular moiety through any carbon atom within the aryl group while maintaining the proper valence. The bicyclic aryl ring consists of a phenyl group fused to a distal cycloalkyl group or a phenyl group fused to a distal cycloalkenyl group, or a phenyl group fused to a distal heteroaryl group, or a phenyl group fused to a distal heterocycle group. Representative examples of the bicyclic aryl ring include, but are not limited to, 2,3-dihydro-1H-indenyl, 1H-indenyl, naphthyl, 7,8-dihydronaphthalenyl, and 5,6,7,8-tetrahydronaphthalenyl. The tricyclic aryl ring consists of the bicyclic aryl ring fused to a cycloalkyl group or the bicyclic aryl ring fused to a cycloalkyl group or the bicyclic aryl ring fused to another phenyl group. Representative examples of tricyclic aryl ring include, but are not limited to, anthracenyl, azulenyl, 9,10-dihydroanthracenyl, fluorenyl, and 4b,8a,9,10-tetrahydrophenanthrenyl.

The aryl groups of the present disclosure can be substituted with 0, 1, 2, 3 or 4 substituents that are independently selected. The independent substituents can be selected from the group consisting of hydroxy, formyl, alkylcarbonyl, alkoxy, alkylthio, alkylthioalkyl, alkoxyalkoxy, alkoxycarbonyl, alkoxyalkenyl, alkoxyalkynyl, alkoxycarbonylalkoxy, alkyl, alkenyl, alkenyloxy, alkenylthio, alkynyl, alkynylthio, cycloalkyl, cycloalkylthio, cycloalkylalkoxy, cycloalkylalkylthio, cycloalkenylalkoxy, cycloalkenylalkylthio, alkylSO$_2$—, acryl, arylalkyl, aryloxy, arylthio, arylalkenyl, arylalkynyl, arylcarbonyl, arylalkoxycarbonyl, heteroaryl, heterocycle, heterocyclealkyl, heterocyclealkenyl, heterocyclealkoxy, heterocyclealkylthio, heterocyclealkynyl, heterocyclecarbonyl, heterocycleoxycarbonyl, cyano, cyanoalkyl, cyanoalkoxy, cyanoalkylthio, cyanoalkynyl, cyanoalkenyl, cyanoalkenylalkoxy, cyanoalkenylalkylthio, halogen, haloalkyl, trihaloalkyl, trihaloalkoxy, hydroxyalkyl, hydroxyalkenyl, hydroxyalkynyl, hydroxyalkoxy, hydroxyalkylthio, dihydoxyalkoxy, dihydoxyalkylthio, nitro, R$_f$—O—, R$_f$—S—, HO—N=CH—(CH2)$_{0, 1\ or\ 2}$-, R$_a$R$_b$N—, R$_a$R$_b$Nalkyl-, R$_a$R$_b$Nalkenyl-, R$_a$R$_b$Nalkynyl-, R$_a$R$_b$NC(O)—, R$_a$R$_b$NC(O)alkynyl-, R$_a$R$_b$NC(O)alkoxy-, R$_a$R$_b$NSO$_2$alkoxy-, and R$_w$—O—N=CH—, wherein alkyl may be optionally substituted with O= and R$_t$N=; R$_a$ and R$_b$ are each individually selected from the group consisting of hydrogen, alkyl, alkenyl, alkenylcarbonyl, alkylsulfonyl, alkylcarbonyl, alkoxycarbonyl, alkoxycarbonylalkyl, alkoxycarbonylalkylcarbonyl, alkynyl, aryl, arylalkyl, arylalkenyl, arylcarbonyl, aryloxycarbonyl, arylalkyloxycarbonyl, heteroaryl, heterocycle, heterocyclealkyl, heterocyclealkenyl, heterocyclecarbonyl, heterocyclealkylcarbonyl, haloalkyl, trihaloalkyl, trihaloalkylcarbonyl, haloalkylcarbonyl, heterocycleoxycarbonyl hydroxyalkyl, and hydroxyalkylcarbonyl; R$_t$ is selected from the group consisting of hydrogen, alkyl and HO—; R$_f$ is selected from the group consisting of alkyl, cycloalkyl, cycloalkylalkyl, alkoxyalkyl, alkylthioalkyl, and haloalkyl; R, is selected from the group consisting of hydrogen, alkylcarbonyl-NH-alkyl-NHC(O)-alkyl, alkyl, alkyl(alkyl)N-alkyl-NHC(O)-alkyl, hydroxyalkyl-NHC(O)-alkyl, heterocyclealkyl-NHC(O)-alkyl, heterocycle-NHC(O)-alkyl, and heteroarylalkyl-NHC(O)-alkyl. Alternatively, the substituents can be selected from the group consisting of hydroxy, formyl, alkylcarbonyl, alkoxy, alkylthio, alkylthioalkyl, alkoxyalkoxy, alkoxycarbonyl, alkoxyalkenyl, alkoxyalkynyl, alkoxycarbonylalkoxy, alkyl, alkenyl, alkenyloxy, alkynyl, cycloalkyl, cycloalkylalkoxy, cycloalkenylalkoxy, alkylSO$_2$—, acryl, arylalkyl, aryloxy, arylalkenyl, arylalkynyl, arylcarbonyl, arylalkoxycarbonyl, heteroaryl, heterocycle, heterocyclealkyl, heterocyclealkenyl, heterocyclealkoxy, heterocyclealkynyl, heterocyclecarbonyl, heterocycleoxycarbonyl, cyano, cyanoalkyl, cyanoalkoxy, cyanoalkynyl, cyanoalkenyl, cyanoalkenylalkoxy, halogen, haloalkyl, trihaloalkyl, trihaloalkoxy, hydroxyalkyl, hydroxyalkenyl, hydroxyalkynyl, hydroxyalkoxy, dihydoxyalkoxy, nitro, R$_f$—O—, HO—N=CH—(CH2)$_{0, 1\ or\ 2}$-, R$_a$R$_b$N—, R$_a$R$_b$Nalkyl-, R$_a$R$_b$Nalkenyl-, R$_a$R$_b$Nalkynyl-, R$_a$R$_b$NC(O)—, R$_a$R$_b$NC(O)alkynyl-, R$_a$R$_b$NC(O)alkoxy-, R$_a$R$_b$NSO$_2$alkoxy-, and R$_w$—O—N=CH—, wherein alkyl may be optionally substituted with O= and R$_t$N=; R$_a$ and R$_b$ are each individually selected from the group consisting of hydrogen, alkyl, alkenyl, alkenylcarbonyl, alkylsulfonyl, alkylcarbonyl, alkoxycarbonyl, alkoxycarbonylalkyl, alkoxycarbonylalkylcarbonyl, alkynyl, aryl, arylalkyl, arylalkenyl, arylcarbonyl, aryloxycarbonyl, arylalkyloxycarbonyl, heteroaryl, heterocycle, heterocyclealkyl, heterocyclealkenyl, heterocyclecarbonyl, heterocyclealkylcarbonyl, haloalkyl, trihaloalkyl, trihaloalkylcarbonyl, haloalkylcarbonyl, heterocycleoxycarbonyl hydroxyalkyl, and hydroxyalkylcarbonyl; R$_t$ is selected from the group consisting of hydrogen, alkyl and HO—; R$_f$ is selected from the group consisting of alkyl, cycloalkyl, cycloalkylalkyl, alkoxyalkyl, alkylthioalkyl, and haloalkyl; R$_w$ is selected from the group consisting of hydrogen, alkylcarbonyl-NH-alkyl-NHC(O)-alkyl, alkyl, alkyl(alkyl) N-alkyl-NHC(O)-alkyl, hydroxyalkylNHC(O)-alkyl, heterocyclealkyl-NHC(O)-alkyl, heterocycle-NHC(O)-alkyl, and heteroarylalkylNHC(O)-alkyl.

The term "arylalkoxy," as used herein, refers to an aryl group, as defined herein, appended to the parent molecular moiety through an alkoxy group, as defined herein. Representative examples of arylalkoxy include, but are not limited to, 2-phenylethoxy, 3-naphth-2-ylpropoxy, and 5-phenylpentyloxy.

The term "arylalkyl," as used herein, refers to an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "arylalkynyl," as used herein, refers to an aryl group, as defined herein, appended to the parent molecular moiety through an alkyne group, as defined herein. The term "arylalkyloxy," as used herein, refers to an arylalkyl group, as defined herein, appended to the parent molecular moiety through an oxy group, as defined herein. Representative examples of arylalkyloxy include, but are not limited to, benzyloxy, phenylpropoxy.

The term "arylalkyloxycarbonyl," as used herein, refers to an arylalkyloxy group, as defined herein, appended to the parent molecular moiety through a carbonyl group, as defined herein. Representative examples of arylalkyloxycarbonyl include, but are not limited to, benzyl carboxylate, phenylpropyl carboxylate.

The term "arylcarbonyl," as used herein, refers to an aryl group, as defined herein, appended to the parent molecular moiety through a carbonyl group, as defined herein. Representative examples of arylcarbonyl include, but are not limited to, benzoyl and naphthoyl.

The term "aryloxy," as used herein, refers to an aryl group, as defined herein, appended to the parent molecular moiety through an oxy group, as defined herein. Representative examples of aryloxy groups include, but are not limited to, phenoxy.

The term "aryloxycarbonyl," as used herein, refers to an aryloxy group, as defined herein appended to the parent molecular moiety through a carbonyl group, as defined herein. Representative examples of aryloxycarbonyl groups include, but are not limited to, phenoxycarbonyl.

The term "biaryl," as used herein, refers to an aryl group as defined herein, appended to the parent molecular moiety through an aryl group, as defined herein. Representative examples of biaryl include, but are not limited to 4-biphenyl, 3-biphenyl, 2-biphenyl.

The term "carbonyl," as used herein, refers to a —C(O)— group.

The term "cyano," as used herein, refers to a —CN group.

The term "cyanoalkyl," as used herein, refers to a cyano group, as defined herein, appended to the parent molecular moiety through an alkyl group, as defined herein. Representative examples of cyanoalkyl include, but are not limited to, cyanomethyl, 2-cyanoethyl, and 3-cyanopropyl.

The term "cyanoalkoxy," as used herein, refers to a cyano group, as defined herein, appended to the parent molecular moiety through an alkyoxy group, as defined herein.

The term "cyanoalkynyl," as used herein, refers to a cyano group, as defined herein, appended to the parent molecular moiety through an alkyne group, as defined herein.

The term "cycloalkyl," as used herein, refers to a monocyclic, bicyclic, or tricyclic ring system. Monocyclic ring systems are exemplified by a saturated cyclic hydrocarbon group containing from 3 to 8 carbon atoms. Examples of monocyclic ring systems include cyclopropyl, cyclobutyl, cyclopentyl, cyclohexyl, cycloheptyl, and cyclooctyl. Bicyclic ring systems are exemplified by a bridged monocyclic ring system in which two non-adjacent carbon atoms of the monocyclic ring are linked by an alkylene bridge of between one and three additional carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Tricyclic ring systems are exemplified by a bicyclic ring system in which two non-adjacent carbon atoms of the bicyclic ring are linked by a bond or an alkylene bridge of between one and three carbon atoms. Representative examples of tricyclic-ring systems include, but are not limited to, tricyclo[3.3.1.0.sup.3,7]nonane and tricyclo[3.3.1.1.sup.3,7]decane (adamantane). The term "cycloalkyl," as related to the compounds of the present disclosure refer to $C_3$-cycloalkyl, $C_4$-cycloalkyl, $C_5$-cycloalkyl, $C_6$-cycloalkyl, $C_7$-cycloalkyl or $C_8$-cycloalkyl.

The cycloalkyl groups of this disclosure can be substituted with 0, 1, 2, or 3 substituents independently selected from alkenyl, alkoxy, alkoxyalkyl, alkoxycarbonyl, alkoxycarbonylalkyl, alkyl, alkylcarbonyl, alkylcarbonylalkyl, alkylcarbonyloxy, alkylsulfonyl, alkylthio, alkynyl, carboxy, carboxyalkyl, cyano, cyanoalkyl, formyl, halogen, haloalkyl, heterocycle, heterocyclealkyl, hydroxy, hydroxyalkyl, mercapto, nitro, oxo, phenyl and $R_{ss}R_{tt}N$— wherein $R_{ss}$ and $R_{tt}$ are defined herein.

The term "cycloalkylalkyl," as used herein, refers to a cycloalkyl group, as defined herein appended to the parent molecular moiety through an alkyl group, as defined herein. Representative examples of cycloalkylalkyl group include, but are not limited to cyclopentylpropyl, cyclohexyl 2-methylbutyl.

The term "cycloalkenyl," as used herein, refers to a monocyclic, bicyclic, or tricyclic ring system which contains 1 or 2 double bonds but is not aromatic. Monocyclic ring systems are exemplified by an unsaturated cyclic hydrocarbon group containing from 3 to 8 carbon atoms. Examples of monocyclic ring systems include cyclopropenyl, cyclobutenyl, cyclopentenyl, cyclohexenyl, cycloheptenyl, and cyclooctenyl. Bicyclic ring systems are exemplified by a bridged monocyclic ring system in which two non-adjacent carbon atoms of the monocyclic ring are linked by an alkylene bridge of between one and three additional carbon atoms.

The cycloalkenyl groups of this disclosure can be substituted with 1, 2, or 3 substituents independently selected from alkenyl, alkoxy, alkoxyalkyl, alkoxycarbonyl, alkoxycarbonylalkyl, alkyl, alkylcarbonyl, alkylcarbonylalkyl, alkylcarbonyloxy, alkylsulfonyl, alkylthio, alkynyl, cyano, cyanoalkyl, formyl, halogen, haloalkyl, heterocycle, heterocyclealkyl, hydroxy, hydroxyalkyl, mercapto, nitro, phenyl and $R_{ss}R_{tt}N$— wherein $R_{ss}$ and $R_{tt}$ are defined herein.

The term "cycloalkenylalkoxy," as used herein, refers to a cycloalkenyl group as defined herein appended to the parent molecular moiety through an alkoxy group, as defined herein.

The term "dihydroxyalkoxy," as used herein, refers to two hydroxy groups as defined herein, appended to the parent molecular moiety through an alkoxy group, as defined herein. Representative examples of alkyl include, but are not limited to, 2-dihydroxyethoxy, 2,3-dihydroxypropoxy, 3,4-dihydroxybutoxy and the like.

The term "formyl," as used herein, refers to a —C(O)H group.

The term "halo" or "halogen," as used herein, refers to —Cl, —Br, —I or —F.

The term "haloalkyl," as used herein, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, means a monocyclic heteroaryl ring or a bicyclic heteroaryl ring. The monocyclic heteroaryl ring is a 5 or 6 membered ring. The 5 membered ring has two double bonds and contains one, two, three or four heteroatoms independently selected from the group consisting of N, O, and S. The 6 membered ring has three double bonds and contains one, two, three or four heteroatoms independently selected from the group consisting of N, O, and S. The bicyclic heteroaryl ring consists of the 5 or 6 membered heteroaryl ring fused to a distal aryl group or the 5 or 6 membered heteroaryl ring fused to a distal cycloalkyl group or the 5 or 6 membered heteroaryl ring fused to a distal cycloalkenyl group or the 5 or 6 membered heteroaryl ring fused to a distal 5 or 6 membered heteroaryl ring, or the 5 or 6 membered heteroaryl ring fused to a distal 5 or 6 membered heterocycle ring. Nitrogen heteroatoms contained within the heteroaryl may be optionally oxidized to the N-oxide or optionally protected with a nitrogen protecting group known to those of skill in the art. The heteroaryl is connected to the parent molecular moiety through any carbon atom or any nitrogen atom contained within the heteroaryl. Representative examples of heteroaryl include, but are not limited to, benzothienyl, benzoxadiazolyl, cinnolinyl, 5,6-dihydroisoquinolinyl, 7,8-dihydroisoquinolinyl, 5,6-dihydroquinolinyl, 7,8-dihydroquinolinyl, furopyridinyl, furyl, imidazolyl, indazolyl, indolyl, isoxazolyl, isoquinolinyl, isothiazolyl, naphthyridinyl, oxadiazolyl, oxazolyl, pyridinyl, pyridazinyl, pyrimidinyl, pyrazinyl, pyrazolyl, pyrrolyl, pyridinium N-oxide, quinolinyl, 5,6,7,8-tetrahydroisoquinolinyl, 5,6,7,8-tetrahydroquinolinyl, tetrazolyl, thiadiazolyl, thiazolyl, thienopyridinyl, thienyl, triazolyl, and triazinyl.

According to the present disclosure, heteroaryls can be substituted with 0, 1, 2, 3 or 4 substituents independently selected. The substituents can be selected from the groups described under "aryl".

The term "heteroarylalkyl," as used herein, refers to a heteroaryl, as defined herein, appended to the parent molecular moiety through an alkyl group, as defined herein.

The term "heteroaryl-NHC(O)—," as used herein, refers to an heteroaryl-, as defined herein, appended to the parent molecular moiety through an NHC(O)— group, as defined herein. The term "heteroaryl-NHC(O)-alkyl," as used herein, refers to an heteroaryl-NHC(O)—, as defined herein, appended to the parent molecular moiety through an alkyl-group, as defined herein.

The term "heteroarylalkyl-NHC(O)—," as used herein, refers to an heteroarylalkyl-, as defined herein, appended to the parent molecular moiety through an NHC(O)— group, as defined herein.

The term "heteroarylalkyl-NHC(O)-alkyl," as used herein, refers to an heteroarylalkyl-NHC(O)—, as defined herein, appended to the parent molecular moiety through an alkyl-group, as defined herein.

The term "heterocycle" or "heterocyclic" as used herein, means a monocyclic heterocyclic ring or a bicyclic heterocyclic ring or a tricyclic heterocyclic ring. The monocyclic heterocyclic ring consists of a 3, 4, 5, 6, 7 or 8 membered ring containing at least one heteroatom independently selected from oxygen, nitrogen and sulfur. The 3 or 4 membered ring contains 1 heteroatom selected from the group consisting of O, N and S. The 5 membered ring contains zero or one double bond and one, two or three heteroatoms selected from the group consisting of 0, N and S. The 6 or 7 membered ring contains zero, one or two double bonds and one, two or three heteroatoms selected from the group consisting of O, N and S. The 8 membered ring contains zero, one, two or three double bonds and one, two or three heteroatoms selected from the group consisting of O, N and S. Representative examples of the monocyclic heterocyclic ring include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocyclic ring consists of the monocyclic heterocyclic ring fused to a distal aryl ring or the monocyclic heterocyclic ring fused to a distal cycloalkyl ring or the monocyclic heterocyclic ring fused to a distal cycloalkenyl ring or the monocyclic heterocyclic ring fused to a distal monocyclic heterocyclic ring, or the monocyclic heterocyclic ring fused to a distal monocyclic heteroaryl ring. Representative examples of the bicyclic heterocyclic ring include, but are not limited to, 1,3-benzodioxolyl, 1,3-benzodithiolyl, 2,3-dihydro-1,4-benzodioxinyl, 2,3-dihydro-1-benzo furanyl, 2,3-dihydro-1-benzothienyl, 2,3-dihydro-1H-indolyl, and 1,2,3,4-tetrahydroquinolinyl. The tricyclic heterocyclic ring consists of the bicyclic heterocyclic ring fused to a phenyl group or the bicyclic heterocyclic ring fused to a cycloalkyl group or the bicyclic heterocyclic ring fused to a cycloalkenyl group or the bicyclic heterocyclic ring fused to another monocyclic heterocyclic ring. Representative examples of tricyclic heterocyclic rings include, but are not limited to, 2,3,4,4a,9,9a-hexahydro-1H-carbazolyl, 5a,6,7,8,9,9a-hexahydrodibenzo[b,d]furanyl, and 5a,6,7,8,9,9a-hexahydrodibenzo[b,d]thienyl. According to the present disclosure, heterocycles of the present disclosure can be substituted with 0-8, more preferably 0-4, i.e, 0, 1, 2, 3 or 4, substituents that are independently selected. Substituents can be selected from the groups described under "aryl".

The term "heterocyclealkyl," as used herein, refers to a heterocycle, as defined herein, appended to the parent molecular moiety through an alkyl group, as defined herein. Representative examples of heterocyclealkyl include, but are not limited to, pyridin-3-ylmethyl and 2-pyrimidin-2-ylpropyl and the like.

The term "heterocyclealkyl-NHC(O)—," as used herein, refers to an heterocyclealkyl-, as defined herein, appended to the parent molecular moiety through an NHC(O— group, as defined herein.

The term "heterocyclealkyl-NHC(O)-alkyl," as used herein, refers to an heterocyclealkyl-NHC(O)—, as defined herein, appended to the parent molecular moiety through an alkyl-group, as defined herein.

The term "heterocycle-NHC(O)—," as used herein, refers to an heterocycle, as defined herein, appended to the parent molecular moiety through an NHC(O)— group, as defined herein.

The term "heterocycle-NHC(O)-alkyl," as used herein, refers to an heterocycle-NHC(O)—, as defined herein, appended to the parent molecular moiety through an alkyl-group, as defined herein.

The term "heterocyclealkenyl," as used herein, refers to a heterocycle, as defined herein, appended to the parent molecular moiety through an alkenyl group, as defined herein.

The term "heterocyclealkoxy," as used herein, refers to a heterocycle, as defined herein, appended to the parent molecular moiety through an alkoxy group, as defined herein.

The term "heterocyclecarbonyl," as used herein, refers to a heterocycle, as defined herein, appended to the parent molecular moiety through a carbonyl group, as defined herein. Representative examples of heterocyclecarbonyl include, but are not limited to, pyridin-4-ylethanone, pyridin-4-ylpropanone.

The term "heterocycleoxy," as used herein, refers to a heterocycle, as defined herein, appended to the parent molecular moiety through an oxy group, as defined herein. Representative examples of heterocycleoxy include, but are not limited to, pyridin-2-ol, pyridin-4-ol, thiophen-2-ol.

The term "heterocycleoxycarbonyl," as used herein, refers to a heterocycleoxy, as defined herein, appended to the parent molecular moiety through a carbonyl group, as defined herein. Representative examples of heterocyclecarbonyl include, but are not limited to, pyridin-4-ylcarboxylate, thiophene-2-ylcarboxylate.

The term "heterocycleoxyalkynyl," as used herein, refers to a heterocycleoxy, as defined herein, appended to the parent molecular moiety through an alkyne group, as defined herein.

The term "hydroxy," as used herein, refers to an —OH group.

The term "hydroxyalkyl," as used herein, refers to a hydroxy group, as defined herein, appended to the parent molecular moiety through an alkyl group, as defined herein. Representative examples of hydroxyalkyl include, but are not limited to, 2-hydroxyethyl, 2-hydroxypropyl, 3-hydroxybutyl and the like.

The term "hydroxyalkyl-NHC(O)—," as used herein, refers to an hydroxyalkyl-, as defined herein, appended to the parent molecular moiety through an NHC(O)— group, as defined herein.

The term "hydroxyalkyl-NHC(O)-alkyl," as used herein, refers to an hydroxyalkyl-NHC(O)—, as defined herein, appended to the parent molecular moiety through an alkyl-group, as defined herein.

The term "hydroxyalkenyl," as used herein, refers to a hydroxy group, as defined herein, appended to the parent molecular moiety through an alkenyl group, as defined herein.

The term "hydroxyalkynyl," as used herein, refers to a hydroxy group, as defined herein, appended to the parent molecular moiety through an alkyne group, as defined herein.

The term "hydroxyalkoxy," as used herein, refers to a hydroxy group as defined herein, appended to the parent molecular moiety through an alkoxy group, as defined herein. Representative examples include, but are not limited to, 2-hydroxyethoxy, 2-hydroxypropoxy, 3-hydroxybutoxy and the like.

The term "hydroxycycloalkyl," as used herein, refers to a hydroxy group, as defined herein, appended to the parent molecular moiety through an cycloalkyl group, as defined herein.

The term "—NHC(O)—," as used herein, refers to an unsubstituted nitrogen atom, as defined herein, appended to the parent molecular moiety through a carbonyl group, as defined herein.

The term "trihaloalkyl," as used herein, refers to three halogen atoms, appended to the parent molecular moiety through an alkyl group, as defined herein.

The term "trihaloalkoxy," as used herein, refers to three halogen atoms, appended to the parent molecular moiety through an alkoxy group, as defined herein.

The terms "alkenylthio", "alkynylthio", "cycloalkylthio", "cycloalkylalkylthio", "cycloalkenylalkylthio", "arylthio", "heterocyclealkylthio", "cyanoalkylthio", "cyanoalkenylthio", "hydroxyalkylthio", and "dihydroxythio", as used herein, refer to alkenyl, alkynyl, cycloalkyl, cycloalkylalkyl, cycloalkenylalkyl, aryl, heterocyclealkyl, cyanoalkyl, cyanoalkenyl, hydroxyalkyl and dihydroxy moieties as defined herein that are appended to the parent molecular moiety through a sulfur atom.

The term "inhibit" is understood to encompass both partial and complete inhibition.

The terms "HSF inhibitor", "inhibitor of HSF" or the abbreviation "$I_{HSF}$" mean a small molecule compound that, inter alia, is capable of inhibiting the prototypical function of heat shock factor 1, abbreviated as HSF1 (also known as heat shock transcription factor or HSTF), which function is to mediate stress-induced (typically heat-induced) transient accumulation of transcripts (or protein products) of its target genes, which are genes that are functionally linked to stress-inducible promoters, which are typically promoters comprising one or more HSE sequences.

"$I_{HSF}$" is also referred to herein as "compound", "compound of the disclosure" or "active compound". It will be clear from the context when the latter terms are meant to refer to $I_{HSF}$. The nucleotide sequence of human hsf1 cDNA and the human HSF1 amino acid sequence were first reported by Rabindran et al. (1991). Proc. Natl. Acad. Sci. USA 88: 6906-6910. For the corresponding first report for human hsf2 cDNA and amino acid sequence, see Schuetz et al. (1991). Proc. Natl. Acad. Sci. USA 88: 6911-6915. For human hsf4, see Nakai et al. (1997) Mol. Cell. Biol. 17: 469-481. See also UniProtKB-Q00613, Q03933 and Q9ULV5.

"Promoter" is a nucleotide sequence that directs the transcriptional expression of a functionally linked gene. A promoter may be constitutively active in a ubiquitous or a cell type-restricted fashion. Alternatively, it may also be inducible, i.e., become active, or more active, in response to some stimulation. Stress-inducible hsp gene promoters are examples of inducible promoters.

The term "heat shock gene (hsp gene)" is understood herein as referring to a gene whose activity is enhanced when the eukaryotic cell containing the gene is exposed to a temperature above its normal growth temperature. Typically, such genes are activated when the temperature to which the cell is normally exposed is raised by 3-10° C. Heat shock genes comprise genes for the "classical" heat shock proteins, i.e., HSP110, HSP90, HSP70, HSP60, HSP40, and HSP20-30. They also include other heat-inducible genes such as genes for MDR1, ubiquitin, FKBP52, hemoxidase and other proteins. The promoters of these genes, the "heat shock promoters (hsp promoters)", contain characteristic sequence elements referred to as heat shock elements (HSE) that consist of perfect or imperfect sequence modules of the type NGAAN or AGAAN, which modules are arranged in alternating orientations (Amin, J. et al. (1988) Mol. Cell. Biol 8: 3761-3769; Xiao, H. and Lis, J. T. (1988) Science 239: 1139-1142; Fernandes, M. et al. (1994) Nucleic Acids Res. 22: 167-173). These elements are highly conserved in all eukaryotic cells. HSE sequences are binding sites for heat shock transcription factors (HSFs; reviewed in Wu, C. (1995) Annu. Rev. Cell Dev. Biol. 11, 441-469). The factor primarily responsible for activation of hsp genes in mammalian cells exposed to heat or a proteotoxic stress is HSF1 (Baler, R. et al. (1993) Mol. Cell. Biol. 13: 2486-2496; McMillan, D. R. et al. (1998) J. Biol. Chem. 273: 7523-7528). Preferred promoters for use in assessing HSF1 function are those from inducible hsp70 genes. A particularly preferred hsp promoter is the promoter of the human hsp70B gene (Voellmy, R. et al. (1985) Proc. Natl. Acad. Sci. USA 82: 4949-4953).

The term "treatment" refers to any process, action, application, therapy, or the like, wherein a mammal, in particular a human being, is subject to medical aid with the object of improving the mammal's condition, directly or indirectly.

As used herein, the term "pharmaceutically acceptable salt" refers to those salts which are, within the scope of sound medical judgment, suitable for use in contact with the tissues of humans or mammalian animals without undue toxicity, irritation, allergic response and the like, and are commensurate with a reasonable benefit/risk ratio. Pharmaceutically acceptable salts are well known in the art. For example, Berge and colleagues describe pharmaceutically acceptable salts in detail in J. Pharm. Sci. 66: 1-19 (1977). The salts can be prepared during the final isolation and purification of the compounds of the disclosure, or separately by reacting the free base function with a suitable organic acid or inorganic acid. Examples of pharmaceutically acceptable nontoxic acid addition salts include, but are not limited to, salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid, lactobionic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, sulfonate and aryl sulfonate.

The term "pharmaceutically acceptable prodrugs" as used herein refers to those prodrugs of the compounds of the present disclosure which are, within the scope of sound medical judgment, suitable for use in contact with the tissues of humans and mammalian animals with undue toxicity, irritation, allergic response, and the like, commensurate with a reasonable benefit/risk ratio, and effective for their intended use. "Prodrug", as used herein means a compound which is convertible in vivo by metabolic means (e.g. by hydrolysis) to a compound of the disclosure. Various forms of prodrugs are known in the art, for example, as discussed in Bundgaard, H. (ed.), Design of Prodrugs, Elsevier (1985); Widder, K. J. and Green, R. (eds.), Meth. Enzymol., vol. 112, Academic Press (1985); Krogsgaard-Larsen, P. and Bundgaard, H. (eds.). "Design and Application of Prodrugs, Textbook of Drug Design and Development", Chapter 13, pp. 351-85 (1991); Nielson, N. M. and Bundgaard, H. (1988) J. Pharm. Sci. 77:285-98; Higuchi, T. and Stella, V. (eds.) Pro-drugs as Novel Drug Delivery Systems, American Chemical Society (1975); and Testa, B. and Mayer, J. M. "Hydrolysis In Drug And Prodrug Metabolism: Chemistry, Biochemistry And Enzymology," John Wiley and Sons, Ltd. (2003).

As used herein, "pharmaceutically acceptable carrier or excipient" is intended to include any and all solvents, dispersion media, coatings, antibacterial and antifungal agents, isotonic and absorption delaying agents, and the like, compatible with pharmaceutical administration, such as sterile pyrogen-free water. Suitable carriers are described in Remington's Pharmaceutical Sciences (Mack Publishing Co., Easton, Pa., 19th ed. 1995), a standard reference text in the field, which is incorporated herein by reference. Some examples of materials which can serve as pharmaceutically acceptable carriers are sugars such as lactose, glucose and sucrose; cyclodextrins such as alpha-, beta- and gamma-cyclodextrins; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. Also encompassed are emulsifiers/surfactants such as cremophor EL and solutol HS15, lecithin and phospholipids such as phosphatylcholine. Liposomes may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The term "subject" as used herein refers to a mammalian subject. Preferably, the subject is a human subject.

The term "small molecule" means a molecule with a molecular weight of less than about 2,000 daltons, preferably less than about 1,000 daltons and, most preferably, less than 500 daltons. Further to the latter size limitation, to avoid any possible doubt, the term "small molecule" as used herein shall be specifically defined to exclude nucleic acids or nucleic acid aptamers.

By an "effective amount" of an HSF inhibitor of the disclosure is meant an amount of the compound which, when administered once or multiple times over the course of a treatment, confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of an HSF inhibitor of the disclosure may range from about 0.01 mg/kg body weight to about 50 mg/kg body weight, preferably from about 0.1 to about 30 mg/kg body weight. Effective doses will also vary depending on route of administration, as well as the possibility of co-usage with other agents. It will be understood, however, that the total daily usage of the compounds and compositions of the present disclosure will be decided by the attending physician within the scope of sound medical judgment. The specific effective dose level for any particular patient will depend upon a variety of factors including the disorder being treated and the severity of the disorder; the activity of the specific active compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts. It is noted that when used in the context of prophylaxis or prevention, an "effective amount" of a compound of the disclosure is meant to be an amount of the compound which, when administered once or multiple times over the course of a treatment, confers a desired prophylactic effect on the treated subject.

HSF Inhibitors

Mammalian HSF1 is regulated at multiple levels. Zou, J. et al. (1998) Cell 94: 471-480; Guo, Y. et al. (2001) J. Biol. Chem. 276, 45791-45799; Guettouche, T. et al. (2005) BMC Biochemistry 6: 4; Voellmy, R. (2006) Handb. Exp. Pharmacol. (172): 43-68; Boyault et al. (2007) Genes Dev. 21: 2172-2181. In an unstressed mammalian or human cell, HSF1 is present as a heterocomplex with HSP90 and other co-chaperones and co-factors, including CHIP and HDAC6. In this form, HSF1 is incapable of binding to and transactivating an HSE-containing promoter. Inactive HSF1 complex appears to be distributed throughout the cell. When the cell experiences a physical or chemical stress, the HSF1 heterocomplex disassembles partially or completely, and HSF1 homotrimerizes. Homotrimeric HSF1 is capable of binding to HSE DNA sequences. Also, homotrimeric factor concentrates in the nucleus. While activation of DNA-binding ability appears to be a direct consequence of factor trimerization, activation of the transcription-enhancing ability of the factor is controlled by additional factors. Depending on the level of stress experienced by the cell, homotrimeric factor can be sidelined by formation of an HSP90-containing complex. The lower the level of stress, the more likely is inactivation of trimeric HSF1 by formation of such a complex. Transactivation ability is also enhanced/reduced by post-translational modification, primarily phosphorylation/dephosphorylation and deactylation/acetylation. Guettouche, T. et al. (2005); Westerheide, S. D. et al. (2009) Science 323: 1063-1066. HSF1 is also stabilized by acetylation at lysine residues that are not critical to factor activity. Raychaudhuri, S. et al. (2014) Cell 156: 975-985. A number of drug substances used in human therapy cause activation of HSF1, resulting in induced expression of HSPs and a buildup of tolerance (and inhibition of apoptotic mechanisms). Well known examples of drug substances that cause HSF1 activation are inhibitors of HSP90, inhibitors of proteasome function and inhibitors of HDAC6. This induction of HSP expression appears to result in a suboptimal efficacy of the drugs. Bagatell, R. et al. (2000) Clin. Cancer Res. 6: 3312-3318.

Structure-function analyses on mammalian HSF1 located the HSE DNA-binding domain to the N terminus of the HSF1 polypeptide. Further C-terminal are 4-3 hydrophobic repeats (or 4-3 leucine zippers) HR-A and HR-B that play critical roles in trimerization as well as in the regulation of trimerization of the factor. Following these repeats is a region known as "regulatory domain" that modulates the transcriptional activity of the factor. This domain contains a binding site for HSP90 complex as well as at least two sites for activating phosphorylation. C-terminal of this region is another 4-3 hydrophobic repeat, HR-C, that plays a critical role in maintaining (unactivated) HSF1 in a non-homotrimeric state. Towards the C-terminal end of the HSF1 polypeptide are located two transcription activation domains. Voellmy, R. (2006) Handb. Exp. Pharmacol. 172: 43-68. HSF1 has a modular nature. When the DNA-binding domain of human HSF1 was replaced with a DNA-binding domain from bacterial protein LexA, the resulting chimeric factor LexA$_{87}$-hHSF1$_{79}$ was non-homotrimeric and inactive in the absence of heat or stress, but could be induced by heat or other stress to homotrimerize as well as to transactivate a reporter gene under the control of a LexA-responsive promoter. Zuo et al. (1994) Mol. Cell. Biol. 14: 7557-7568; Zuo et al. (1995) Mol. Cell. Biol. 15: 4319-4330.

A complete structure of an HSF1 molecule was not available when the work disclosed herein was initiated. However, eleven crystal structures of the HSF DNA-binding domain, 9 from yeast and 2 from *Drosophila*, had been deposited in the Brookhaven Protein Databank at the time. (Structures of the human HSF1 and HSF2 DNA-binding domains became available only very recently.) Based on the former structures, a comparative model of adequately high quality could be generated of the DNA-binding domain of human HSF1. This model predicted four potential binding cavities (cavities A-D). Nine appropriate 3-point pharmacophores were defined. Using these pharmacophores, a proprietary library (Leadbuilder NICE) of about 300,000 commercially available drug-like molecules was searched, and a biased sublibrary of about 2,000 compounds was assembled.

For screening this sublibrary, a cell-based assay was developed. We opted for a cell-based assay, because a cell-free assay would have had to be a DNA-binding assay. Such an assay would have limited discovery to molecules capable of interfering with the DNA-binding function of HSF1. This was thought to be too narrow a focus, considering that three of the four cavities identified in the HSF1 DNA-binding domain are not near the DNA interaction region. A straightforward cell-based assay, in which a HSF1-responsive gene would be assayed, was considered likely to be over-inclusive. Compounds would be scored as hits that inhibit any factor that is involved in HSF1 activation or prevents HSF1 deactivation. These factors include protein kinases, activators of protein phosphatases, factors affecting HSF1 mRNA stability, HSP90, HDAC6, etc. For developing a more discriminating cell-based assay, advantage was taken of the modular nature of HSF1. As discussed above, replacement of the HSF1 DNA-binding domain with an unrelated DNA-binding domain (bacterial LexA) resulted in a chimeric transcription factor whose activity is regulated like that of wild type HSF1 but that binds to a different target promoter. The cell-based assay developed (see below for the particular format employed) compared transactivation by wild type HSF1 and chimeric HSF1 in cells exposed to an HSF1-activating heat treatment in the presence of a sublibrary compound. A compound was scored as a hit, if it inhibited the activity of wild type HSF1 but not of chimeric HSF1.

The cell-based assay made use of HeLa-derived cell line Z74 that stably contains a gene for chimeric transcription factor LexA-(human) HSF1 under the control of a CMV early promoter, a firefly luciferase (fluc) gene driven by a promoter responsive to the latter chimeric transcription factor and a *Renilla* luciferase (rluc) gene functionally linked to an hsp70b promoter and therefore controlled by endogenous HSF1 (FIG. 1A). As is shown in FIGS. 1B & C, the reporter genes responded similarly to heat dose, i.e., their activation depended on both duration of heat exposure and temperature of the exposure. These data demonstrated that transcription factors LexA-HSF1 and (endogenous) wild type HSF1 are similarly stress-regulated in the Z74 cell line. Depletion of HSF1 (and LexA-HSF1) by siRNA supported the notion that this stress regulation is mediated by HSF1 (and LexA-HSF1). Therefore, the Z74 line was well suited for use in a screening assay aimed at discovering molecules that inhibit heat-induced HSF1 activity through interaction with the transcription factor's DNA-binding domain.

Figure 2:
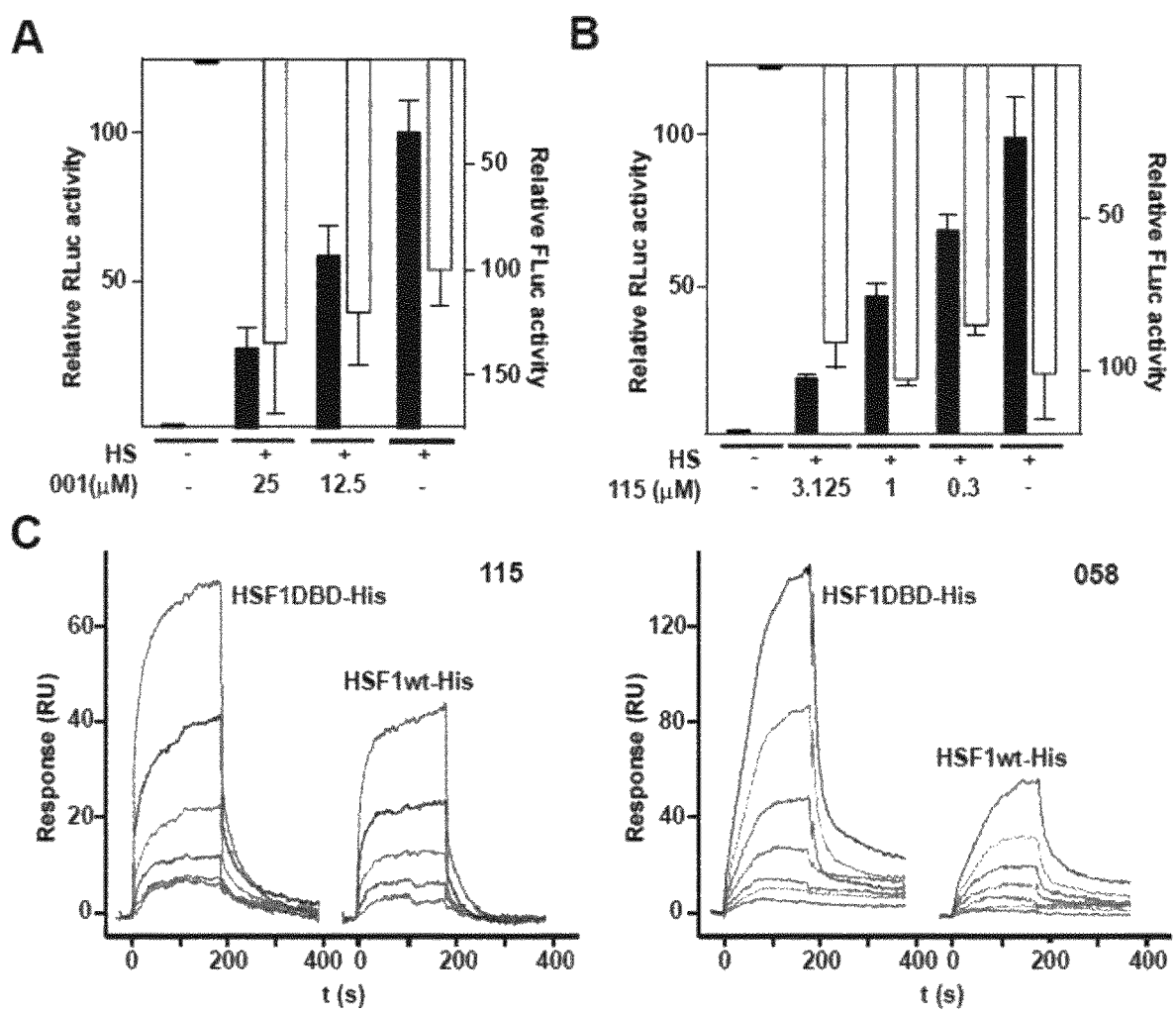
FIG. 2. (A) Inhibition of RLuc expression by $I_{HSF}$ 001 in Z74 cells. Cultures were mock-exposed (−) or exposed to increasing concentrations of the $I_{HSF}$ and, 2 hours later, were heated (HS) at 43° C. for 30 min. RLuc (black bars) and FLuc activities were measured 6 hours after HS. Relative activities are shown. (B) Inhibition of RLuc expression by $I_{HSF}$ 115 in Z74 cells. (C) SPR sensorgrams indicating concentration-dependent binding of $I_{HSF}$ 058 and $I_{HSF}$ 115 to recombinant His-tagged human HSF1 (HSF1wt-His) and His-tagged HSF1 DNA-binding domain fragment (HSF1DBD-His). Responses shown are to 500, 250, 125, 62.5, 31.3 and 15.6 µM $I_{HSF}$ 115, and to 250, 125, 62.5, 31.3, 15.6, 7.81 and 3.91 µM $I_{HSF}$ 058, respectively.

The compounds of the afore-mentioned biased sublibrary were screened in cell line Z74 at 12.5 and 25 µM concentrations. Typically, Z74 cultures in 96-well plates were exposed to compound or vehicle for 2 h, heat-treated at 43.0° C. for 30 min, and incubated further for 6 h at 37° C. to allow for accumulation of the luciferases. RLuc and FLuc activities were determined, typically using the Dual-Glo® Luciferase Assay System (Promega Corp., Madison, Wis.), and reading luciferase light counts in a Wallac Microbeta Trilux-1450 Luminometer (PerkinElmer, Waltham, Mass.). I$_{HSF}$ 001 was one of two library compounds that inhibited RLuc expression but not FLuc expression in heat-treated Z74 cells (Table 1; FIG. 2A). Therefore, I$_{HSF}$ 001 is an inhibitor of HSF1 function that specifically acts through the HSF1 DNA-binding domain. I$_{HSF}$ 001 fulfills the pharmacophoric criteria for a cavity A binder. A corroborating experiment utilized a cell line containing an hsp70b promoter-driven fluc gene. I$_{HSF}$ 001 was found to inhibit FLuc expression in this line (data not shown). I$_{HSF}$ 001 is (E)-ethyl 4-oxo-4-(thiazol-2-ylamino)but-2-enoate. The compound can be obtained from commercial sources (e.g., AKE-PB-90340538, Akos).

To determine structure-activity relationships as well as to improve upon the inhibitory activity of $I_{HSF}$ 001, a series of related compounds was synthesized and tested for activity using the above-described cell-based assay. The structure of some of these compounds and their inhibitory activities are presented in Table 2. The compounds were prepared from known starting materials using chemical methods known to the skilled artisan and further described in the example section. The most potent $I_{HSF}$ was compound 115 that had substantial activity in the high nanomolar range in the Z74-based screening assay (Table 2; FIG. 2B).

TABLE 1

Inhibition of HSF1 activity in Z74 cells ($I_{HSF}$ 001 tested at 25 μM)

| $I_{HSF}$ | Structure | Experiment No. | Inhibition of HSF1 activity [RLuc] (%) | Inhibition of LexA-hHSF activity [FLuc] (%) |
|---|---|---|---|---|
| 001 | (thiazol-2-ylamino ethyl fumarate structure) | 1 | 66 | 3 |
| | | 2 | 69 | 0 |
| | | 3 | 69 | 0 |
| | | 4 | 67 | 0 |
| | | 5 | 68 | 0 |
| | | 6 | 63 | 0 |
| | | 7 | 56 | 0 |
| | | 8 | 51 | 0 |
| | | 9 | 45 | 15 |

TABLE 2

Inhibition of HSF1 activity in Z74 cells

| $I_{HSF}$ | Structure | Inhibition of HSF1 activity at 25 μM $I_{HSF}$ [RLuc] (%) | Inhibition of HSF1 activity at 12.5 μM $I_{HSF}$ [RLuc] (%) | IC$_{50}$ (μM) |
|---|---|---|---|---|
| 001 | (thiazol-2-ylamino ethyl fumarate structure) | 64 +/− 6 | 37 +/− 9 | 17.8 +/− 2.6 |
| 010 | (benzothiazol-2-ylamino ethyl fumarate structure) | 56 | 56 | ND |
| 011 | (4-methylthiazol-2-ylamino ethyl fumarate structure) | 83 | 69 | 7.0 |
| 012 | (4-phenylthiazol-2-ylamino ethyl fumarate structure) | 86 | 68 | 11.3 |

TABLE 2-continued

Inhibition of HSF1 activity in Z74 cells

| $I_{HSF}$ | Structure | Inhibition of HSF1 activity at 25 μM $I_{HSF}$ [RLuc] (%) | Inhibition of HSF1 activity at 12.5 μM $I_{HSF}$ [RLuc] (%) | IC$_{50}$ (μM) |
|---|---|---|---|---|
| 013 | 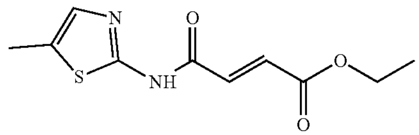 [SMILES: CCOC(=O)/C=C/C(=O)Nc1ncc(C)s1] | 50 | 34 | 25.0 |
| 014 | 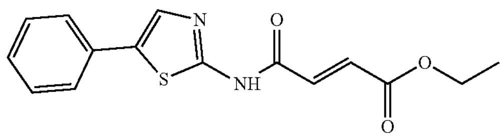 [SMILES: CCOC(=O)/C=C/C(=O)Nc1ncc(-c2ccccc2)s1] | 89 | 60 | 7.1 |
| 015 | 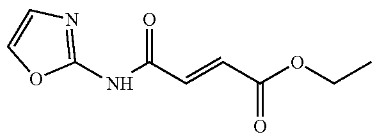 | 20 | 0 | ND |
| 016 | 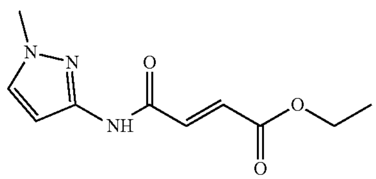 [SMILES: CCOC(=O)/C=C/C(=O)Nc1ccn(C)n1] | 25 | 0 | ND |
| 017 | 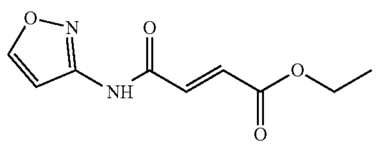 | 37 | 32 | ND |
| 018 | 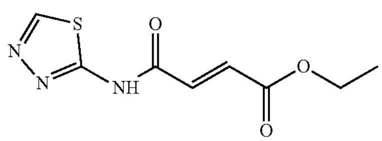 | 53 | 20 | 23.6 |
| 020 | 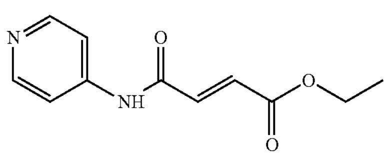 [SMILES: CCOC(=O)/C=C/C(=O)Nc1ccncc1] | 53 | 30 | 23.5 |
| 027 | 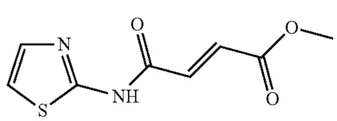 | 42 | 18 | >25 |
| 028 | 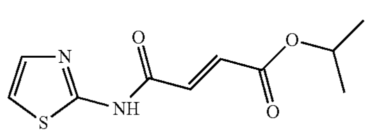 [SMILES: CC(C)OC(=O)/C=C/C(=O)Nc1nccs1] | 41 | 13 | >25 |
| 030 | 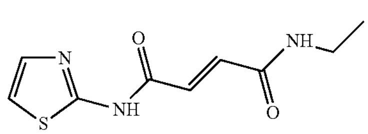 | 18 | 5 | >25 |

TABLE 2-continued

Inhibition of HSF1 activity in Z74 cells

| $I_{HSF}$ | Structure | Inhibition of HSF1 activity at 25 μM $I_{HSF}$ [RLuc] (%) | Inhibition of HSF1 activity at 12.5 μM $I_{HSF}$ [RLuc] (%) | $IC_{50}$ (μM) |
|---|---|---|---|---|
| 031 | 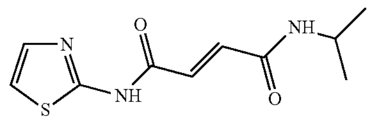 [SMILES: CC(C)NC(=O)/C=C/C(=O)Nc1nccs1] | 24 | 15 | ND |
| 042 | 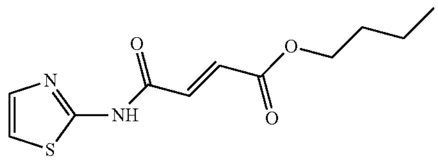 [SMILES: CCCCOC(=O)/C=C/C(=O)Nc1nccs1] | 52 | 1 | ND |
| 043 | 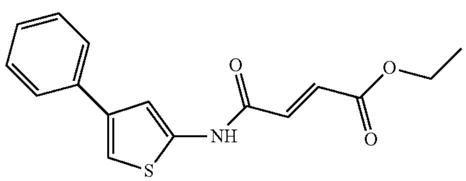 [SMILES: CCOC(=O)/C=C/C(=O)Nc1cc(-c2ccccc2)cs1] | 5 | 32 | ND |
| 045 | 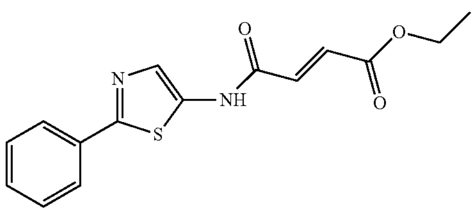 [SMILES: CCOC(=O)/C=C/C(=O)Nc1cnc(-c2ccccc2)s1] | 53 | 34 | ND |
| 046 | 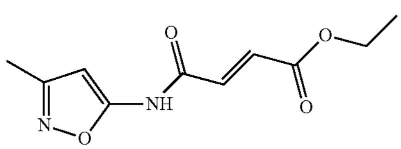 [SMILES: CCOC(=O)/C=C/C(=O)Nc1cc(C)no1] | 70 | 33 | ND |
| 048 | 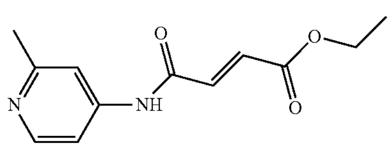 [SMILES: CCOC(=O)/C=C/C(=O)Nc1ccnc(C)c1] | 67 | 37 | ND |
| 049 | 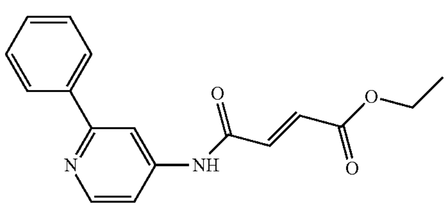 [SMILES: CCOC(=O)/C=C/C(=O)Nc1ccnc(-c2ccccc2)c1] | 85 | 53 | ND |
| 050 | 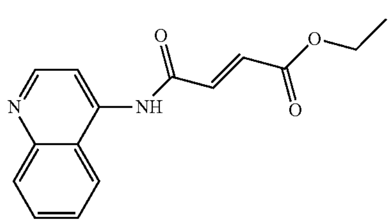 [SMILES: CCOC(=O)/C=C/C(=O)Nc1ccnc2ccccc12] | 61 | 40 | ND |

TABLE 2-continued

Inhibition of HSF1 activity in Z74 cells

| $I_{HSF}$ | Structure | Inhibition of HSF1 activity at 25 μM $I_{HSF}$ [RLuc] (%) | Inhibition of HSF1 activity at 12.5 μM $I_{HSF}$ [RLuc] (%) | IC$_{50}$ (μM) |
|---|---|---|---|---|
| 051 | 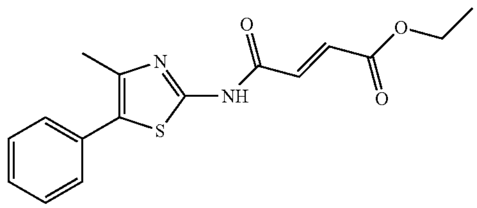 [SMILES: CCOC(=O)/C=C/C(=O)Nc1nc(C)c(-c2ccccc2)s1] | 92 | 72 | 9.6 |
| 052 | 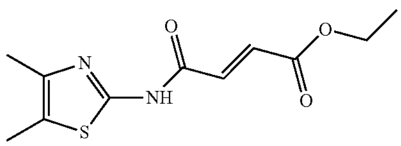 [SMILES: CCOC(=O)/C=C/C(=O)Nc1nc(C)c(C)s1] | 71 | 57 | 7.4 |
| 053 | 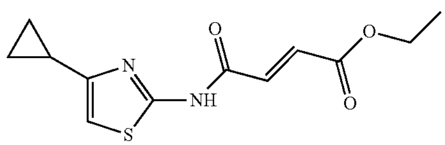 [SMILES: CCOC(=O)/C=C/C(=O)Nc1nc(C2CC2)cs1] | 29 | 15 | >25 |
| 054 | 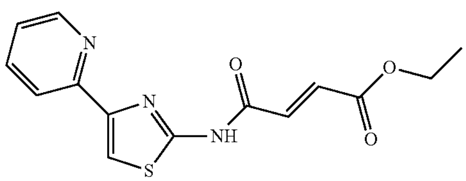 [SMILES: CCOC(=O)/C=C/C(=O)Nc1nc(-c2ccccn2)cs1] | 69 | 22 | 20.2 |
| 055 | 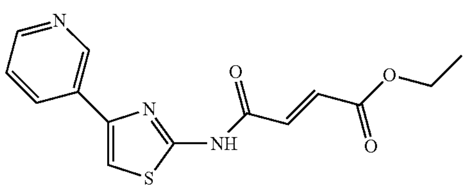 [SMILES: CCOC(=O)/C=C/C(=O)Nc1nc(-c2cccnc2)cs1] | 74 | 27 | 18.7 |
| 056 | 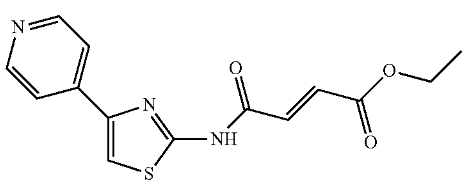 [SMILES: CCOC(=O)/C=C/C(=O)Nc1nc(-c2ccncc2)cs1] | 61 | 35 | 19.8 |
| 057 | 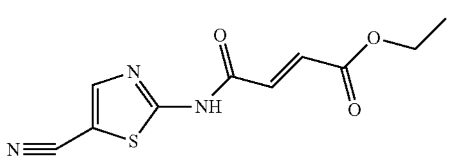 [SMILES: CCOC(=O)/C=C/C(=O)Nc1ncc(C#N)s1] | 65 | 40 | ND |
| 058 | 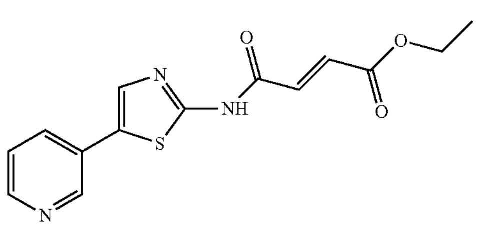 [SMILES: CCOC(=O)/C=C/C(=O)Nc1ncc(-c2cccnc2)s1] | 97 +/- 2 | 79 +/- 7 | 4.8 +/- 0.4 |

TABLE 2-continued

Inhibition of HSF1 activity in Z74 cells

| $I_{HSF}$ | Structure | Inhibition of HSF1 activity at 25 μM $I_{HSF}$ [RLuc] (%) | Inhibition of HSF1 activity at 12.5 μM $I_{HSF}$ [RLuc] (%) | IC$_{50}$ (μM) |
|---|---|---|---|---|
| 059 | 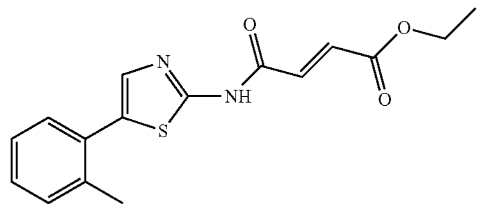 [SMILES: CCOC(=O)/C=C/C(=O)Nc1ncc(-c2ccccc2C)s1] | 72 | 45 | 14.7 |
| 060 | 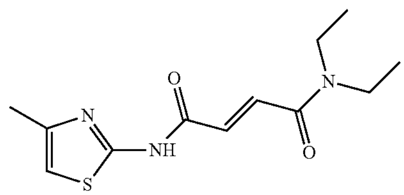 [SMILES: CCN(CC)C(=O)/C=C/C(=O)Nc1nc(C)cs1] | 19 | 16 | ND |
| 061 | 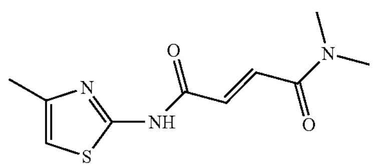 | 18 | 12 | ND |
| 070 | 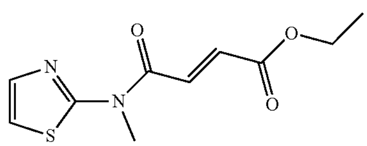 [SMILES: CCOC(=O)/C=C/C(=O)N(C)c1nccs1] | 90 +/− 8 | 72 +/− 7 | 5.7 +/− 0.8 |
| 076 | 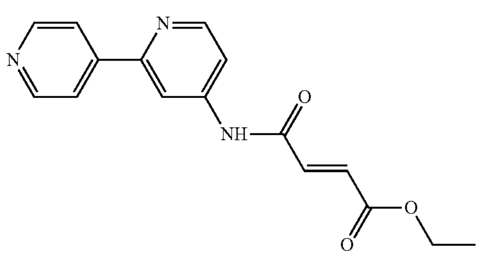 [SMILES: CCOC(=O)/C=C/C(=O)Nc1ccnc(-c2ccncc2)c1] | 66 | 56 | ND |
| 077 | 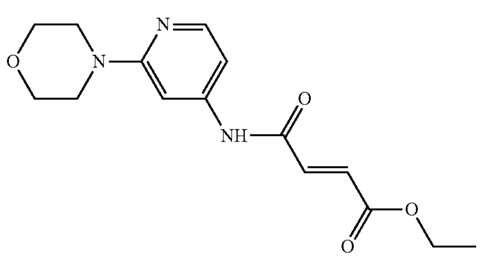 [SMILES: CCOC(=O)/C=C/C(=O)Nc1ccnc(N2CCOCC2)c1] | 67 | 42 | ND |

TABLE 2-continued
Inhibition of HSF1 activity in Z74 cells
| $I_{HSF}$ | Structure | Inhibition of HSF1 activity at 25 μM $I_{HSF}$ [RLuc] (%) | Inhibition of HSF1 activity at 12.5 μM $I_{HSF}$ [RLuc] (%) | $IC_{50}$ (μM) |
|---|---|---|---|---|
| 078 | 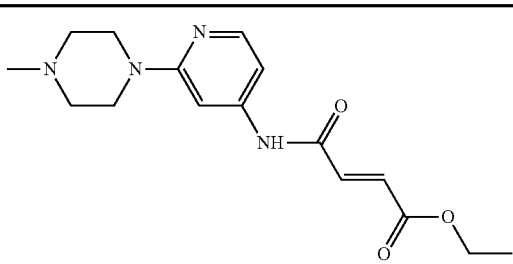 | 54 | 32 | ND |
| 079 | 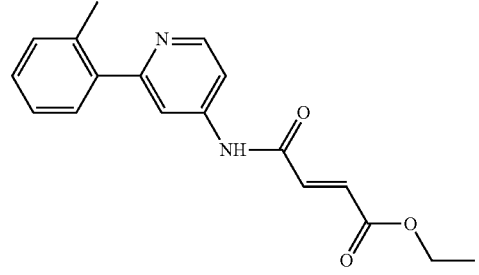 [SMILES: CCOC(=O)/C=C/C(=O)Nc1ccnc(-c2ccccc2C)c1] | 79 | 42 | ND |
| 080 | 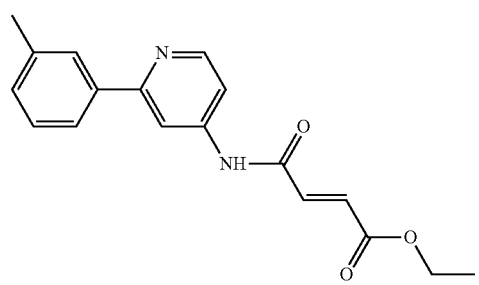 [SMILES: CCOC(=O)/C=C/C(=O)Nc1ccnc(-c2cccc(C)c2)c1] | 71 | 55 | ND |
| 081 | 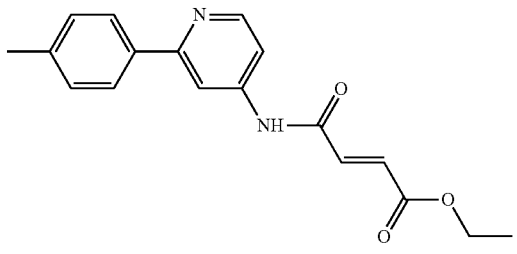 [SMILES: CCOC(=O)/C=C/C(=O)Nc1ccnc(-c2ccc(C)cc2)c1] | 65 | 42 | ND |
| 082 | 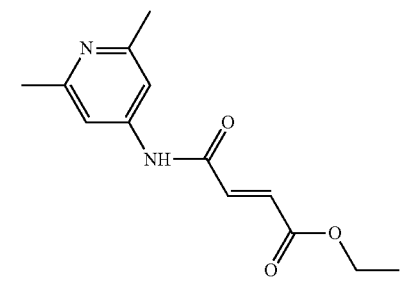 [SMILES: CCOC(=O)/C=C/C(=O)Nc1cc(C)nc(C)c1] | 91 | 58 | ND |

TABLE 2-continued

Inhibition of HSF1 activity in Z74 cells

| $I_{HSF}$ | Structure | Inhibition of HSF1 activity at 25 μM $I_{HSF}$ [RLuc] (%) | Inhibition of HSF1 activity at 12.5 μM $I_{HSF}$ [RLuc] (%) | IC$_{50}$ (μM) |
|---|---|---|---|---|
| 083 | 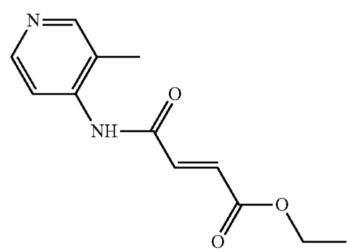 [SMILES: CCOC(=O)/C=C/C(=O)Nc1ccncc1C] | 34 | 24 | ND |
| 086 | 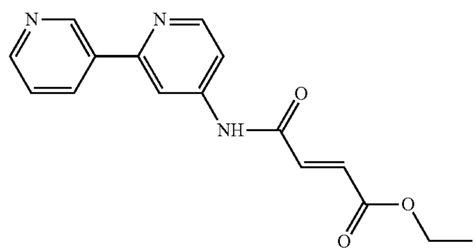 [SMILES: CCOC(=O)/C=C/C(=O)Nc1ccnc(-c2cccnc2)c1] | 78 | 47 | ND |
| 088 | 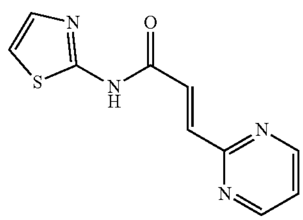 [SMILES: O=C(/C=C/c1ncccn1)Nc1nccs1] | 31 | 25 | >25 |
| 089 | 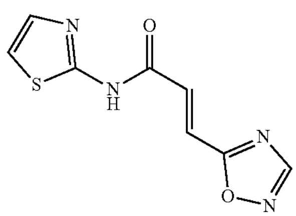 [SMILES: O=C(/C=C/c1ncno1)Nc1nccs1] | 61 | 41 | 17.9 |
| 090 | 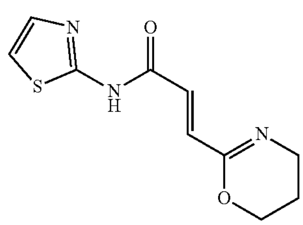 [SMILES: O=C(/C=C/C1=NCCCO1)Nc1nccs1] | 98 +/− 2 | 78 +/− 19 | 5.4 +/− 0.4 |
| 091 | 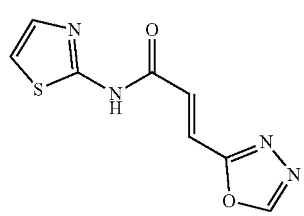 [SMILES: O=C(/C=C/c1nnco1)Nc1nccs1] | 27 | 22 | >25 |

TABLE 2-continued

Inhibition of HSF1 activity in Z74 cells

| $I_{HSF}$ | Structure | Inhibition of HSF1 activity at 25 μM $I_{HSF}$ [RLuc] (%) | Inhibition of HSF1 activity at 12.5 μM $I_{HSF}$ [RLuc] (%) | IC$_{50}$ (μM) |
| --- | --- | --- | --- | --- |
| 092 | 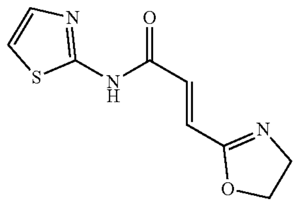 [SMILES: O=C(/C=C/C1=NCCO1)Nc1nccs1] | 99 +/- 1 | 90 +/- 6 | 4.7 +/- 0.2 |
| 095 | 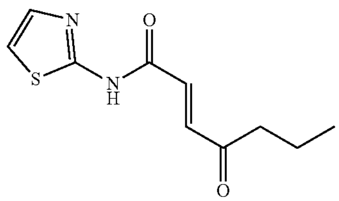 | 44 | 6 | >25 |
| 099 | 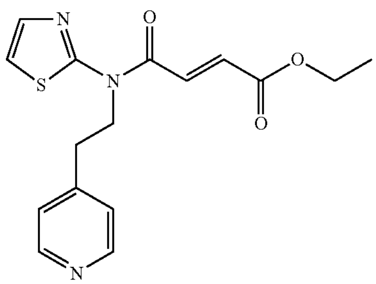 [SMILES: CCOC(=O)/C=C/C(=O)N(CCc1ccncc1)c1nccs1] | 95 | 17 | 18.0 |
| 101 | 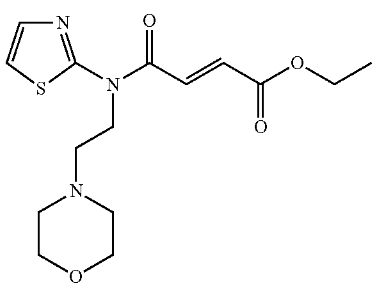 [SMILES: CCOC(=O)/C=C/C(=O)N(CCN1CCOCC1)c1nccs1] | 48 | -30* | >25 |
| 105 | 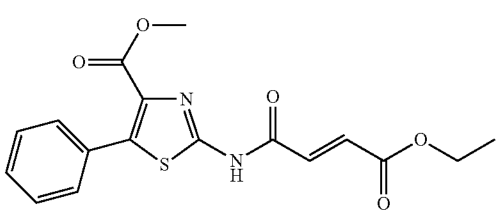 [SMILES: CCOC(=O)/C=C/C(=O)Nc1nc(C(=O)OC)c(-c2ccccc2)s1] | 96 | 69 | 10.8 |
| 107 | 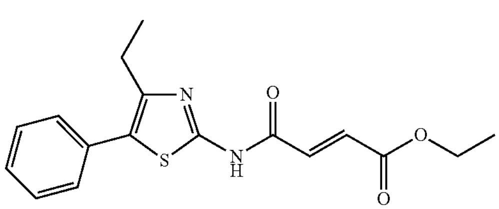 [SMILES: CCOC(=O)/C=C/C(=O)Nc1nc(CC)c(-c2ccccc2)s1] | 92 | 62 | 10.6 |

TABLE 2-continued

Inhibition of HSF1 activity in Z74 cells

| $I_{HSF}$ | Structure | Inhibition of HSF1 activity at 25 μM $I_{HSF}$ [RLuc] (%) | Inhibition of HSF1 activity at 12.5 μM $I_{HSF}$ [RLuc] (%) | IC$_{50}$ (μM) |
|---|---|---|---|---|
| 108 | 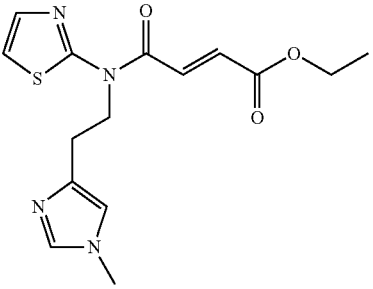 [SMILES: CCOC(=O)/C=C/C(=O)N(CCc1cn(C)cn1)c1nccs1] | 89 | −6* | 19.6 |
| 109 | 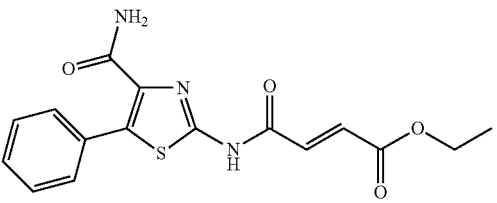 [SMILES: CCOC(=O)/C=C/C(=O)Nc1nc(C(N)=O)c(-c2ccccc2)s1] | 88 | 53 | 11.2 |
| 112 | 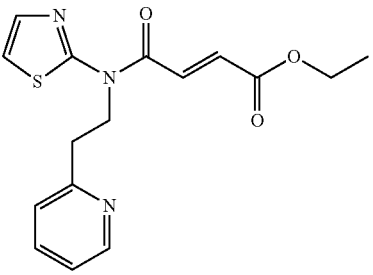 [SMILES: CCOC(=O)/C=C/C(=O)N(CCc1ccccn1)c1nccs1] | 26 | 13 | >25 |
| 115 | 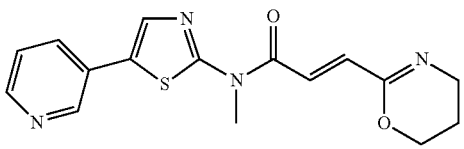 [SMILES: CN(C(=O)/C=C/C1=NCCCO1)c1ncc(-c2cccnc2)s1] | 100+/− | 99 +/− 1 | 0.7 +/− 0.1 |

*Compound enhanced rLuc activity.
ND: not determined.

Based on experimental results obtained with the compounds shown in Table 2 as well as a multitude of other related compounds that were made and tested for their inhibitory activity, an HSF inhibitor can be defined as a compound of formulae I or II below,

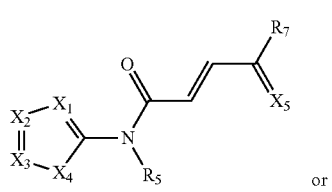

Formula I

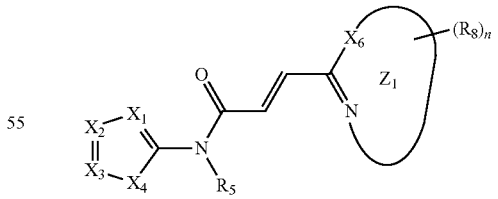

Formula II wherein
n is 0-8, preferably 0-4 (0, 1, 2, 3 or 4); o is 0, 1, 2, 3 or 4;
p is 0, 1 or 2;
$X_1$ is N or C(—$R_1$);
$X_2$ is C(—$R_2$), N, or O or S (double bond between $X_3$ and $X_4$ instead of between $X_2$ and $X_3$);
$X_3$ is C(—$R_3$) or N;

$X_4$ is S or O, or C(—$R_4$) or N if $X_2$ is O or S (double bond between $X_3$ and $X_4$ instead of between $X_2$ and $X_3$);

$X_5$ is O, S or N(—$R_6$);

$X_6$ is O, S, N, NH, ($C_1$-$C_4$)alkylN, CH or C(($C_1$-$C_4$)alkyl), $CH_2$ or CH(($C_1$-$C_4$)alkyl)$^{or}$ C(($C_1$-$C_4$)alkyl)$_2$;

$R_1$ is H, halo, ($C_1$-$C_4$)alkyl; halo($C_1$-$C_4$)alkyl, H being preferred;

$R_2$, $R_3$, $R_5$ and $R_8$ are independently selected, and each can be H or any substituent, provided that its presence is compatible with the small molecule nature of the inhibitor and, statistically, no more than 10% of any ionizable group it may contain is ionized at neutral pH ($R_8$ not being a substituent of $X_6$);

whereby $R_2$ and $R_3$ can form a substituted or unsubstituted 5 to 8 membered aromatic or non-aromatic ring or heterocycle as exemplified by formulae I A and I B below:

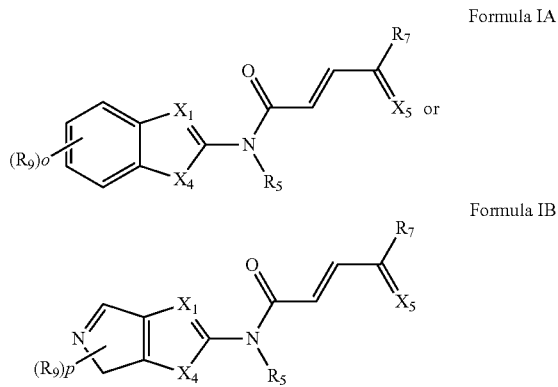

Formula IA

Formula IB $R_4$ is H, halo, ($C_1$-$C_4$)alkyl; halo($C_1$-$C_4$)alkyl, H being preferred;

$R_6$ is H or is selected from halogen, OH, SH, $NH_2$ and $Z_2$, whereby $Z_2$ is a residue comprising from 1 to 4 carbon atoms; $R_7$ is —OH, —SH, —$NH_2$, —O—$Z_2$, —S—$Z_2$, —NH—$Z_2$ or —N—($Z_2$)$_2$;

$R_9$ is independently selected from (H), alkenyl, alkoxy, alkoxyalkyl, alkoxyalkynyl, alkoxycarbonyl, alkoxycarbonylalkyl, alkoxy-NH.dbd.C(alkyl)-, alkyl, alkylcarbonyl, alkylcarbonylalkyl, alkylcarbonyloxy, alkylsulfonyl, alkylthio, alkynyl, aryl, arylalkoxy, arylalkyl, arylcarbonyl, aryloxy, cyano, cyanoalkyl, cycloalkyl, cycloalkylalkyl, formyl, halogen, haloalkyl, hydroxy, hydroxyalkyl, hydroxycycloalkyl, mercapto, nitro, oxo, phenyl, and $R_{ss}R_{tt}N$—, $R_{ss}R_{tt}N$ carbonyl, $R_{ss}R_{tt}N$ alkyl, wherein $R_{ss}$ and $R_{tt}$ are each independently selected from the group consisting of hydrogen, alkyl, alkylcarbonyl, alkoxycarbonyl, and alkylSO$_2$—;

and $Z_1$ is a 5-8 membered heterocycle.

In alternative embodiments, substituents $R_2$, $R_3$, and $R_5$ in formula I or $R_2$, $R_3$, $R_5$ and $R_8$ in formula II (or in any of formulae III-XII in which one or more of these substituents are indicated) are independently selected from the group consisting of (H), hydroxy, formyl, alkylcarbonyl, alkoxy, alkylthio, alkylthioalkyl, alkoxyalkoxy, alkoxycarbonyl, alkoxyalkenyl, alkoxyalkynyl, alkoxycarbonyl-alkoxy, alkyl, alkenyl, alkenyloxy, alkenylthio, alkynyl, alkynylthio, cycloalkyl, cycloalkylthio, cycloalkylalkoxy, cycloalkylalkylthio, cycloalkenylalkoxy, cycloalkenylalkylthio, alkylSO$_2$—, acryl, arylalkyl, aryloxy, arylthio, arylalkenyl, arylalkynyl, arylcarbonyl, arylalkoxycarbonyl, heteroaryl, heterocycle, heterocyclealkyl, heterocyclealkenyl, heterocyclealkoxy, heterocyclealkylthio, heterocyclealkynyl, hetero- cyclecarbonyl, heterocycleoxycarbonyl, cyano, cyanoalkyl, cyanoalkoxy, cyanoalkylthio, cyanoalkynyl, cyanoalkenyl, cyanoalkenylalkoxy, cyanoalkenylalkylthio, halogen, haloalkyl, trihaloalkyl, trihaloalkoxy, hydroxyalkyl, hydroxyalkenyl, hydroxyalkynyl, hydroxyalkoxy, hydroxyalkylthio, dihydoxyalkoxy, dihydoxyalkylthio, nitro, $R_f$—O—, $R_f$—S—, HO—N=CH—(CH2)$_{0, 1\ or\ 2}$-, $R_aR_bN$—, $R_aR_b$Nalkyl-, $R_aR_b$Nalkenyl-, $R_aR_b$Nalkynyl-, $R_aR_b$NC(O)—, $R_aR_b$NC(O)alkynyl-, $R_aR_b$NC(O)alkoxy-, $R_aR_b$NSO$_2$alkoxy-, and $R_w$—O—N=CH—, wherein alkyl may be optionally substituted with O= and $R_tN$=; $R_a$ and $R_b$ are each individually selected from the group consisting of hydrogen, alkyl, alkenyl, alkenylcarbonyl, alkylsulfonyl, alkylcarbonyl, alkoxycarbonyl, alkoxycarbonylalkyl, alkoxycarbonylalkylcarbonyl, alkynyl, aryl, arylalkyl, arylalkenyl, arylcarbonyl, aryloxycarbonyl, arylalkyloxycarbonyl, heteroaryl, heterocycle, heterocyclealkyl, heterocyclealkenyl, heterocyclecarbonyl, heterocyclealkylcarbonyl, haloalkyl, trihaloalkyl, trihaloalkylcarbonyl, haloalkylcarbonyl, heterocycleoxycarbonyl hydroxyalkyl, and hydroxyalkylcarbonyl; $R_t$ is selected from the group consisting of hydrogen, alkyl and HO—; $R_f$ is selected from the group consisting of alkyl, cycloalkyl, cycloalkylalkyl, alkoxyalkyl, alkylthioalkyl, and haloalkyl; R, is selected from the group consisting of hydrogen, alkylcarbonyl-NH-alkyl-NHC(O)-alkyl, alkyl, alkyl(alkyl)N-alkyl-NHC(O)-alkyl, hydroxyalkyl-NHC(O)-alkyl, heterocyclealkyl-NHC(O)-alkyl, heterocycle-NHC(O)-alkyl, and heteroarylalkyl-NHC(O)-alkyl.

In further alternative embodiments, substituents $R_2$, $R_3$, and $R_5$ in formula I or $R_2$, $R_3$, $R_5$ and $R_8$ in formula II (or in any of formulae III XII in which one or more of these substituents are indicated) are independently selected from the group consisting of (H), hydroxy, formyl, alkylcarbonyl, alkoxy, alkylthio, alkylthioalkyl, alkoxyalkoxy, alkoxycarbonyl, alkoxyalkenyl, alkoxyalkynyl, alkoxycarbonylalkoxy, alkyl, alkenyl, alkenyloxy, alkynyl, cycloalkyl, cycloalkylalkoxy, cycloalkenylalkoxy, alkylSO$_2$—, acryl, arylalkyl, aryloxy, arylalkenyl, arylalkynyl, arylcarbonyl, arylalkoxycarbonyl, heteroaryl, heterocycle, heterocyclealkyl, heterocyclealkenyl, heterocyclecarbonyl, heterocyclealkylcarbonyl, haloalkyl, trihaloalkyl, trihaloalkylcarbonyl, haloalkylcarbonyl, heterocycleoxycarbonyl hydroxyalkyl, and hydroxyalkylcarbonyl; $R_t$ is selected from the group consisting of hydrogen, alkyl and HO—; $R_f$ is selected from the group consisting of alkyl, cycloalkyl, cycloalkylalkyl, alkoxyalkyl, alkylthioalkyl, and haloalkyl; R, is selected from the group consisting of hydrogen, alkylcarbonyl-NH-alkyl-NHC(O)-alkyl, alkyl, alkyl(alkyl)N-alkyl-NHC(O)-alkyl, hydroxyalkylNHC(O)-alkyl, heterocyclealkyl-NHC(O)-alkyl, heterocycle-NHC(O)-alkyl, and heteroarylalkylNHC(O)-alkyl.

Preferably (not applicable to $R_{10}$-$R_{13}$), $R_5$ is selected from H, $(C_1-C_4)$alkyl, aromatic heterocycle$(C_1-C_4)$alkyl and non-aromatic heterocycle$(C_1-C_4)$alkyl. Among the most preferred $R_5$ substituents is $CH_3$. Preferably, $R_8$ is selected from H, halogen, halo$(C_1-C_4)$alkyl, $(C_1-C_4)$alkyl, $OCH_3$, OH, $NH_2$, $N(CH_3)_2$, —CN, —$(C_2-C_4)$alkyl-, and —$U(C_1-C_3)$alkyl-, wherein U is $CH_2$, O, S, NH or $NCH_3$. $R_8$ can also form a 5- or 6-membered aromatic or non-aromatic cycle or heterocycle, incorporating two adjacent methylene groups of Z1. Most preferably, $R_8$ is H, halo, $(C_1-C_4)$alkyl or halo$(C_1-C_4)$alkyl.

In alternative embodiments, substituents $R_6$ and $Z_2$ in formula I or in any of formulae III, V and VII are independently selected from H ($R_6$ only), $(C_1-C_4)$alkyl, $(C_1-C_4)$alkenyl, $(C_1-C_4)$alkynyl, $(C_1-C_4)$alkoxy, $(C_1-C_4)$alkenyloxy, $(C_1-C_4)$alkynyloxy, mercapto, $(C_1-C_4)$alkylthio, $(C_1-C_4)$alkenylthio, $(C_1-C_4)$alkynylthio, $(C_1-C_4)$alkylNH—, $(C_1-C_4)$alkenylNH—, $(C_1-C_4)$alkynylNH—, $(C_1-C_3)$alkylN$(C_1-C_3)$alkyl, $(C_1-C_3)$alkyl$((C_1-C_3)$alkyl)N—, $(C_1-C_2)$alkyl$((C_1-C_2)$alkyl)N$(C_1-C_2)$alkyl-, formyl, halo, halo$(C_1-C_4)$alkyl, halo$(C_1-C_4)$alkenyl, halo$(C_1-C_4)$alkynyl, halo$(C_1-C_4)$alkoxy, halo $(C_1-C_4)$alkenyloxy, halo $(C_1-C_4)$alkynyloxy, hydroxy$(C_1-C_4)$alkyl, hydroxy$(C_1-C_4)$alkenyl, and hydroxy$(C_1-C_4)$alkynyl.

In more specific embodiments, an HSF inhibitor can be defined as a compound according to formulae III or IV presented below,

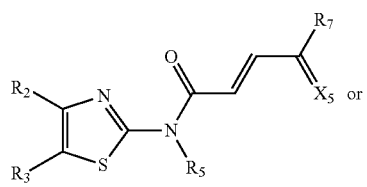

Formula III

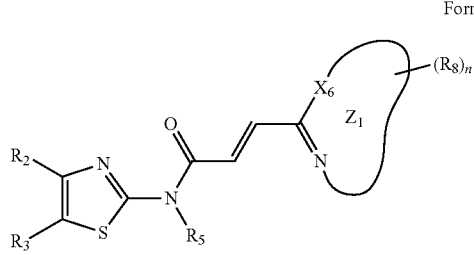

Formula IV wherein n, $R_2$, $R_3$, $R_5$, $R_6$, $R_7$, $R_8$, $X_5$, $X_6$, $Z_1$ and $Z_2$ are as defined before for the inhibitors of formulae I and II, respectively.

In yet more specific embodiments, an HSF inhibitor can be defined as a compound according to formulae V or VI, Formula V

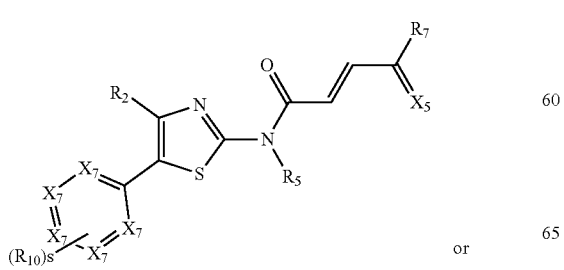

or

Formula VI

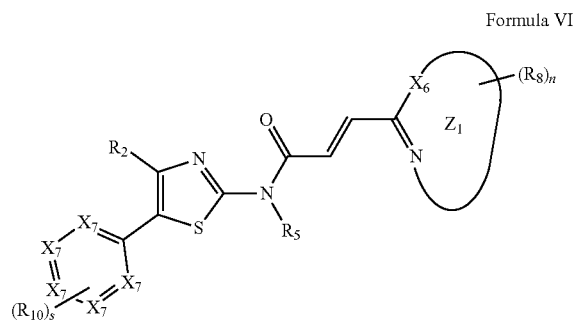

wherein n, $R_2$, $R_5$, $R_6$, $R_7$, $R_8$, $X_5$, $X_6$, $Z_1$ and $Z_2$ are as provided before. $X_7$ is CH or N (or C(—$R_{10}$)). Preferably, 3 or less of the $X_7$ are N, and most preferably only one of the $X_7$ is N; $R_{10}$ is defined as $R_5$ and s is 0, 1, 2, 3 or 4.

More particularly, an HSF inhibitor can be defined as a compound according to formulae VII or VIII, Formula VII

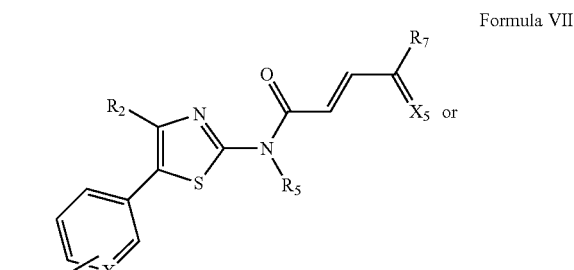

Formula VIII

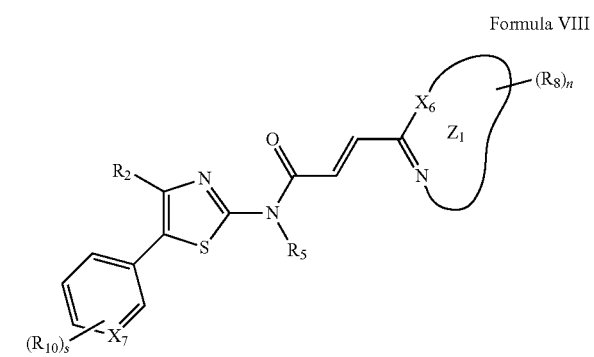

wherein n, s, $R_2$, $R_5$, $R_6$, $R_7$, $R_8$, $R_{10}$, $X_5$, $X_6$, $X_7$, $Z_1$ and $Z_2$ are as provided before.

Alternatively, an HSF inhibitor can be defined as a compound according to formulae IX or X below, Formula IX

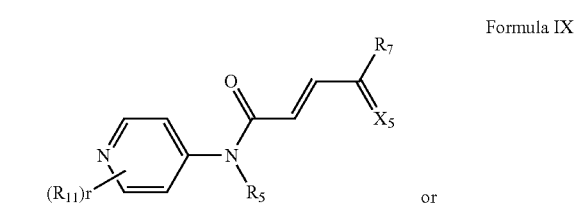

or

Formula X

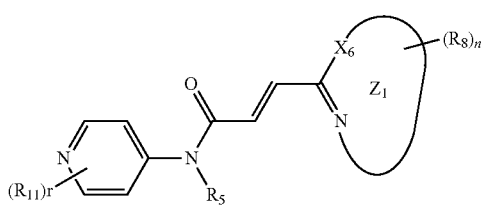

wherein n, $R_5$, $R_6$, $R_7$, $R_8$, $X_5$, $X_6$, $Z_1$ and $Z_2$ are as defined before, r is 0-4 and $R_{11}$ is defined as $R_5$.

More particularly, an HSF inhibitor can be defined as a compound according to formulae XI or XII below, wherein n, $R_5$, $R_6$, $R_7$, $R_8$, $X_5$, $X_6$, $Z_1$ and $Z_2$ are as previously defined; o is 0, 1, 2, 3 or 4; $R_{12}$ and $R_{13}$ are as $R_5$; and $X_8$ is CH or N. Preferably, 3 or less of the $X_8$ are N, and most preferably only one $X_8$ is N.

Formula XI

Formula XII

Specific compounds of formulae I to XII include, but are not limited to:

(E)-ethyl 4-oxo-4-(thiazol-2-ylamino)but-2-enoate
(E)-ethyl 4-(benzo[d]thiazol-2-ylamino)-4-oxobut-2-enoate
(E)-ethyl 4-((4-methylthiazol-2-yl)amino)-4-oxobut-2-enoate
(E)-ethyl 4-oxo-4-((4-phenylthiazol-2-yl)amino)but-2-enoate
(E)-ethyl 4-((5-methylthiazol-2-yl)amino)-4-oxobut-2-enoate
(E)-ethyl 4-oxo-4-((5-phenylthiazol-2-yl)amino)but-2-enoate
(E)-ethyl 4-(oxazol-2-ylamino)-4-oxobut-2-enoate
(E)-ethyl 4-((1-methyl-1H-pyrazol-3-yl)amino)-4-oxobut-2-enoate
(E)-ethyl 4-(isoxazol-3-ylamino)-4-oxobut-2-enoate
(E)-ethyl 4-((1,3,4-thiadiazol-2-yl)amino)-4-oxobut-2-enoate
(E)-ethyl 4-oxo-4-(pyridine-4-ylamino)but-2-enoate
(E)-methyl 4-oxo-4-(thiazol-2-ylamino)but-2-enoate
(E)-isopropyl 4-oxo-4-(thiazol-2-ylamino)but-2-enoate
$N^1$-ethyl-$N^4$-(thiazol-2-yl)fumaramide
$N^1$-isopropyl-$N^4$-(thiazol-2-yl)fumaramide
Ethyl 3-(thiazol-2-ylcarbamoyl)benzoate
(E)-butyl 4-oxo-4-(thiazol-2-ylamino)but-2-enoate
(E)-ethyl 4-oxo-4-((4-phenylthiophen-2-yl)amino)but-2-enoate
(E)-ethyl 4-oxo-4-((2-phenylthiazol-5-yl)amino)but-2-enoate
(E)-ethyl 4-((3-methylisoxazol-5-yl)amino)-4-oxobut-2-enoate
(E)-ethyl 4-((2-methylpyridin-4-yl)amino)-4-oxobut-2-enoate
(E)-ethyl 4-oxo-4-((2-phenylpyridin-4-yl)amino)but-2-enoate
(E)-ethyl 4-oxo-4-(quinolin-4-ylamino)but-2-enoate
(E)-ethyl 4-((4-methyl-5-phenylthiazol-2-yl)amino)-4-oxobut-2-enoate
(E)-ethyl 4-((4,5-dimethylthiazol-2-yl)amino)-4-oxobut-2-enoate
(E)-ethyl 4-((4-cyclopropylthiazol-2-yl)amino)-4-oxobut-2-enoate
(E)-ethyl 4-oxo-4-((4-(pyridin-2-yl)thiazol-2-yl)amino)but-2-enoate
(E)-ethyl 4-oxo-4-((4-(pyridin-3-yl)thiazol-2-yl)amino)but-2-enoate
(E)-ethyl 4-oxo-4-((4-(pyridine-4-yl)thiazol-2-yl)amino)but-2-enoate
(E)-ethyl 4-((5-ethynylthiazol-2-yl)amino)-4-oxobut-2-enoate
(E)-ethyl 4-oxo-4-((5-(pyridine-3-yl)thiazol-2-yl)amino)but-2-enoate
(E)-ethyl 4-oxo-4-((5-(o-tolyl)thiazol-2-yl)amino)but-2-enoate
$N^1$, $N^1$-diethyl-$N^4$-(4-methylthiazol-2-yl)fumaramide
$N^1$, $N^1$-dimethyl-$N^4$-(4-methylthiazol-2-yl)fumaramide
(E)-ethyl 4-(methyl(thiazol-2-yl)amino)-4-oxobut-2-enoate
Ethyl 2-(thiazol-2-ylamino)thiazol-5-carboxylate
(E)-ethyl 4-4([2,4'-bipyridin]-4-ylamino)-4-oxobut-2-enoate
(E)-ethyl 4-((2-morpholinopyridin-4-yl)amino)-4-oxobut-2-enoate
(E)-ethyl 4-((2-(4-methylpiperazin-1-yl)pyridine-4-yl)amino)-4-oxobut-2-enoate
(E)-ethyl 4-oxo-4-((2-(o-tolyl)pyridine-4-yl)amino)but-2-enoate
(E)-ethyl 4-oxo-4-((2-(m-tolyl)pyridine-4-yl)amino)but-2-enoate
(E)-ethyl 4-oxo-4-((2-(p-tolyl)pyridine-4-yl)amino)but-2-enoate
(E)-ethyl 4-((2,6-dimethylpyridin-4-yl)amino)-4-oxobut-2-enoate
(E)-ethyl 4-((3-methylpyridin-4-yl)amino)-4-oxobut-2-enoate
(E)-ethyl 4-([2,3'-bipyridin]-4-ylamino)-4-oxobut-2-enoate
(E)-3-(pyrimidin-2-yl)-N-(thiazol-2-yl)acrylamide
(E)-3-(1,2,4-oxadiazol-5-yl)-N-(thiazol-2-yl)acrylamide
(E)-3-(5,6-dihydro-4H-1,3-oxazin-2-yl)-N-(thiazol-2-yl)acrylamide
(E)-3-(1,3,4-oxadiazol-2-yl)-N-(thiazol-2-yl)acrylamide
(E)-3-(4,5-dihydrooxazol-2-yl)-N-(thiazol-2-yl)acrylamide
(E)-4-oxo-N-(thiazol-2-yl)hept-2-enamide
(E)-3-(oxazol-2-yl)-N-(thiazol-2-yl)acrylamide
(E)-4-oxo-N-(thiazol-2-yl)hept-2-enamide (E)-ethyl 4-oxo-4-((2-(pyridine-4-yl)ethyl)(thiazol-2-yl) amino)but-2-enoate
(E)-ethyl 4-((morpholinoethyl)(thiazol-2-yl)amino)-4-oxobut-2-enoate
(E)-methyl 2-(4-ethoxy-4-oxobut-2-enamido)thiazol-4-carboxylate
(E)-ethyl 4-((4-ethyl-5-phenylthiazol-2-yl)amino)-4-oxobut-2-enoate
(E)-ethyl 4-((2-(1-methyl-1H-imidazol-4-yl)ethyl)(thiazol-2-yl)amino)-4-oxobut-2-enoate
(E)-ethyl 4-((4-carbamoylthiazol-2-yl)amino)-4-oxobut-2-enoate
(E)-ethyl 4-oxo-4-((pyridin-2-yl)ethyl)(thiazol-2-yl)amino) but-2-enoate
(E)-3-(5,6-dihydro-4H-[1,3]oxazin-2-yl)-N-methyl-N-(5-(pyridin-3-yl-thiazol-2-yl) acrylamide.

The HSF inhibitors of the present disclosure may be prepared by a number of methods well known to those skilled in the art, including, but not limited to those described in the example section, or through modifications of these methods by applying standard techniques known to those skilled in the art of organic synthesis. All processes disclosed in association with the present disclosure are contemplated to be practiced at any scale, including milligram, gram, multigram, kilogram, multikilogram or commercial industrial scale.

The present disclosure is meant to also encompass pharmaceutically acceptable derivatives or prodrugs of the HSF inhibitors described herein. Such pharmaceutically acceptable derivatives or prodrugs may be designed to enhance biological properties such as oral absorption, clearance, metabolism or compartmental distribution. Such derivations are well known in the art. As the skilled practitioner will recognize, the compounds of this disclosure may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

Further Characterization of Selected HSF Inhibitors $I_{HSF}$ 001 was included in the sublibrary as a compound that satisfied the parametric values of pharmacophore A4 modeled to fit the largest predicted cavity of the human HSF1 DNA-binding domain (cavity A). Because this cavity is far removed from the presumed DNA interaction region, compound 001 and its analogs were not expected to be capable of directly interfering with the binding of DNA to the HSF1 DNA-binding domain. However, they may affect DNA binding indirectly, if their binding altered the conformation of the HSF1 DNA-binding domain. Alternatively, or in addition, the compounds may interfere with homo-oligomerization of HSF1 or the binding of co-factors. Initial experiments had shown that certain compounds including $I_{HSF}$ 001 had apparent effects on HSF1 DNA-binding, whereas others compounds did not. We selected $I_{HSF}$ 058 and 115 for further characterization. $I_{HSF}$ 058 appeared to affect HSF1 DNA binding (but see the discussion below), whereas $I_{HSF}$ 115 did not. Direct interactions between the $I_{HSF}$ and HSF1 were detected by surface plasmon resonance (SPR). Recombinant full-length human HSF1 or a recombinant DNA-binding domain fragment of human HSF1 served as ligands. The SPR sensorgrams in FIG. 2C demonstrate that both $I_{HSF}$ 058 and $I_{HSF}$ 115 interacted in a dose-dependent fashion with full-length HSF1 as well as with the HSF1 DNA-binding domain fragment. Interactions were detected at compound concentrations of 15.6 µM and higher. These results demonstrate that the compounds are capable of directly binding the HSF1 DNA-binding domain. However, the compound concentrations at which direct interactions were observed were higher than those that caused inhibition of induced RLuc expression in Z74 cells. There are several factors that may account for this difference in sensitivity. One such factor may be the limited aqueous solubility of $I_{HSF}$ 058 and 115 that may have negatively affected the interaction experiments. Recombinant HSF1 or its DNA-binding domain fragment may not possess native conformations (or may be limited to conformations that support interactions with the $I_{HSF}$ less well than other conformations that occur in the cell). They lack posttranslational modifications and are not associated, as HSF1 is in its cellular environment, with multichaperone complexes and/or other co-factors. Moreover, immobilization of recombinant HSF1 and HSF1 DNA-binding fragment on a sensor chip may have further impaired their respective conformations (or limited their conformational flexibility), further jeopardizing their ability to interact with the $I_{HSF}$.

Figure 3:
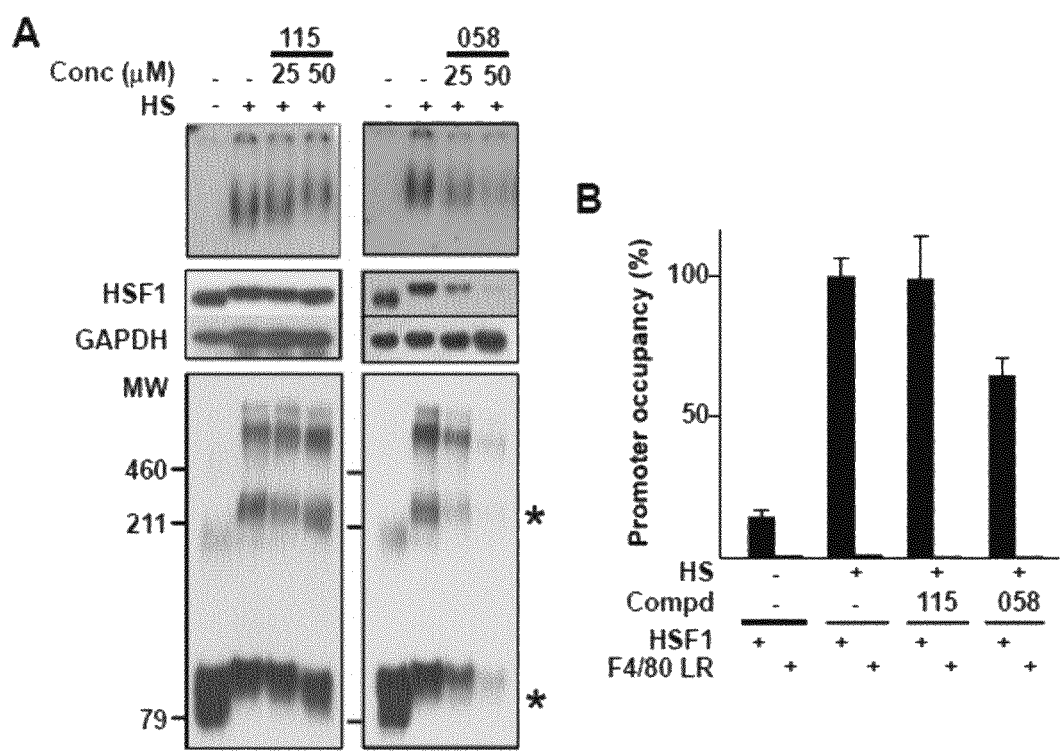
FIG. 3. (A) HeLa cell cultures were mock-treated (−) or exposed for 2 hours to the indicated concentrations of compounds 058 or 115 and then heat-treated (HS) at 43° C. for 30 min. Top panels: HSF1 DNA-binding activities in cell extracts were determined by EMSA. The panels show the major HSF1-HSE DNA probe complexes. Middle panels: HSF1 levels assayed by western blot (WB). GAPDH served as a loading control. Bottom panels: HSF1 homooligomerization. Aliquots of extracts were EGS-treated and then analyzed by anti-HSF1 WB. The positions of pre-stained molecular weight marker proteins (MW, in thousands) are indicated to the right. Asterisks indicate the positions of monomeric and trimeric HSF1, respectively. (B) Relative occupancy of the hspa1a promoter was assessed by chromatin immunoprecipitation assay of HeLa cell cultures mock-treated (−) or treated with compounds 058 or 115 at 12.5 µM concentrations for 2 hours and then heat-treated (HS) at 43° C. for 30 min. Chromatin fragments were immunoprecipitated using HSF1 antibodies or an F4/80 LR (control) antibody, and associated hspa1a promoter DNA was quantified by real-time PCR.

Electrophoretic mobility shift assays (EMSA) using a radiolabeled HSE DNA probe were carried out to assess HSF1 DNA-binding activity in extracts of heat-treated (43° C./30 min) HeLa cells that had been exposed to different concentrations of compounds 058 or 115 (FIG. 3A, top panels). Exposure to $I_{HSF}$ 058 at 25 or 50 µM concentrations resulted in important reductions in heat-induced DNA-binding activity. $I_{HSF}$ 115 failed to have a similar effect on DNA-binding activity. Anti-HSF1 western blot (WB) of the same extracts revealed reduced levels of HSF1 in the cells that had been exposed to $I_{HSF}$ 058 (FIG. 3A, middle panels), indicating that the compound had induced degradation of HSF1. $I_{HSF}$ 115 did not affect HSF1 levels. HSF1 degradation correlated well with the observed decrease in DNA-binding activity. Therefore, HSF1 degradation provides a sufficient explanation for the reduced HSE DNA-binding activity in cells treated with $I_{HSF}$ 058. We conclude that compound 058 does not impair the DNA-binding ability but the stability of HSF1. EMSA were also carried out using extracts of HeLa cells that had been heat-treated at 43° C. for 30 min. In these assays, no reduction of HSE DNA-binding activity was observed in the presence of $I_{HSF}$ 001, 011, 049, 050, 051, 052, 057 or 059 at concentrations as high as about 0.5 mM.

We also investigated whether the compounds were capable of interfering with HSF1 oligomerization. Aliquots of the extracts were subjected to cross-linking with EGS (ethylene glycolbis(succinimidylsuccinate)) and then re-analyzed by anti-HSF1 WB. No impairment of oligomerization could be observed (FIG. 3A, bottom panels). $I_{HSF}$ 058-induced degradation of HSF1 was observed again in this analysis. Chromatin immunoprecipitation experiments were conducted to find out whether the $I_{HSF}$ could affect HSF1 DNA binding in vivo. In one such experiment, cultures of HeLa cells were exposed for two hours to 12.5 µM $I_{HSF}$ 058 or 115, respectively, or to vehicle (FIG. 3B). The cultures were subsequently heat-treated and then processed using a routine procedure. DNA fragments were co-precipitated by HSF1 antibodies, and a promoter segment of the hspa1a gene including the gene-proximal HSE sequence and the TATA box sequence was amplified by real-time PCR. Results indicated that HSF1 occupancy of the hspa1a promoter was not reduced substantially in cells that had been exposed to $I_{HSF}$ 115, indicating that the inhibitor of HSF1 also did not affect in vivo HSF1 DNA binding. The effect seen with $I_{HSF}$ 058 was ascribed to the aforementioned HSF1 destabilization.

Figure 4:
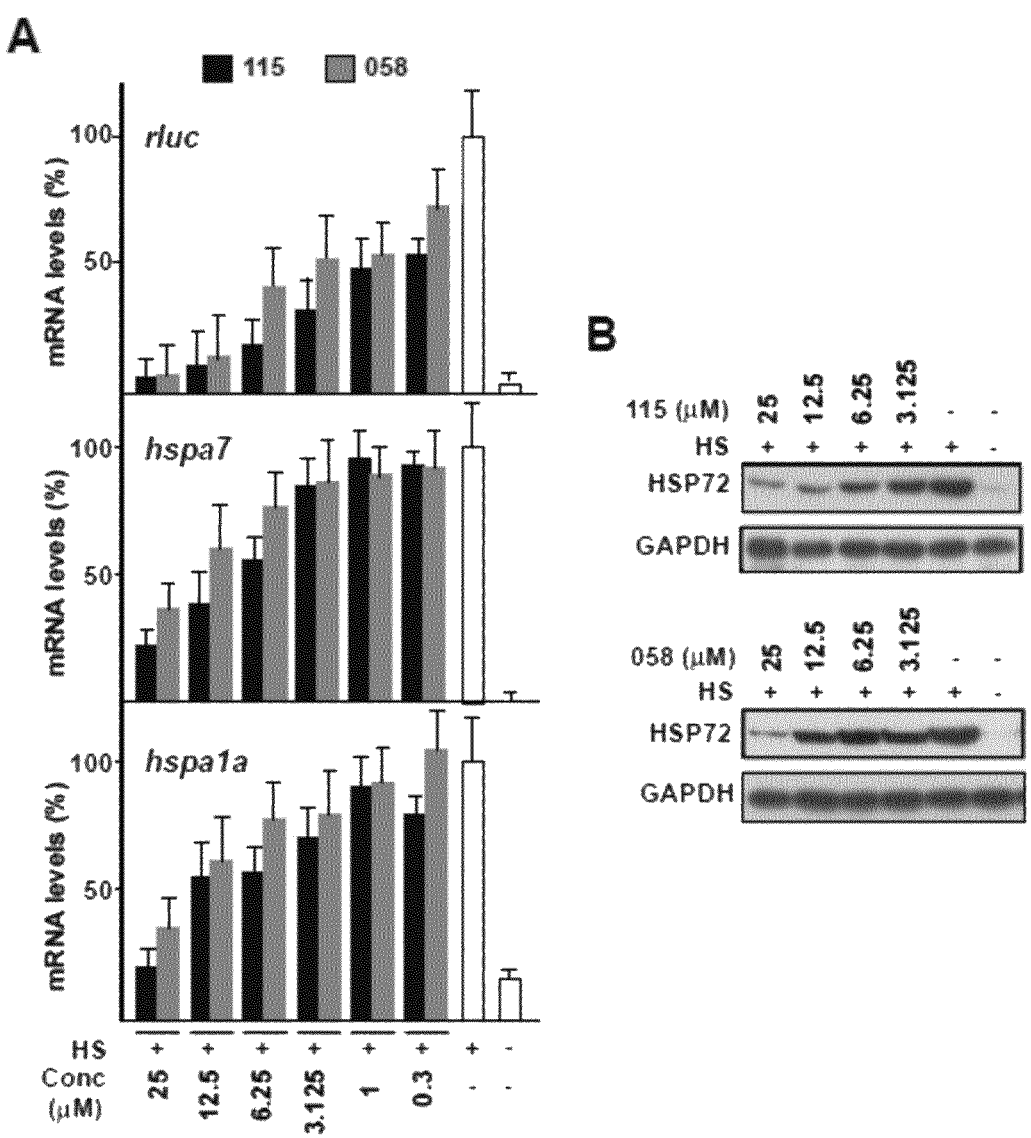
FIG. 4. (A) rluc, hspa7 and hspa1a mRNA levels in Z74 cells mock-exposed (−) or exposed to the indicated concentrations of compounds 058 or 115 for 2 hours, heat-treated (HS) at 43° C. for 30 min and post-incubated for one hour at 37° C. mRNA levels were quantified by reverse transcription-real-time PCR. (B) HSP72 levels in HeLa cells mock-exposed (−) or exposed to the indicated concentrations of compounds 058 or 115 for 2 hours, heat-treated (HS) at 43° C. for 30 min and post-incubated for 6 hours at 37° C. HSP72 levels were estimated by HSP72 WB. GAPDH levels served as "loading controls".

To assess the transcriptional effects of the $I_{HSF}$, cultures of Z74 cells were exposed for two hours to $I_{HSF}$ 058 or $I_{HSF}$ 115 at different concentrations, or to vehicle. Following heat treatment and a one-hour post-incubation at 37° C., extracts were prepared, and polyadenylated rluc, hsp70b (hspa7) and hspa1a RNA was quantified by reverse transcription and real-time PCR. Exposure to the compounds resulted in a dose-dependent reduction of transcript levels of the hsp70b/hspa7 promoter-driven rluc gene (FIG. 4A, top panel). $I_{HSF}$ 115 had somewhat more important effects than $I_{HSF}$ 058. It is noted that rluc mRNA levels were already substantially reduced at 1 µM concentrations of the $I_{HSF}$ These data appear to reflect the true effects of the $I_{HSF}$ on heat-induced hsp promoter-driven gene transcription. We tend to discount the possibility that the latter data report effects on transcript stability. After all, the compounds were designed to bind to HSF1 and were found to do so. Nothing suggests that the $I_{HSF}$ could also interact with transcripts of HSF1 target genes. Dose-dependent inhibitory effects on transcript accumulation were also observed for the hspa1a and hspa7 (hsp70b) genes, although the latter genes appeared to be somewhat less sensitive to the $I_{HSF}$ than the hsp70b/hspa7-rluc gene, perhaps owing to compensatory mechanism(s) (FIG. 4A, lower panels).

Effects of the $I_{HSF}$ could also be demonstrated at the level of heat-induced accumulation of inducible Hsp70 (mainly products of the hspa1a and hspa1b genes). WB experiments (FIG. 4B) reported detectable inhibitory effects of $I_{HSF}$ 115 at 3.125 µM and more substantial effects at 6.25 µM. $I_{HSF}$ 058 was less effective than $I_{HSF}$ 115.

Recruitment of HSF1 to target promoters in response to a stress is mediated by ATF1/CREB. Takii, R. et al. (2015) Mol. Cell. Biol. 35: 11-25. ATF1/CREB regulates the stress-induced HSF1 transcription complex that includes BRG1 chromatin-remodeling complex and p300/CBP. The former complex promotes an active chromatin state in the promoters, whereas p300/CBP accelerates the shutdown of HSF1 DNA-binding activity as well as stabilizes HSF1 against proteasomal degradation during recovery from stress. To assess the effects of the $I_{HSF}$ on the assembly of the transcription complex, use was made of a HeLa-derived cell line that stably expresses a C-terminally FLAG-tagged HSF1. Cultures were heat-treated for 30 min at 43° C. in the presence or absence of $I_{HSF}$ 115, extracts were prepared, and tagged HSF1 was immunoprecipitated using an anti-FLAG antibody. WB analysis of immunoprecipitates revealed that $I_{HSF}$ 115 dramatically reduced the HSF1-ATF1 interaction. These findings strongly suggested that $I_{HSF}$ 115 interferes with the formation of ATF1-based transcription complexes that are instrumental in heat-induced transcription of HSF1 target genes.

HSF Inhibitors Reduce the Viability of a Wide Range of Cancer Cells

Figure 5:
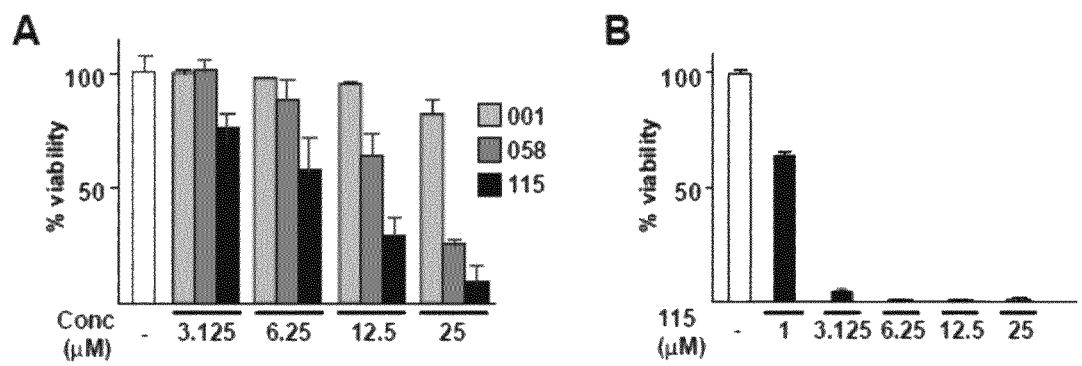
FIG. 5. (A) Viability of HeLa cell cultures mock-exposed (−) or exposed to the indicated concentrations of compounds 001, 058 or 115. (B) Viability of MM.1S cells mock-exposed (−) or exposed to the indicated concentrations of compound 115. Viability was assayed after 96 hours of exposure using an Alamar Blue assay.

Cultures of HeLa cells were exposed for 96 hours to different concentrations of $I_{HSF}$ 001, 058 and 115, and viability was assessed using an Alamar Blue assay. It is noted that this standard assay examines attached cells only. This subject will be discussed in more detail below. Viability decreased in a dose-dependent fashion (FIG. 5A). Compound 115 was considerably more effective than compound 058, which in turn was more effective than compound 001. The relative cytotoxicity of the compounds appears to parallel their respective activities as inhibitors of HSF1 function (inhibition of RLuc expression in Z74 cells). We next examined the viability of different human cancer cell lines subsequent to a 96-hour exposure to compound 115 (Table 3). HSF1 was reported as being required for optimal p21 expression and for p53-mediated cell cycle arrest in response to genotoxins. Logan, I. R. et al. (2009) Nucleic Acids Res. 37: 2962-2971. These findings suggest that HSF1 may also play a p53-dependent pro-apoptotic function. Cell lines of different p53 status were included in the experiments in order to find out whether sensitivity to $I_{HSF}$ 115 was related to p53 status. Exposure to $I_{HSF}$ 115 reduced viability in all cell lines tested, although their sensitivity to the compound varied greatly. A comparison of moderately sensitive HeLa cells and highly sensitive multiple myeloma MM.1S cells is shown in FIGS. 5 A & B. Complete loss of viability of MM.1S cells occurred at 6.25 µM $I_{HSF}$ 115, in some experiments already at 3.125 µM. No effect of p53 status could be discovered. It is noted that a number of additional HSF inhibitors of the present disclosure were tested and found to effectively reduce the viability of human cancer cells.

Figure 6:
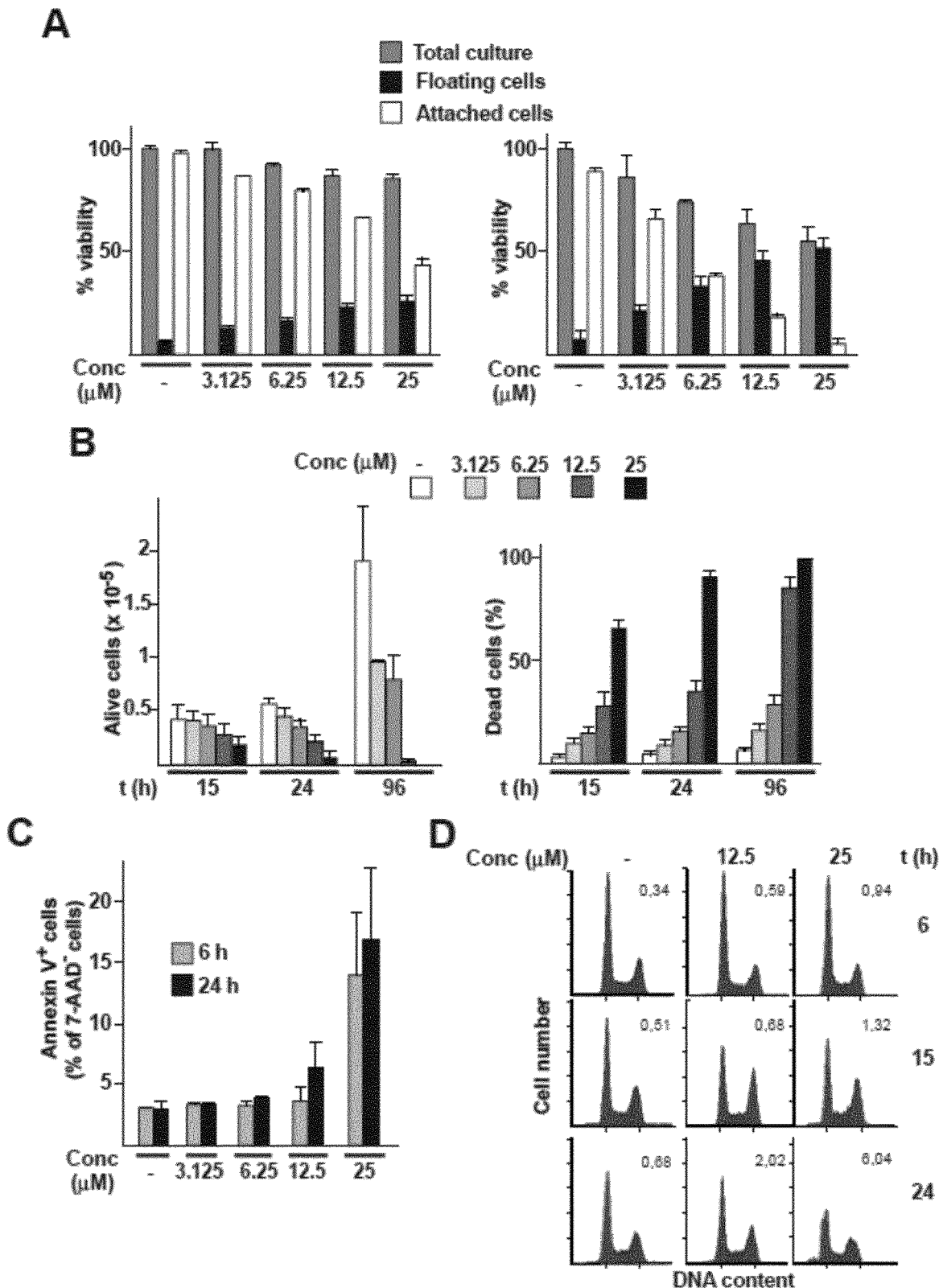
FIG. 6. (A) HeLa cell cultures were mock-exposed (−) or exposed to the indicated concentrations of compound 115 for 24 (left panel) or 96 (right panel) hours. Cell viability of total cultures, floating cells and attached cells was assayed using an Alamar Blue assay. (B) HeLa cell cultures were mock-exposed (−) or exposed to the indicated concentrations of compound 115 for 15-96 hours. Trypan Blue dye exclusion was employed to determine numbers of live cells (left panel) and relative levels of necrotic cells (right panel). (C) HeLa cell cultures were mock-exposed (−) or exposed to the indicated concentrations of compound 115 for 6 and 24 h. Shown are relative levels of early apoptotic cells (annexin-positive, 7 aminoactinomycin D-negative). (D) Flow cytometric analysis of DNA of HeLa cell cultures mock-exposed (−) or exposed to the indicated concentrations of compound 115 for 6, 15 and 24 hours. Relative levels of apoptotic cells are indicated.

Further studies were aimed at finding out whether $I_{HSF}$-exposed cancer cells were only growth-arrested or were actually killed and, if they were killed, by what mechanism. In one type of experiment, parallel sets of HeLa cell cultures were exposed for either 24 or 96 hours to different concentrations of $I_{HSF}$ 115. The first set was assayed for viability by the Alamar Blue assay without prior removal of floating cells. Attached and floating cells were assayed separately in the second set; floating cells were subsequently re-plated and incubated for 72 hours without compound. Cells were found to detach from the plates in a $I_{HSF}$ concentration-dependent fashion (FIG. 6A). The viability signal (in whole cultures and, more dramatically, when only attached cells were analyzed) decreased as a function of $I_{HSF}$ concentration. Most floating cells were incapable of re-attaching in the absence of compound (not shown); apparently, these cells had died. More profound effects were observed after 96 hours (right panel) than after 24 hours of exposure (left panel). Hence, the HeLa cells were killed by $I_{HSF}$ 115 in a concentration- and exposure time-dependent fashion. In a different type of experiment, sets of HeLa cell cultures that had been exposed to $I_{HSF}$ 115 for 15, 24 and 96 hours were stained with Trypan Blue. Stained (necrotic) and unstained (live) cells were counted (FIG. 6B). $I_{HSF}$ 115 caused numbers of live cells to decrease and numbers of necrotic cells to increase in a concentration- and time-dependent fashion. An increase in necrotic cells was already apparent after a 15-hour exposure to 3.125 µM $I_{HSF}$ 115. HeLa cells exposed to $I_{HSF}$ 115 appeared to die by a non-apoptotic mechanism. A cytometric analysis of HeLa cells exposed to 12.5 or 25 µM $I_{HSF}$ 115 for up to 24 h revealed only minor sub-G0/G1 fractions (6% or less of cells included) (FIG. 6D). In an annexin V/7 aminoactinomycin D double staining assay on HeLa cells exposed to 25 µM $I_{HSF}$ 115 for up to 24 hours, no more than about 15% of live cells were annexin V-stained (FIG. 6C). A similar analysis was carried out with multiple myeloma MM.1S cells. In contrast to what was found for HeLa cells, the mechanism of cell death of MM.1S cells included a prominent apoptotic component.

TABLE 3

Effectiveness of $I_{HSF}$ 115 in reducing viability of human cancer cell lines - Alamar Blue assay

| Cell line | Cancer | P53 status | EC$_{50}$ (μM) |
|---|---|---|---|
| HeLa | Cervical | Wt | 6.2 |
| BT-20 | Breast | Mut | 8.2 |
| BT-474 | Breast | Mut | 5.2 |
| MCF-7 | Breast | Wt | 5.2 |
| MDA-MB-231 | Breast | Mut | 2.2 |
| T47D | Breast | Mut | 4.4 |
| CAMA-1 | Breast | Mut | 3.5 |
| HCC1143 | Breast | Mut | 4.8 |
| PC-3 | Prostate | Null | 4.0 |
| NCI-H460 | Lung | Wt | 9.4 |
| A549 | Lung | Wt | 18.8 |
| NCI-H3122 | Lung | Wt | 11.0 |
| NCI-H1975 | Lung | Wt | 5.1 |
| NCI-H2228 | Lung | Wt | 12.8 |
| THP-1 | Acute monocytic leukemia | Mut | 6.9 |
| Saos-2 | Osteosarcoma | Null | 8.0 |
| MG-63 | Osteosarcoma | Mut | 4.6 |
| U-2 OS | Osteosarcoma | WT | 5.2 |
| HepG2 | Hepatocellular | Wt | 5.2 |
| MM.1S | Multiple myeloma | Wt | 1.7 |
| IM9 | Multiple myeloma | Wt | 2.3 |
| sNF02.2 | Malignant peripheral nerve sheath | Wt | 8.4 |
| sNF96.2 | Malignant peripheral nerve sheath | Wt | 4.2 |
| SK-OV-3 | Ovarian carcinoma | Mut | 15 |
| SK-N-SH | Neuroblastoma | Wt | 4.0 |
| MNNG/HOS | Osteosarcoma | Mut | 9.2 |
| OV56 | Ovarian carcinoma | Mut | 6.8 |
| PEA1 | Ovarian carcinoma | Mut | 4.1 |
| MDA-MB-453 | Breast | Mut | 4.2 |
| U266B1 | Multiple myeloma | Mut | 3.9 |
| RPMI 8266 | Multiple myeloma | Mut | 3.6 |
| A673 | Ewing's sarcoma | Mut | 1.9 |
| MM.1R | Multiple myeloma | Wt | 1.7 |

Figure 7:
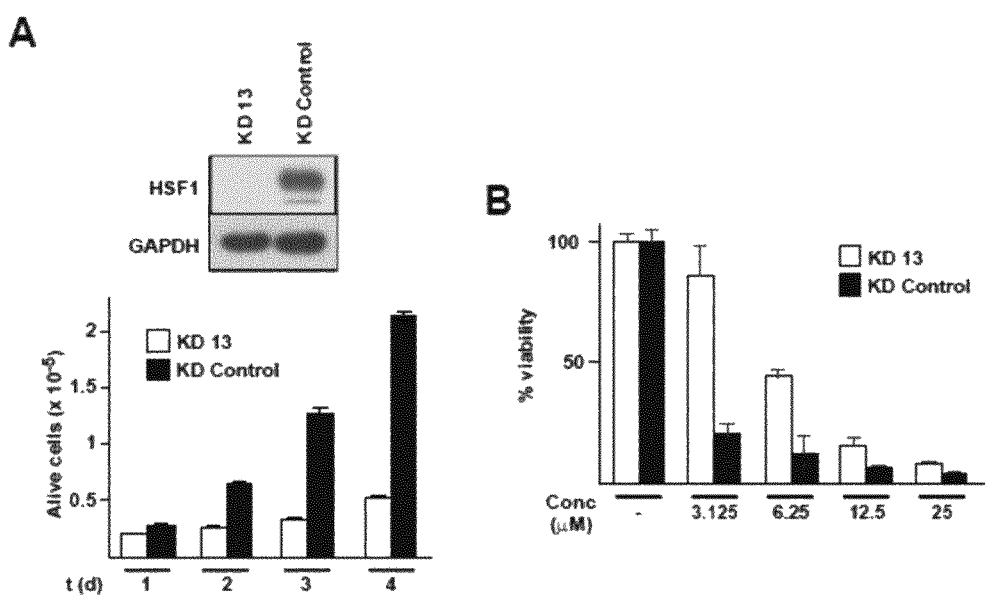
FIG. 7. (A) Upper panel: HSF1 levels in cultures of KD control and KD13 cells as assayed by WB. Lower panel: number of alive KD control and KD13 cells after 1-4 days of culture as determined by Trypan Blue dye exclusion. (B) Viability of KD control and KD13 cells mock-exposed (−) or exposed to the indicated concentrations of compound 115 for 96 h. Cell viability was assayed by Alamar Blue assay.

To obtain evidence that the cytotoxic effect of $I_{HSF}$ 115 is at least in part a consequence of inhibition of HSF1, we transduced HeLa cells with HSF1 siRNA-expressing lentivirus and selected cell lines that exhibited low levels of HSF1. The most severely HSF1-deficient lines grew slowly. FIG. 7 reports on the properties of one such line, KD 13, which was compared to control lentivirus-transduced cells (KD control). The WB in FIG. 7A (upper panel) confirms that the KD 13 line is essentially devoid of HSF1. The lower panel compares growth of the cell line with that of the control cells (the graph showing numbers of Trypan Blue-excluding (live) cells after 1-4 days of culture). We conclude that the KD 13 line has partially overcome its HSF1 dependency. If the cytotoxicity of $I_{HSF}$ 115 was mediated through inhibition of HSF1, the cell line that had partially lost its HSF1 dependency should have been more resistant to killing by $I_{HSF}$ 115 than the control lentivirus-transduced cells. The results of Alamar Blue assays performed after 96 hours of exposure to different concentrations of the $I_{HSF}$ showed this to be the case (FIG. 7B).

Uses of HSF Inhibitors

In general, HSF inhibitors of the present disclosure can be used to inhibit the stress-induced transactivation ability of mammalian HSF1 in a mammalian cell or animal, in a human cell, tissue, organ or organism. Under "stress-induced transactivation ability" is understood the ability of activated HSF1 to cause a transient accumulation of transcripts of its target genes. Because HSF1 is the key regulator of the stress protein response, i.e., is a key regulator of proteostasis, a major application for the HSF inhibitors of the present disclosure will be in the therapy of conditions or diseases that are characterized by an increased demand for HSF1 activity by certain cells, tissues or organs compared to corresponding cells, tissues or organs in healthy subjects. Often, cells, tissues or organs in an afflicted subject display increased levels of HSF1 and/or of HSF1 activity (as detected by any suitable assay, e.g., DNA-binding assays, transactivation assays, nuclear accumulation assays, WB, etc.). Diseases that generally appear to have an increased demand for HSF1 activity include cancers of different types. Furthermore, certain infections also result in activation of HSF1, and progagation of the infectious agent is dependent on this induced HSF1 activity. A recently discovered example involves orthopoxviruses. Filone et al. (2014) PLoS Pathog. 2014, 10, e1003904. See also Wang et al. (2010) J. Transl. Med. 8: 44. In such infections, administration of an inhibitor of HSF1 can be an effective therapeutic measure. Moreover, HSF1 inhibitors may find uses in situations in which pharmacologically induced HSF1 activity may have negative or undesired consequences (e.g., during therapy with HSP90 inhibitors). Experiments with an HSF1−/− mouse strain revealed that HSF1 is a maternal effect gene. No embryos lacking HSF1 activity developed to the blastocyst stage. Christians et al. (2000) Nature 407: 693-4. Hence, HSF1 inhibitors are expected to have contraceptive activity.

In certain embodiments, one or more of the HSF inhibitors of the present disclosure are used either alone or in combination with other active anti-cancer therapeutic agents or regimens such as radiation therapy to prevent or treat cancer or neoplastic disease. Cancers to be treated include, but are not limited to, B cell lymphoma, T cell lymphoma, myeloma, leukemia (AML, ALL, CML, CLL), hematopoietic neoplasias, thymoma, lymphoma, sarcoma, lung cancer, liver cancer, non-Hodgkins lymphoma, Hodgkins lymphoma, Burkitt's lymphoma, breast cancer, pancreatic cancer, colon cancer, lung cancer, renal cancer, bladder cancer, liver cancer, prostate cancer, ovarian cancer, primary or metastatic melanoma, squamous cell carcinoma, basal cell carcinoma, sebaceous cell carcinoma, brain cancer (astrocytoma, glioma, glioblastoma, ependymoma, medulloblastoma, meningioma, oligodendroglioma, oligoastrocytoma), angiosarcoma, hemangiosarcoma, adenocarcinoma, liposarcoma, head and neck carcinoma, thyroid carcinoma, soft tissue sarcoma, osteosarcoma, testicular cancer, uterine cancer, cervical cancer, gastrointestinal cancer, colorectal cancer, oral cancer, nasopharyngeal cancer, oropharyngeal cancer, esophageal cancer, stomach cancer, multiple myeloma, bile duct cancer, cervical cancer, laryngeal cancer, penile cancer, urethral cancer, anal cancer, vulvar cancer, vaginal cancer, gall bladder cancer, thymoma, salivary gland cancer, lip and oral cavity cancer, adenocortical cancer, non-melanoma skin cancer, pleura mesothelioma, joint cancer, hypopharyngeal cancer, ureter cancer, peritoneum cancer, omentum cancer, mesentery cancer, Ewing's sarcoma, rhabdomyosarcoma, spinal cord cancer, endometrial cancer, neuroblastoma, pituitary cancer, retinoblastoma, eye cancer, and islet cell cancer, and any other cancer now known or later identified to be dependent or to benefit from HSF activity.

Examples of types of anti-cancer therapeutic agents with which the HSF inhibitors of the present disclosure may be combined include, but are not limited to, e.g., chemotherapeutic agents, growth inhibitory agents, agents used in radiation therapy (radioactive isotopes (e.g., $I_{131}$, $I_{125}$, $Y_{90}$ and $Re_{186}$), toxins such as enzymatically active toxins of bacterial, fungal, plant or animal origin, or fragments thereof, anti-angiogenesis agents, apoptotic agents, anti-tubulin agents, and other agents to treat cancer, such as inhibitors of HSP90, the proteasome or histone deacetylases (HDAC), in particular HDAC6, anti-HER-2 antibodies (e.g., Herceptin (Trastuzumab)), anti-CD20 antibodies, epidermal growth factor receptor (EGFR) antagonist (e.g., a tyrosine kinase inhibitor), HER1/EGFR inhibitor (e.g., erlotinib (Tarceva™)), platelet derived growth factor inhibitors (e.g., Gleevec™ (Imatinib Mesylate)), a COX-2 inhibitor (e.g., celecoxib), interferons, cytokines, antagonists (e.g., neutralizing antibodies) that bind to one or more of the following targets: ErbB2, ErbB3, ErbB4, PDGFR-beta, BlyS, APRIL, BCMA or VEGF receptor(s), TRAIL/Apo2, and other bioactive and organic chemical agents, etc. Combinations thereof are also included in the disclosure.

Example chemotherapeutic agents include one or more chemical compounds useful in the treatment of cancer. Non-limiting examples of chemotherapeutic agents include alkylating agents such as thiotepa and CYTOXAN, cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylol melamine; acetogenins (such as bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimustine; antibiotics such as the enediyne antibiotics (e.g., calicheamicin, especially calicheamicin gamma1); dynemicin, including dynemicin A; bisphosphonates, such as clodronate; an esperamicin; as well as neocarzinostatin chromophore and related enediyne chromoprotein antibiotics, aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, ADRIAMYCIN™, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK, polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (such as T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL™, paclitaxel (Bristol-Myers Squibb Oncology, Princeton, N.J.), ABRAXANE™, Cremophor-free, albumin-engineered nanoparticle formulation of paclitaxel (American Pharmaceutical Partners, Schaumberg, Ill.), and TAXOTERE™ doxetaxel (Rhone-Poulenc Rorer, Antony, France); chloranbucil; GEMZAR™ gemcitabine; 6-thioguanine; mercaptopurine; platinum analogs such as cisplatin and carboplatin; vinblastine; platinum; etoposide (VP-16); ifosfamide; mitoxantrone; vincristine; NAVELBINE vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); inhibitors of PKC-alpha, Raf, H-Ras, EGFR (e.g., erlotinib (Tarceva™)) and VEGF-A that reduce cell proliferation and pharmaceutically acceptable salts, acids or derivatives of any of the above. Also encompassed are anti-hormonal agents that act to regulate or inhibit hormone action on tumors such as anti-estrogens and selective estrogen receptor modulators (SERMs), including, for example, tamoxifen (including NOLVADEX™ tamoxifen), raloxifene, droloxifene, 4-hydroxytamoxifen, trioxifene, keoxifene, LY117018, onapristone, and FARESTON toremifene; aromatase inhibitors that inhibit the enzyme aromatase, which regulates estrogen production in the adrenal glands, such as, for example, 4(5)-imidazoles, aminoglutethimide, MEGASE™ megestrol acetate, AROMASIN™ exemestane, formestane, fadrozole, RIVISOR™ vorozole, FEMARA™ letrozole, and ARIMIDEX™ anastrozole; and antiandrogens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in aberrant cell proliferation, such as, for example, PKC-alpha, Raf and H-Ras; ribozymes such as a VEGF expression inhibitor (e.g., ANGIOZYME™ ribozyme) and a HER2 expression inhibitor; vaccines such as gene therapy vaccines, for example, ALLOVECTIN™ vaccine, LEUVECTIN™ vaccine, and VAXID™ vaccine; PROLEUKIN™, rIL-2; LURTOTECAN topoisomerase 1 inhibitor; ABARELIX™ rmRH; vinorelbine and esperamicins, and pharmaceutically acceptable salts, acids or derivatives of any of the above.

"Radiation therapy" refers to the use of directed gamma rays or beta rays to induce sufficient damage to a cell to limit its ability to function normally or to destroy the cell altogether. It will be appreciated that there will be many ways known in the art to determine the dosage and duration of treatment. Typical treatments are given as a one-time administration and typical dosages range from 10 to 200 units (Grays) per day.

Because the HSF inhibitors of the present disclosure are directed to hitherto unexploited tumor cell targets (i.e., HSF), they can enhance, additively or, possibly, synergistically, the activity of the aforementioned anti-cancer therapeutic agents or of radiation therapy. Preferred combinations will comprise an HSF inhibitor of the present disclosure and an anti-cancer therapeutic agent that induces a stress protein response, i.e., that enhances expression of heat shock proteins. Elevated levels of heat shock proteins have cytoprotective effects and thereby may, or are known to, negatively affect the anticancer efficacy of such agents. Agents that induce heat shock protein expression include HSP90 inhibitors, HDAC6 inhibitors and proteasome inhibitors.

Examples of HSP90 inhibitors that can be used in combination with an HSF inhibitor of the present disclosure include, but are not limited to, quinone ansamycin antibiotics, such as the macbecins, geldanamycin, including derivatives of geldanamycin, such as 17-AAG, herbimycin A, radicicol, and synthetic compounds that can bind into the N-terminal ATP-binding site of HSP90. HSP90 inhibitors that bind the C-terminal ATP-binding site have also been identified such as novobiocin, cisplatin, epigallocatechin-3-gallate (EGCG) and taxol (Donelly and Blagg (2008) Curr. Med. Chem. 15: 2702-2717). Another HSP90 inhibitor that appears to interact with the C-terminal ATP-binding site is celastrol and its derivatives (Zhang et al. (2009) J. Biol. Chem. 284: 33381-33389). HSP90 inhibitors are also described in U.S. Pat. Publ. Nos. 2008/0269218, 2008/0306054, 2010/0249231 and 2011/0112099.

Inhibitors of HDAC6 activity that can be used in combination with an HSF inhibitor of the present disclosure include but are not limited to hydroxamic acid-based HDAC inhibitors, suberoylanilide hydroxamic acid (SAHA) and its derivatives, NVP-LAQ824, trichostatins including trichostatin A, scriptaid, m-carboxycinnamic acid bishydroxamic acid (CBHA), ABHA, pyroxamide, propenamides, oxamflatin, 6-(3-chlorophenylureido)caproic hydroxamic acid (3-Cl-UCHA), A-161906, JNJ-16241199, tubacin and tubacin analogs, siRNA (see, e.g., U.S. Pat. Publ. No. 2007/0207950), butyrate, phenylbutyrate, sodium butyrate, valproate, (−)-depudecin, sirtinol, hydroxamic acid, epoxyketone-containing cyclic tetrapeptides, trapoxins, HC-toxin, chlamydocin, diheteropeptide, WF-3161, Cy1-1, Cy1-2, non-epoxyketone-containing cyclic tetrapeptides, PXD101, dimeric HDAC inhibitors, certain depsipeptides, FR901228 (FK228), apicidin, APHA compound 8, cyclic-hydroxamic-acid-containing peptides (CHAPS), benzamides and benzamide analogs, MS-275 (MS-27-275), CI-994, LBH589, deprudecin, organosulfur compounds and any combination thereof. An inhibitor of HDAC6 activity can be an inhibitor that acts at the level of transcription and/or translation of the HDAC6 protein, whereby such an inhibitor alters HDAC6 activity by decreasing the amount of functional HDAC6 protein produced. An inhibitor of HDAC6 activity can be, but is not limited to, an antisense nucleic acid, a ribozyme (e.g., as described in U.S. Pat. No. 5,877,022), RNAs that effect spliceosome-mediated trans-splicing (Puttaraju et al. (1999) Nature Biotech. 17:246; U.S. Pat. Nos. 6,013,487; 6,083,702), RNAs that trigger RNA interference mechanisms (RNAi), including small interfering RNAs (siRNA) that mediate gene silencing (Kawaguchi et al., (2003) Cell 115:727-738; Sharp et al. (2000) Science 287:2431) and/or other non-translated RNAs, such as "guide" RNAs (Gorman et al., (1998) Proc. Nat. Acad. Sci. USA 95:4929; U.S. Pat. No. 5,869,248) and the like, as are known in the art.

Examples of a proteasome inhibitor (European Journal of Cancer, 42, 1623, (2006)) that can be used in combination with an HSF inhibitor of the present disclosure include, for example, bortezomib, MG-132, carfilzomib (PR-171; US2005/0245435), NPI-0052 (Br. J. Cancer, 95, 961, (2006)), SC-68896 (WO2007/017284), tyropeptin A, TP-110, TP-104 (WO2005/105826), belactosins (Biochem. Pharmacol., 67, 227, (2004)) and the like.

HSF inhibitors of the disclosure may also be used to mitigate resistance to anti-cancer therapeutic agents that target signaling through an HSF. For example, ErbB2 over-expression results in enhanced aerobic glycolysis as a consequence of over-expression of HSF1 and its target LDH A. Trastuzumab inhibits this activity. Resistance to trastuzumab can be reversed by inhibiting aerobic glycolysis, which can be achieved by inhibition of HSF1. Zhao et al. (2011) Cancer Res. 71: 4585-97; Zhao et al. (2009) Oncogene 28: 3689-3701.

The anti-cancer therapeutic agent and/or radiation therapy can be administered according to therapeutic protocols well known in the art. It will be apparent to those skilled in the art that the administration of the anti-cancer therapeutic agent and/or radiation therapy can be varied depending on the disease being treated and the known effects of the chemotherapeutic agent and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., anti-cancer therapeutic agent or radiation) on the patient, and in view of the observed responses of the disease to the administered therapeutic agents, and observed adverse affects.

Also, in general, an HSF inhibitor of the present disclosure and an anti-cancer therapeutic agent do not have to be administered in the same pharmaceutical composition, and, due to differences in physical and chemical characteristics, may be administered by different routes. For example, compounds of the present disclosure may be administered intravenously, whereas the chemotherapeutic agent may be administered orally. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The particular choice of chemotherapeutic agent or radiation will depend upon the diagnosis of the physicians and their judgment of the condition of the patient and the appropriate treatment protocol.

An HSF inhibitor of the present disclosure and an anti-cancer therapeutic agent and/or radiation may be administered concurrently (e.g., simultaneously, essentially simultaneously or within the same treatment protocol) or sequentially, depending upon the nature of the proliferative disease, the condition of the patient, and the actual choice of anti-cancer therapeutic agent and/or radiation to be administered in conjunction with the HSF inhibitor.

If an HSF inhibitor of the present disclosure and the anti-cancer therapeutic agent and/or radiation is not administered simultaneously or essentially simultaneously, then the optimum order of administration of the compound of the present disclosure, and the anti-cancer therapeutic agent and/or radiation, may be different for different tumors. Thus, in certain situations the HSF inhibitor of the present disclosure may be administered first followed by the administration of the anti-cancer therapeutic agent and/or radiation, whereas in other situations the anti-cancer therapeutic agent and/or radiation may be administered first followed by the administration of an HSF inhibitor of the present disclosure. Such administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient. For example, the anti-cancer therapeutic agent and/or radiation may be administered first, especially if it has a cytotoxic effect, and then the treatment may be continued with the administration of a compound of the present disclosure followed, where determined advantageous, by the re-administration of the anti-cancer therapeutic agent and/or radiation, and so on until the treatment protocol is completed.

Thus, in accordance with experience and knowledge, the practicing physician can modify each protocol for the administration of a component (therapeutic agent, i.e., compound of the present disclosure, anti-cancer therapeutic agent or radiation) of the treatment according to the individual patient's needs, as the treatment proceeds.

Pharmaceutical Compositions

The pharmaceutical compositions of the present disclosure comprise an effective amount of an HSF inhibitor of the present disclosure (preferably a compound of formulae (II), (V), (IX) or (X)) formulated together with one or more pharmaceutically acceptable carriers or excipients.

The pharmaceutical compositions of this disclosure may be administered orally, parenterally, by inhalation spray, topically, rectally, nasally, buccally, vaginally or via an implanted reservoir, preferably by oral administration or administration by injection (or infusion).

The pharmaceutical compositions of this disclosure may contain any conventional non-toxic pharmaceutically acceptable carriers, adjuvants or vehicles. In some cases, the pH of the formulation may be adjusted with pharmaceutically acceptable acids, bases or buffers to enhance the stability of the formulated HSF inhibitor or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to an active compound (i.e., an HSF inhibitor of the disclosure), the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent. Among the acceptable vehicles and solvents that may be employed are water, Ringer's solution, U.S.P. and isotonic sodium chloride solution. Solubilizing excipients include water-soluble organic solvents such as polyethylene glycol 300, polyethylene glycol 400, ethanol, propylene glycol, glycerin, N-methyl-2-pyrrolidone, dimethylacetamide and dimethylsulfoxide; non-ionic surfactants such as Cremophor EL, Cremophor RH40, Cremophor RH60, Solutol HS15, d-α-tocopherol polyethylene glycol 1000 succinate, polysorbate 20, polysorbate 80, sorbitan monooleate, poloxamer 407, Labrafil M-1944CS, Labrafil M-2125CS, Labrasol, Gellucire 44/14, Softigen 767, and mono- and di-fatty acid esters of PEG 300, 400 and 1750; water-insoluble lipids such as castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil and palm seed oil, various cyclodextrins such as α-cyclodextrin, β-cyclodextrin, hydroxypropyl-β-cyclodextrin (e.g., Kleptose), and sulfobutylether-β-cyclodextrin (e.g., Captisol); and phospholipids such as lecithin, hydrogenated soy phosphatidylcholine, distearoylphosphatidylglycerol, L-α-dimyristoylphosphatidylcholine and L-α-dimyristoylphosphatidylglycerol. Strickley (2004) Pharm. Res. 21: 201-30.

The injectable formulations can be sterilized, for example, by filtration through a bacteria-retaining filter, or by incorporating sterilizing agents in a sterile solid composition (or sterilize the solid composition by irradiation) which subsequently can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by microencapsulating the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this disclosure with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this disclosure include ointments, pastes, creams, lotions, gels, powders, solutions, sprays, inhalants or patches. The active component is admixed under sterile conditions with a pharmaceutically acceptable carrier and any preservatives or buffers as may be required. Ophthalmic formulations, ear drops, eye ointments, powders and solutions are also contemplated as being within the scope of this disclosure.

The ointments, pastes, creams and gels may contain, in addition to a compound of this disclosure, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to compounds of this disclosure, excipients such as lactose, talc, silicic acid, aluminum hydroxide, calcium silicates and polyamide powder, or mixtures of these substances. Sprays can additionally contain customary propellants.

Transdermal patches can be made by dissolving or dispensing the active in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the disclosure is formulated and administered to the patient in solid or liquid particulate form by direct administration e.g., inhalation into the respiratory system. Solid or liquid particulate forms of the active compound prepared for practicing the present disclosure include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. Nos. 5,767,068, 5,508,269 and WO 98/43650). A discussion of pulmonary delivery of antibiotics is also found in U.S. Pat. No. 6,014,969.

The total daily dose of an HSF inhibitor of this disclosure administered to a human subject or patient in single or in divided doses can be, for example, from 0.01 to 50 mg/kg body weight or more usually from 0.1 to 30 mg/kg body weight. Single dose compositions may contain such amounts or submultiples thereof to make up the daily dose. In general, treatment regimens according to the present disclosure comprise administration to a human subject in need of such treatment from about 1 mg to about 5000 mg of the compound(s) of this disclosure per day in single or divided doses. Doses for mammalian animals can be estimated based on the latter human doses.

An HSF inhibitor of this disclosure can be administered, for example, by injection, intravenously, intraarterially, subdermally, intraperitoneally, intramuscularly, or subcutaneously; or orally, buccally, nasally, transmucosally, topically, in an ophthalmic preparation, or by inhalation, as a daily dose of about 0.01 to about 50 mg/kg of body weight. Alternatively, dosages (based on a daily dose of between about 1 mg and 5000 mg) may be administered every 4 to 120 hours, or according to the requirements of the particular inhibitor drug. The methods herein contemplate administration of an effective amount of HSF inhibitor (in a pharmaceutical composition) to achieve the desired or stated effect. Typically, the pharmaceutical compositions of this disclosure will be administered from about 1 to about 6 times per day or alternatively, as a continuous infusion. Such administration can be used as a chronic or acute therapy. The amount of active compound that may be combined with pharmaceutically acceptable excipients or carriers to produce a single dosage form will vary depending upon the host treated and the particular mode of administration. A typical composition will contain from about 5% to about 95% active compound (w/w). Alternatively, such preparations may contain from about 20% to about 80% active compound. Specific dosage and treatment regimens for any particular patient will depend upon a variety of factors, including the activity of the specific HSF inhibitor employed, the age, body weight, general health status, sex, diet, time of administration, rate of excretion, drug combination, the severity and course of the disease, condition or symptoms, the patient's disposition to the disease, condition or symptoms, and the judgment of the treating physician.

All references cited in this application, including publications, patents and patent applications, shall be considered as having been incorporated in their entirety.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e. g., all exact exemplary values provided with respect to a particular factor or measurement can be considered to also provide a corresponding approximate measurement, modified by "about," where appropriate).

The description herein of any aspect or embodiment of the invention using terms such as reference to an element or elements is intended to provide support for a similar aspect or embodiment of the disclosure that "consists of," "consists essentially of" or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

The present disclosure, thus generally described, will be understood more readily by reference to the following examples, which are provided by way of illustration and are not intended to be limiting of the present invention.

EXAMPLES

Example 1: Synthesis of HSF Inhibitors

Abbreviations

APCI, atmospheric pressure chemical ionization; Aq., aqueous; Boc, tert-butoxycarbonyl; $Boc_2O$, Di-tert-butyl dicarbonate; Conc., concentrated; DCE, 1,2-dichloroethane; DCM, dichloromethane; DDQ, 2,3-dichloro-5,6-dicyano-1,4-benzoquinone; DIPEA, N,N-diisopropylethylamine; DMF-DMA, N—N Dimethyl formamide dimethyl acetal; DME, 1,2-dimethoxyethane; DMF, dimethylformamide; EDC, 1-ethyl-3-[3-dimethylaminopropyl]carbodiimide; ELSD, evaporative light scattering detection; equiv., equivalents; $Et_2O$, diethyl ether; EtOAc, ethyl acetate; EtOH, ethanol; h, hours; HATU, 2-(7-aza-1H-benzotriazole-1-yl)-1,1,3,3-tetramethyluronium hexafluorophosphate; HOBt, N-hydroxybenzotriazole; HPLC, high performance liquid chromatography; LC-MS, liquid chromatography mass spectrometry; IBCF, isobutyl chloroformate; IPA, 2-propanol; MeI, iodomethane; MeOH, methanol; min, minute; MP-Carbonate, macroporous triethylammonium methylpolystyrene carbonate; NBS, N-bromosuccinimide; N,N,N',N'-methylmorpholine; NMR, nuclear magnetic resonance; pet. ether, petroleum ether; PTSA, p-Toluenesulfonic acid; Rt, retention time; Sat., saturated; Si—$NH_2$, aminopropyl bonded silica; Si-Thiol, silica 1-propanethiol; TBTU, O-(benzotriazol-1-yl)N,N,N',N'-tetramethyluronium tetrafluoroborate; TFA, trifluoroacetic acid; THF, tetrahydrofuran; TLC, thin layer chromatography; TMOF, trimethylorthoformate; TMS, trimethylsilane; % v/v, percentage volume to volume; % w/v, percentage weight to volume.

Analytical Methods

Reverse Phase Preparative LC-MS: Mass-directed purification preparative LC-MS using a preparative C-18 column (Phenomenex Luna C18 (2), 100×21.2 mm, 5 μm).

Analysis of products and intermediates has been carried out using reverse-phase analytical HPLC-MS using the parameters set out below.

HPLC Analytical Methods:

AnalpH2_MeOH_4 min: Phenomenex Luna C18 (2) 3 μm, 50×4.6 mm; A=water+0.1% formic acid; B=MeOH; 45° C.; % B: 0 min 5%, 1 min 37.5%, 3 min 95%, 3.51 min 5%, 4.5 min 5%; 2.25 mL/min.

AnalpH9_MeOH_4 min: Phenomenex Luna C18 (2) 3 μm, 50×4 6 mm; A=water pH9 (Ammonium Bicarbonate 10 mmol); B=MeOH; 45° C.; % B: 0 min 5%, 1 min 37.5%, 3 min 95%, 3.51 min 5%, 4.5 min 5%; 2.25 mL/min.

AnalpH2_MeOH_QC: Phenomenex Luna C18 (2) 3 μm, 50×4.6 mm; A=water+0.1% formic acid; B=MeOH; 35° C.; % B: 0 min 5%, 7.5 min 95%, 10 min 95%, 10.10 min 5%,13.0 min 5%; 1.5 mL/min.

AnalpH2_MeCN_QC: Phenomenex Luna C18 (2) 3 μm, 50×4.6 mm; A=water+0.1% formic acid; B=MeCN+0.1% TFA; 40° C.; % B: 0 min 5%, 0.1 min 5%, 8 min 95%, 10.5 min 95%, 10.55 min 5%, 13.5 min 5%; 1.5 mL/min.

AnalpH9_MeOH_QC: Phenomenex Luna C18 (2) 3 μm, 50×4.6 mm; A=water+0.1% formic acid; B=MeOH; 45° C.; % B: 0 min 5%, 7.5 min 95%, 10 min 95%, 10.10 min 5%, 13.0 min 5%; 1.5 mL/min.

Method_2_TFA_UPLC_2: Acquity UPLC BEH C18 1.7 μm, 100×2.1 mm; 25° C.; A=water+0.025% TFA; B=acetonitrile+0.025% TFA; % B: 0 min 30%, 4 min 80%, 6 min 80%, 6.1 min 30%; 0.4 mL/min.

Method_4_TFA_UPLC_2: Acquity UPLC BEH C18 1.7 μm, 100×2.1 mm; 25° C.; A=water+0.025% TFA; B=acetonitrile+0.025% TFA; % B: 0 min 10%, 4 min 80%, 6 min 80%, 6.1 min 10%; 0.3 mL/min.

AK4: Acquity UPLC BEH C18 1.7 μm, 50×2.1 mm; A=water+0.025% TFA; B=acetonitrile+0.025% TFA; % B: 0 min 15%, 3 min 95%, 4 min 95%, 4.1 min 15%; 0.4 mL/min.

AK4P: Acquity UPLC BEH C18 1.7 μm, 50×2.1 mm; A=water+0.025% TFA; B=acetonitrile+0.025% TFA; % B: 0 min 10%, 3 min 80%, 4 min 80%, 4.1 min 10%; 0.3 mL/min.

XTERRA: Xterra MS C18 3 μm, 50×4.6 mm; A=water+0.1% HCOOH; B=acetonitrile; % B: 0 min 10%, 4 min 90%, 8 min 90%, 8.01 min 10%; 1 mL/min.

LCMS-2: Acquity UPLC BEH C18 1.7 μm, 50×2.1 mm; A=water+0.025% TFA; B=acetonitrile+0.025% TFA; % B: 0 min 20%, 2 min 90%, 3 min 90%, 3.1 min 20%; 0.4 mL/min.

1.1 Synthesis of Intermediates

Figure 8:
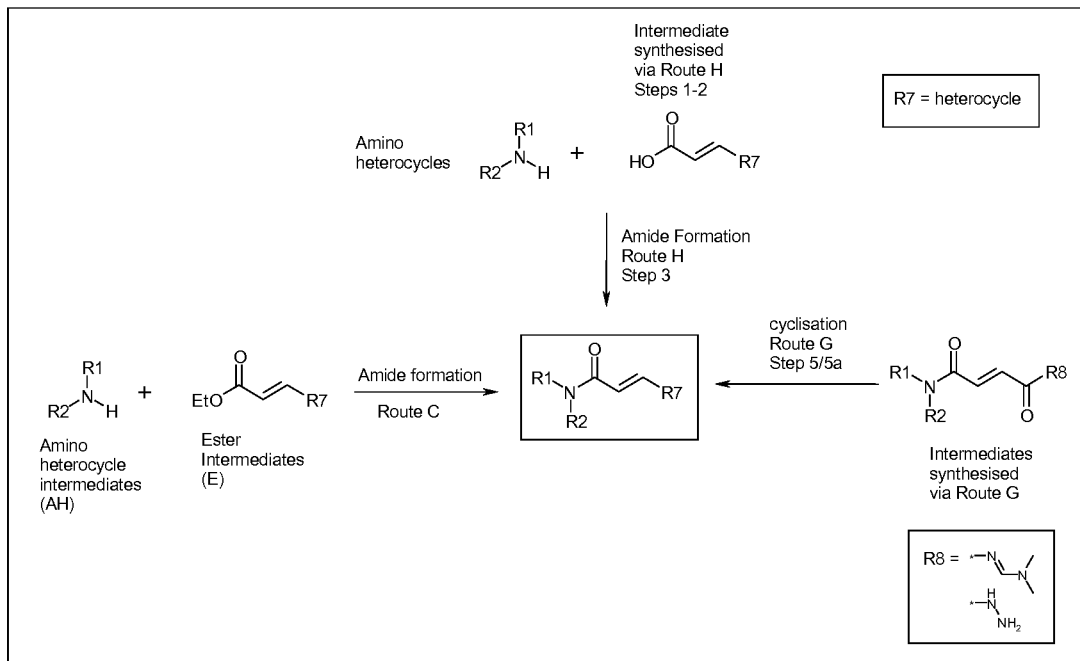
FIG. 8. General experimental procedures for the synthesis of HSF1 inhibitors FIG. 9. Inhibition of tumor growth mediated by $I_{HSF}$ 115. QD: daily.
Figure 8:
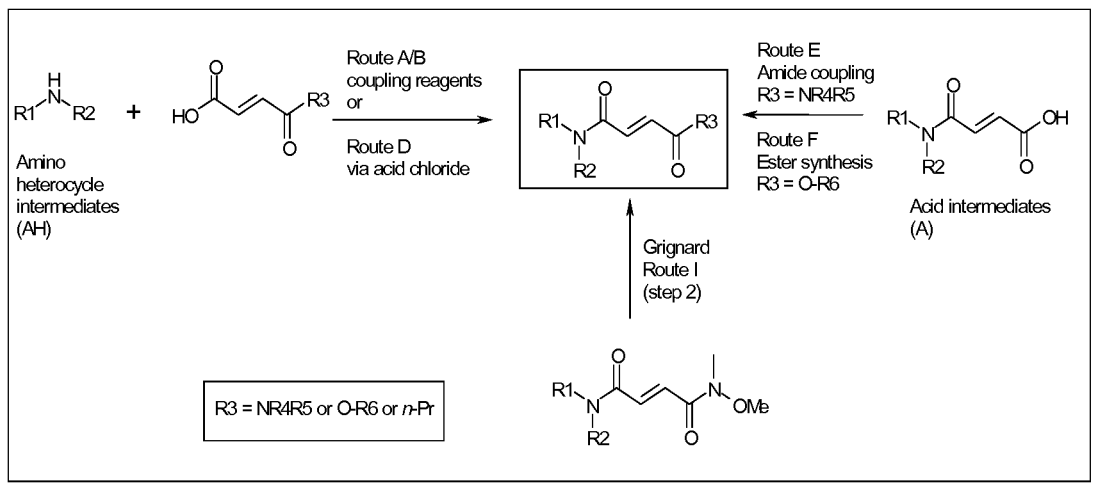

General experimental schemes for the synthesis of HSF inhibitors of the disclosure are provided in FIG. 8.

1.1.1 Synthesis of Amino Heterocycles (AH)

1.1.1.1 Amino Heterocycle Intermediates AH1, AH2:

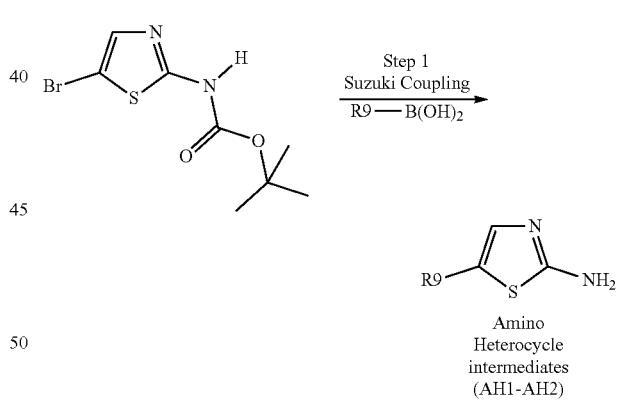

Step 1—Suzuki Coupling

Figure 9:
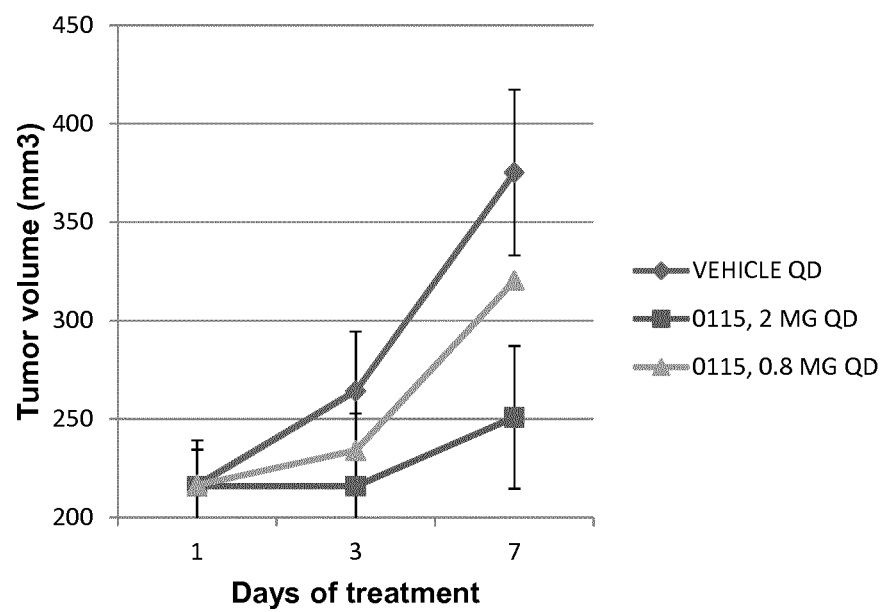

To a microwave vial was added N-Boc-2-amino-5-bromo-thiazole (0.09 mmol, 1 equiv.) followed by the boronic acid (0.27 mmol, 3 equiv.), $Pd(PPh_3)_2Cl_2$ (0.005 mmol, 0.05 equiv.), aq. $Cs_2CO_3$ (4 M, 0.36 mmol, 4 equiv.) and DME/EtOH/water 7:2:3 (1 mL). The reaction mixture was de-gassed with nitrogen for 2 min and irradiated in a microwave at 130° C. for 8 min. LC-MS analysis showed that the Boc group had been removed during the reaction. The reaction mixture was passed through 1 g Si-Thiol cartridges, eluting with EtOH. The filtrate was evaporated to dryness, purified by preparative LC-MS and isolated directly as the amine for use in Routes A, D (FIG. 9).

TABLE 4

Amino Heterocycle Intermediates (AH) Prepared by Step 1

| Compound | ID | Analytical Data | Yield |
|---|---|---|---|
| 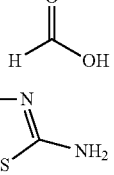<br>5-o-Tolyl-thiazol-2-ylamine formic acid salt | AH1 | AnalpH2_MeOH_4MIN; Rt 1.65 min; m/z 191 (MH$^+$); pale yellow solid | 22 mg, 34% |
| 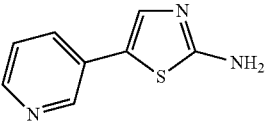 [SMILES: Nc1ncc(-c2cccnc2)s1]<br>5-Pyridin-3-yl-thiazol-2-ylamine | AH2 | AnalpH2_MeOH_4MIN; Rt 0.62 min; m/z 178 (MH$^+$); pale brown solid | 13 mg, 21% |

1.1.1.2 Synthesis of Amino Heterocycle Intermediate AH3:

Step 1: tert-Butyl thiazol-2-ylcarbamate: to a solution of 2-amino thiazole (30 g, 300 mmol) in THF (300 mL) was added Boc$_2$O (79 mL, 360 mmol) and the reaction mixture was stirred at ambient temperature for 16 h. The reaction mixture was concentrated under reduced pressure, and the precipitated solid was washed with pet.-ether to afford tert-butyl thiazol-2-ylcarbamate (50 g, 83%). MS (APCI); m/z 201 (MH$^+$).

Step 2: tert-Butyl methyl(thiazol-2-yl)carbamate: to a suspension of NaH (60% in mineral oil suspension, 13.3 g, 330 mmol) in DMF, cooled to 5° C., was added tert-butyl thiazol-2-yl carbamate (55 g, 275 mmol) followed by dropwise addition of iodomethane (58.16 g, 412 mmol). The reaction mixture was allowed to warm to ambient temperature over 2 h. The reaction mixture was poured onto crushed ice, stirred, and the precipitated solid was filtered and dissolved in pet. ether, dried over anhydrous Na$_2$SO$_4$ and concentrated under reduced pressure to afford tert-butyl methyl(thiazol-2-yl)carbamate as an off-white solid (48 g, 82%). MS (APCI); m/z 215 (MH$^+$).

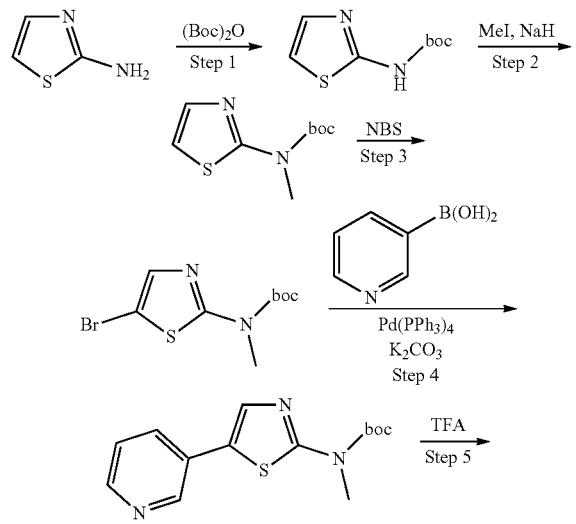

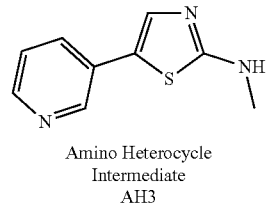

Amino Heterocycle Intermediate AH3

Step 3: tert-Butyl 5-bromothiazol-2-yl(methyl)carbamate: to a solution of tert-butyl methyl(thiazol-2-yl)carbamate (52 g, 243 mmol) in THF (520 mL), cooled to 5° C. was added NBS (47 g, 267 mmol) in ten portions. The reaction mixture was allowed to stir at ambient temperature for 2 h. The reaction mixture was concentrated, and triturated with pet.-ether. The precipitated solids were filtered and dried to afford tert-butyl 5-bromothiazol-2-yl(methyl)carbamate as a pale yellow solid (62 g, 87%). $^1$H NMR (CDCl$_3$) –δ1.58 (s, 9H), δ3.49 (s, 3H), δ7.33 (s, 1H).

Step 4: tert-Butyl methyl (5-(pyridin-3-yl)thiazol-2-yl) carbamate: to a solution of tertbutyl 5-bromothiazol-2-yl (methyl)carbamate (25 g, 85.32 mmol) and 3-pyridine boronic acid (15.7 g, 127.98 mmol) in DME/water (320 mL/80 mL) under an argon atmosphere was added K$_2$CO$_3$ (37.13 g, 273.03 mm) followed by Pd(PPh$_3$)$_4$ (9.8 g, 8.53 mmol), and the reaction mixture was heated to 100° C. for 16 h. The reaction mixture was cooled to ambient temperature, filtered through a celite pad, concentrated under vacuum and partitioned between water and EtOAc. The organic layer was dried over anhydrous Na$_2$SO$_4$ and concentrated. The crude compound was purified by column chromatography (silica gel 100-200 mesh, 30-40% EtOAc/pet. ether) to afford tert-butyl methyl (5-(pyridin-3-yl)thiazol-2-yl)carbamate as an off-white solid (15 g, 52%). AK4; Rt 1.68 min (98%); m/z 292 (MH$^+$).

Step 5: N-Methyl-5-(pyridin-3-yl)thiazol-2-amine (Amino Heterocycle Intermediate AH3): a solution of tert-butyl methyl (5-(pyridin-3-yl)thiazol-2-yl)carbamate (21 g, 72.4 mmol) in TFA/DCM (1:1, 157 mL) was stirred at ambient temperature for 2 h. The reaction mixture was concentrated and basified with sat. aq. NaHCO₃ solution and extracted with EtOAc. The organic layer was dried over Na₂SO₄ and concentrated in vacuo to afford N-methyl-5-(pyridin-3-yl)thiazol-2-amine as an off-white solid (10.7 g, 78%). AK4P; Rt 0.86 min (100%); m/z 192 (MH⁺); ¹H NMR (d6-DMSO) −δ2.86-2.87 (d, 3H), δ7.34-7.37 (d of d, 1H), −δ7.64 (s, 1H), δ7.77-7.86 (m, 2H), δ8.36-8.37 (d, 1H), δ8.68 (s, 1H)

1.1.1.3 Synthesis of Amino Heterocycle Intermediates (AH4-AH6)

1.1.1.4 Synthesis of Amino Heterocycle Intermediate AH7

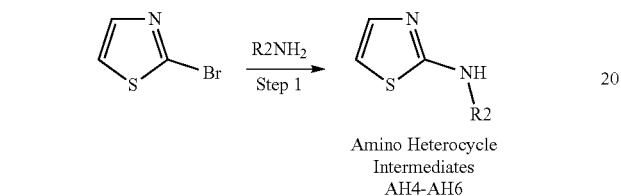

Step 1: [2-(1-Methyl-1H-imidazol-4-yl)-ethyl]thiazol-2-yl-amine—AH7. To a solution of 2-bromothiazole (400 mg, 1 equiv., 2.43 mmol) in IPA (5 mL) was added 1-methyl-histamine (610 mg, 2 equiv., 4.87 mmol) and the reaction was heated at 90° C. for 96 h after which time the solvent was removed under vacuum and the crude residue purified by preparative LC-MS to afford the title compound as a golden colored glass (120 mg, 23%). AnalpH2_MeOH_4 min; Rt 0.27 min (>95%); m/z 209 (MH⁺).

Step 1: To a solution of 2-bromothiazole (0.6 mmol, 1 equiv.) in 1,4-dioxane (0.5 mL) was added the amine (10 equiv., 6 mmol) and the reaction subjected to microwave irradiation at 180° C. for 30 min after which time the solvent was removed and the crude residue purified by preparative LC-MS to afford the desired product.

TABLE 5

Amino Heterocycle Intermediates AH4-6

| Compound | ID | Analytical Data | Yield |
|---|---|---|---|
| (2-Pyridin-4-yl-ethyl)thiazol-2-yl-amine | AH4 | AnalpH9_MeOH_4min; Rt 2.09 min (90%); m/z 206 (MH⁺); Green glass | 65 mg (52%) |
| (2-morpholin-4-yl-ethyl)thiazol-2-yl-amine | AH5 | AnalpH9_MeOH_4min; Rt 2.14 min (>95%); m/z 214 (MH⁺); Gold glass | 42 mg (32%) |
| (2-Pyridin-2-yl-ethyl)thiazol-2-yl-amine | AH6 | AnalpH9_MeOH_4min; Rt 2.08 min (90%); m/z 206 (MH⁺); Orange glass | 38 mg (30%) |

1.1.1.5 Synthesis of Amino Heterocycle Intermediates AH8, AH10

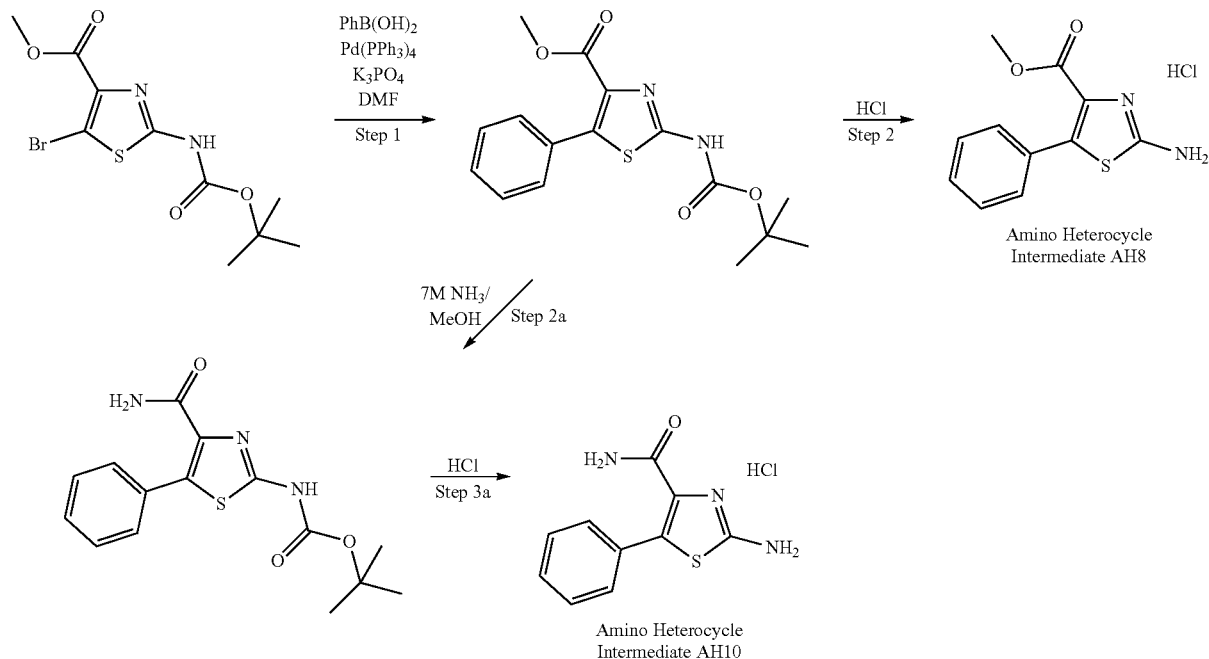

Amino Heterocycle Intermediate AH8

Amino Heterocycle Intermediate AH10

Step 1: 2-tert-Butoxycarbonylamino-5-phenyl-thiazole-4-carboxylic acid methyl ester. To a solution of 5-bromo-2-tert-butoxycarbonylamino-thiazole-4-carboxylic acid methyl ester (250 mg, 1 equiv., 0.74 mmol) in DME (2.5 mL) was added phenyl boronic acid (135 mg, 1.5 equiv., 1.11 mmol) and Pd(PPh$_3$)$_4$ (42 mg, 0.05 equiv., 0.037 mmol) and the reaction mixture degassed for 2 min under nitrogen. Potassium phosphate tribasic (aq. 2 M, 1.48 mL, 4 equiv., 2.96 mmol) was added and the reaction mixture degassed for 2 min under nitrogen after which time the reaction was subjected to microwave irradiation at 90° C. for 10 min. The crude reaction mixture was diluted with DCM (5 mL) and water (5 mL) and the organics obtained by means of filtration through a phase separation cartridge after which time the solvent was removed under vacuum and the crude residue purified by silica column chromatography with 0-30% EtOAc/isohexane as the eluent to afford the title compound as a yellow solid (236 mg, 47%). AnalpH2_MeOH_4 min; Rt 3.15 min (>95%); m/z 335 (MH$^+$).

Step 2: 2-Amino-5-phenyl-thiazole-4-carboxylic acid methyl ester (AH8). To a solution of 2-tert-butoxycarbonylamino-5-phenyl-thiazole-4-carboxylic acid methyl ester (50 mg, 1 equiv., 0.15 mmol) in DCM (0.5 mL) at 0° C. was added 4M HCl/dioxane (0.5 mL), and the reaction was stirred at ambient temperature for 1 h after which time the solvent was removed under vacuum and the crude residue azeotroped with toluene (2×10 mL) to afford the title compound as a gold colored glass (38 mg, 94%). AnalpH2_MeOH_4 min; Rt 2.22 min (>95%); m/z 235 (MH$^+$).

Step 2a: (4-Carbamoyl-5-phenyl-thiazol-2-yl)-carbamic acid tert-butyl ester. A solution of 2-tert-butoxycarbonylamino-5-phenyl-thiazole-4-carboxylic acid methyl ester (480 mg, 1 equiv., 1.43 mmol) in ammonia (7 M in MeOH) (30 mL) was heated at 110° C. for 16 h in a sealed tube after which time the solvent was removed and the crude residue purified by silica column chromatography with 0-50% EtOAc/isohexane as the eluent to afford the title compound as a white solid (260 mg, 56%). AnalpH2_MeOH_4 min; Rt 2.95 min (>95%); m/z 320 (MH$^+$).

Step 3a: 2-Amino-5-phenyl-thiazole-4-carboxylic acid amide (AH10). The procedure followed was the same as step 2 (above). This afforded the title compound as a white solid (60 mg, 95%). AnalpH2_MeOH_4 min; Rt 1.75 min (>95%); m/z 220 (MH$^+$).

1.1.1.6 Synthesis of Amino Heterocycle Intermediate AH9

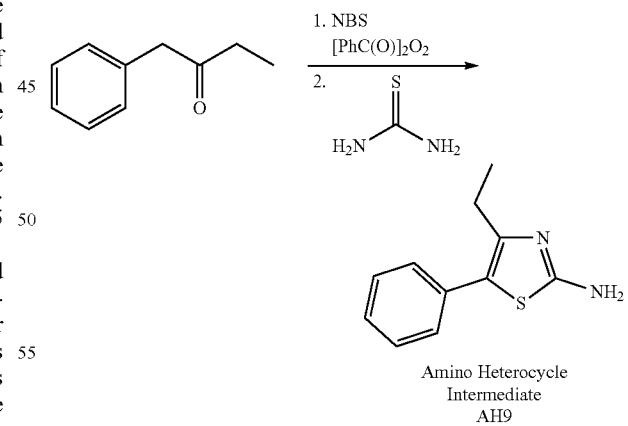

Amino Heterocycle Intermediate AH9

Step 1: 4-Ethyl-5-phenyl-thiazol-2ylamine (AH9). To a solution of 4-phenyl-2-butanone (500 mg, 1 equiv., 3.37 mmol) in DCE (20 mL) was added NBS (719 mg, 1.2 equiv., 4.04 mmol) and benzoyl peroxide (11 mg, 0.013 equiv., 0.045 mmol), and the reaction was heated at 80° C. for 2 h after which time the reaction was cooled to ambient temperature, diluted with DCM, washed with aq. sodium bisulfate (10% w/v, 20 mL) and sat. aq. sodium bicarbonate (20 mL), dried over MgSO$_4$, filtered and the solvent removed under vacuum. The resulting residue was dissolved in EtOH (20 mL) followed by the addition of thiourea (739 mg, 2.8 equiv., 9.71 mmol) and the reaction heated at 80° C. for 2 h, after which time sat. aq. sodium bicarbonate (10 mL) was added and the precipitate collected by filtration and dried under vacuum to afford the title compound as a cream solid (688 mg, 100%). AnalpH2_MeOH_4 min; Rt 1.63 min (>95%); m/z 205 (MH$^+$).

1.1.2 Synthesis of Acid Intermediates (A)

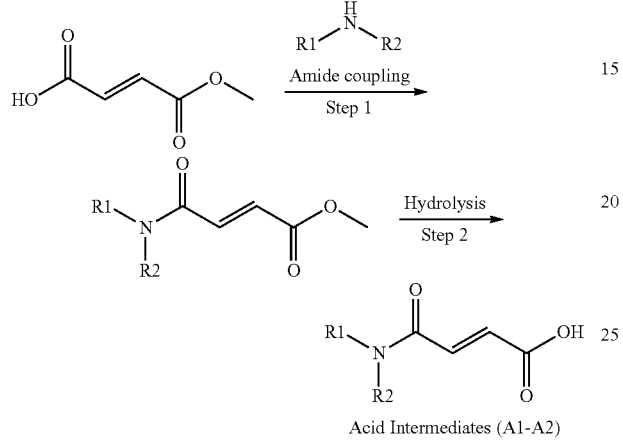

Acid Intermediates (A1-A2)

Typical Procedure:

Step 1: Amide Coupling. As route A except the compound was used crude in the next step.

Step 2: Ester Hydrolysis: to a solution of the ester in THF (~0.1 M) was added 1 M aq. LiOH (5 equiv.). The reaction mixture was stirred at ambient temperature, overnight. The reaction mixture was evaporated to dryness, re-dissolved in water and acidified to pH 2 with 0.1 M or 0.5 M HCl. Product was extracted into EtOAc. The organic layer was washed with brine, dried with MgSO$_4$ and evaporated to dryness to give the acid intermediate (A1-A2) which was used directly in Route E.

for 30 min. Amine (2 equiv.) was added to the above reaction mixture and stirred for 1 h at −40° C. After completion of the reaction (monitored by TLC), the reaction mixture was diluted with water and extracted with EtOAc. The organic layer was dried over anhydrous Na$_2$SO$_4$ and concentrated under reduced pressure to obtain crude compound. The crude compound was purified by silica gel column chromatography (1:1 pet. ether/EtOAc) to afford the corresponding amide.

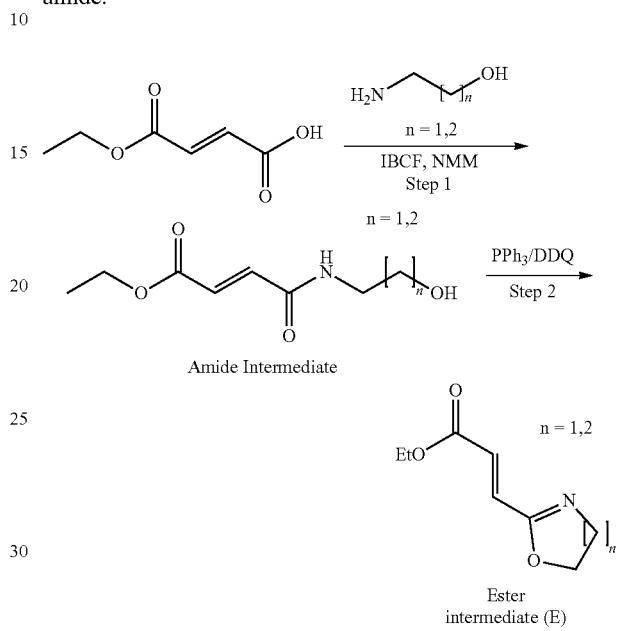

Ester intermediate (E)

Step 2: Cyclisation to the Ester Intermediate (E). To a stirred solution of triphenyl phosphine (1.5 equiv.) in DCM (0.15 M) at ambient temperature was added DDQ (1.5 equiv.). The reaction mixture was stirred for 10 min. A pre-mixed solution of the amide intermediate (1 equiv.) in DCM (2 M) was added slowly at ambient temperature over a period of 15 min and stirred for 20 min. After completion of the reaction (monitored by TLC), the reaction mixture

TABLE 6

| Acid Intermediates (A) | | | |
|---|---|---|---|
| Compound | ID | Analytical Data | Yield |
| (E)-3-(Thiazol-2-ylcarbamoyl)-acrylic acid | A1 | AnalpH2_MeOH_4MIN; Rt 1.86 min; m/z 199 (MH$^+$); yellow solid | 68 mg, 82% |
| (E)-3-(4-Methyl-thiazol-2-ylcarbamoyl)-acrylic acid | A2 | AnalpH2_MeOH_4MIN; Rt 2.18 min; m/z 213 (MH$^+$); pale yellow solid | 127 mg, 82% |

1.1.3 Synthesis of Ester Intermediates (E)

Step 1: Amide Formation. To a solution of ethyl hydrogen fumarate (1 equiv.) in THF (1.16 M), cooled to −40° C. was added isobutyl chloroformate (1.5 equiv.) dropwise followed by NMM (2 equiv.). The reaction mixture was stirred was diluted with 5% w/v aq. NaOH and extracted with DCM. The organic layer was dried with anhydrous Na$_2$SO$_4$ and concentrated under reduced pressure. The crude product was purified by silica gel column chromatography (1:1 pet. ether/EtOAc) to afford the ester intermediates (E).

TABLE 7

Ester Intermediates (E)

| Compound | ID | Analytical Data | Yield |
|---|---|---|---|
| 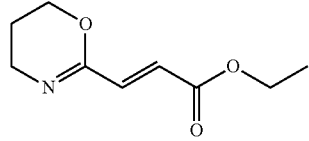 (E)-3-(5,6-Dihydro-4H- [1,3] oxazin-2-yl)-acrylic acid ethyl ester | E2 | MS (APCI); m/z 184 (MH$^+$); $^1$H NMR (d$^6$ DMSO) - δ 1.21-1.24 (t, 3H), δ 1.79-1.84 (m, 2H), δ 3.44-3.47 (t, 2H), δ 4.14-4.19 (q, 2H), δ 4.22-4.24 (t, 2H), δ 6.33-6.37 (d, 1H, J = 16.4 Hz), δ 6.64-6.68 (d, 1H, J = 16.4 Hz). | 1-5 g, 34% |
| 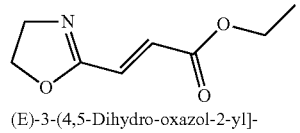 (E)-3-(4,5-Dihydro-oxazol-2-yl]-acrylic acid ethyl ester | E2 | MS (APCI); m/z 170 (MH$^+$); $^1$H NMR (CDCl$_3$) - δ 1.30-1.34 (t, 3H), δ 3.99-4.05 (t, 2H), δ 4.23-4.28 (q, 2H), δ 4.33-4.38 (t, 2H), δ 6.56-6.60 (d, 1H, J = 16.4 Hz), δ 7.09-7.13 (d, 1H, J = 16.4 Hz). | 750 mg, 34% |

1.2 General Procedures: Route A–F

1.2.1 Route A—General Procedure for Amide Synthesis

To the acid (1-1.2 equiv.) and TBTU (1-1.2 equiv.) in anhydrous DCM/DMF (2:1, 0.3M) was added DIPEA/anhydrous DCM, (1-1.2 equiv., 0.3 M). The reaction mixture was stirred at ambient temperature for 50 min. After this time, the amine/anhydrous DCM, (1 equiv., 0.14 M) was added and the reaction mixture stirred at ambient temperature overnight. To the reaction vessel was added tetrafluorophthalic anhydride (0.8-1 equiv.) in anhydrous DMF (0.48 M) and allowed to stir for 2-3 h to scavenge unreacted acid and TBTU. After this time, 2-3 equiv. MP-Carbonate was added and the reaction mixture stirred 6-12 h. The reaction mixture was applied to a preconditioned Si—NH$_2$ cartridge (1 or 2 g) and eluted with DMF (1×column volume) and MeOH (1×column volume). Evaporation of the eluents yielded the desired amide. In some instances, preparative LC-MS was required for purification.

1.2.2 Route B—General Procedure for Amide Synthesis

To a solution of the acid (1.2-1.5 equiv.) in DCM (0.28 M) was added TBTU (1.2-1.5 equiv.) and DIPEA (1.2-1.5 equiv.) The reaction was stirred at ambient temperature for 10 min followed by the addition of the amine (1 equiv.), and the reaction was stirred for 16 h at ambient temperature after which time the reaction was diluted with water (2 mL) and DCM (2 mL) and the organic phase collected by means of a phase separation cartridge. The solvent was removed under vacuum and the crude residue purified by preparative LC-MS to afford the desired compound.

1.2.3 Route C—General Procedure for Amide Synthesis

To a solution of the amine (1 equiv.) in toluene or DCE (0.4 M) was added trimethylaluminium (2 M in hexanes, 1 equiv.), and the reaction was stirred at ambient temperature for 30 min. This was followed by the addition of a solution of the ester (1 equiv.) in toluene or DCE (0.4 M), and the reaction was heated at 90° C. for 4 h after which time the reaction mixture was cooled to ambient temperature, diluted with water (20 mL) and extracted with EtOAc (3×20 mL). The combined organics were washed with brine (30 mL), dried over MgSO$_4$, filtered and the solvent removed under vacuum. The crude residue was triturated with DCM/hexane and dried. In some instances, the crude compound required purification by preparative LC-MS to afford the desired compound.

1.2.4 Route D—General Procedure for Amide Synthesis Via Acid Chloride

Step 1: To a solution of the acid (1 equiv.) in anhydrous DCM (0.46 M) and a catalytic amount of anhydrous DMF under a nitrogen atmosphere was added a 2 M solution of oxalyl chloride (1.1 equiv.) in anhydrous DCM. The reaction mixture was stirred at ambient temperature for 2 h. After this time, the reaction mixture was evaporated to dryness and re-dissolved in anhydrous DCM for direct use in step 2 below.

Step 2: To the amine (0.5-0.67 equiv.) was added a solution of pyridine in anhydrous DCM (3.7-5.15 M, 2.8 equiv.) followed by addition of a solution of the acid chloride in anhydrous DCM (0.3-0.37 M, 1 equiv.), synthesized in step 1, and the reaction mixture was purged with nitrogen and stirred at ambient temperature overnight.* To the reaction mixture was added DCM (3 mL) followed by water (4 mL). The mixture was agitated and passed through a phase-separation cartridge. DCM layer was further washed with water (4 mL). Organic layers were combined, evaporated to dryness, and compound was purified by preparative LC-MS.

* In some instances no work-up was performed, the reaction mixture was evaporated to dryness and purified by preparative LC-MS.

1.2.5 Route E—Amide Coupling

As Route A except amine was used in excess (1.5-2 equiv.). and 1 equiv. was used of all other reagents. In instances where the amine was a salt, amine was free-based with the addition of DIPEA prior to addition to the reaction mixture. In some instances, compounds required further purification via preparative LC-MS.

1.2.6 Route F—Ester Synthesis

To a microwave vial was added a solution of the acid in the alcohol (0.26 M, 1 equiv.) and conc. sulfuric acid (0.94 equiv.). The vial was sealed and heated in a microwave at 100° C. for 2 min. Reaction mixture was evaporated to dryness and purified by preparative LC-MS.

1.3 Final Compounds—Routes A—F

1.3.1 Final Compounds Synthesized by Route A

TABLE 8

Final Compounds Synthesized by Route A

| Compound | I<sub>HSF</sub> Int.* | Analytical Data | Yield |
|---|---|---|---|
| 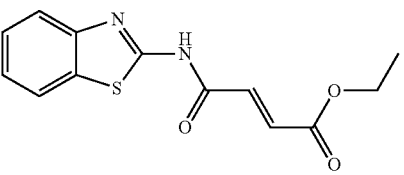 [SMILES: CCOC(=O)/C=C/C(=O)Nc1nc2ccccc2s1]<br>(E)-3-(Benzothiazol-2-ylcarbamoyl)-acrylic acid ethyl ester | 010 | AnalpH2_MeOH_QC; Rt 8.30 min (98%); m/z 277 (MH$^+$); $^1$H NMR (d$^6$-DMSO) - δ 1.25-1.29 (t, 3H), δ 4.21-4.26 (q, 2H), δ 6.86-6.89 (d, 1H, J = 15 Hz), δ 7.28-7.32 (d, 1H, J = 15 Hz), δ 7.32-7.36 (t of d, 1H), δ 7.44-7.49 (t of d, 1H), δ 7.78-7.80 (d of t, 1H), δ 8.00-8.03 (d of t, 1H) δ 12.92 (s, br, 1H); pale yellow solid | 18 mg, 88% |
| 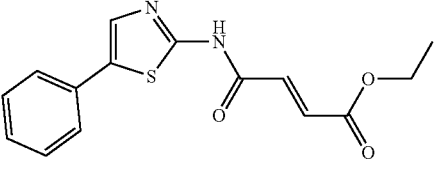 [SMILES: CCOC(=O)/C=C/C(=O)Nc1ncc(-c2ccccc2)s1]<br>(E)-3-(5-Phenyl-thiazol-2-ylcarbamoyl)-acrylic acid ethyl ester | 014 | AnalpH2_MeOH_QC; Rt 8.60 min (89%); m/z 303 (MH$^+$); yellow solid | 35.5 mg, 99% |
| 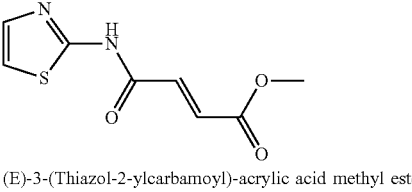<br>(E)-3-(Thiazol-2-ylcarbamoyl)-acrylic acid methyl ester | 027 | AnalpH2_MeOH_QC; Rt 6.45 min (99%); m/z 241 (MH$^+$); white solid | 9 mg, 7% |
| 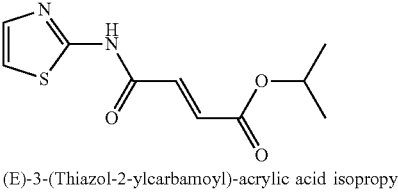<br>(E)-3-(Thiazol-2-ylcarbamoyl)-acrylic acid isopropyl ester | 028 | AnalpH2_MeOH_QC; Rt 7.54 min (97%); m/z 213 (MH$^+$); orange solid | 24 mg 56% |
| 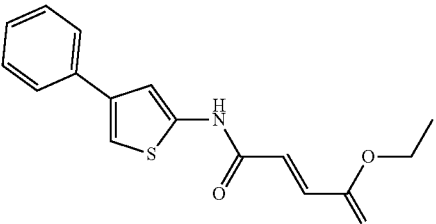<br>(E)-3-(4-Phenyl-thiophen-2-ylcarbamoyl)-acrylic acid ethyl ester | 043 | AnalpH2_MeCN_QC; Rt 7.38 min (99%); m/z 302 (MH$^+$); dark yellow solid | 4.1 mg 8% |
| 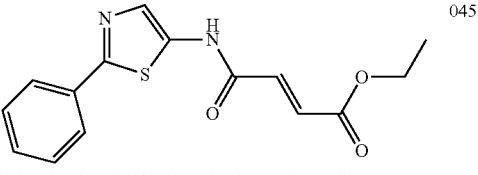<br>(E)-3-(2-Phenyl-thiazol-5-ylcarbamoyl)-acrylic acid ethyl ester | 045 | AnalpH2_MeOH_QC; Rt 8.34 min (99%); m/z 303 (MH$^+$); $^1$H NMR (d$^6$-DMSO) - δ 1.26-1.29 (t, 3H), δ 4.2-4.26 (q, 2H), δ 6.76-6.80 (d, 1H, J = 15 Hz), δ 7.14-7.18 (d, 1H, J = 15 Hz), δ 7.42-7.50 (m, 3H), δ 7.71 (s, 1H), δ 7.89-7.91 (d of t, 2H), δ 12.21 (s, br, 1H); yellow solid | 11.6 mg 21% |

TABLE 8-continued

Final Compounds Synthesized by Route A

| Compound | $I_{HSF}$ Int.* | Analytical Data | Yield |
|---|---|---|---|
| 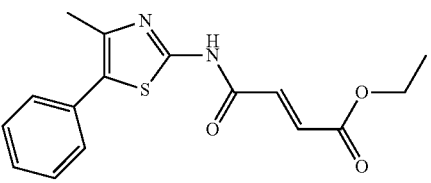 [SMILES: CCOC(=O)/C=C/C(=O)Nc1nc(C)c(-c2ccccc2)s1]<br>(E)-3-(4-Methyl-5-phenyl-thiazol-2-ylcarbamoyl)-acrylic acid ethyl ester | 051 | AnalpH2_MeOH_QC; Rt 8.75 min (87%); m/z 317 (MH$^+$); yellow solid | 45 mg 79% |
| 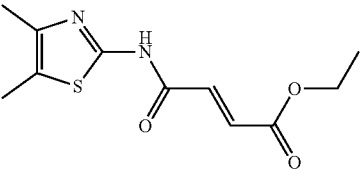 [SMILES: CCOC(=O)/C=C/C(=O)Nc1nc(C)c(C)s1]<br>(E)-3-(4,5-Dimethyl-thiazol-2-ylcarbamoyl)-acrylic acid ethyl ester | 052 | AnalpH2_MeOH_QC; Rt 7.90 min (93%); m/z 255 (MH$^+$); yellow solid | 36 mg 78% |
| 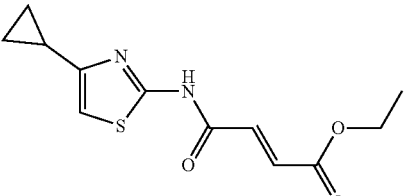<br>(E)-3-(4-Cyclopropyl-thiazol-2-ylcarbamoyl)-acrylic acid ethyl ester | 053 | AnalpH2_MeOH_QC; Rt 8.05 min (89%); m/z 267 (MH$^+$); yellow/brown solid | 38 mg 79% |
| 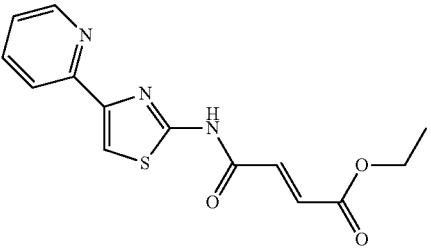 [SMILES: CCOC(=O)/C=C/C(=O)Nc1nc(-c2ccccn2)cs1]<br>(E)-3-(4-Pyridin-2-yl-thiazol-2-yl carbamoyl)-acrylic acid ethyl ester | 054 | AnalpH2_MeOH_QC; Rt 7.18 min (96%); m/z 304 (MH$^+$); $^1$H NMR (d$^6$-DMSO) - δ 1.26-1.29 (t, 3H), δ 4.21-4.26 (q, 2H), δ 6.84-6.88 (d, 1H, J = 15.4 Hz), δ 7.28-7.31 (d, 1H, J = 15.4 Hz), δ 7.34-7.38 (dqd, 1H), δ 7.89-7.97 (m, 3H), δ 8.61-8.63 (d of q, 1H), δ 12.95 (s, br, 1H); brown/yellow solid | 40 mg 74% |
| 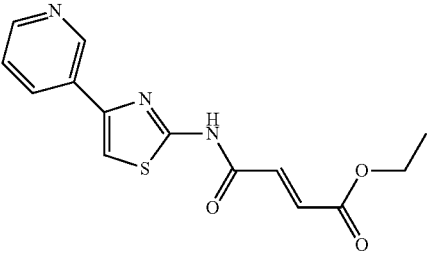 [SMILES: CCOC(=O)/C=C/C(=O)Nc1nc(-c2cccnc2)cs1]<br>(E)-3-(4-Pyridin-3-yl-thiazol-2-yl carbamoyl)-acrylic acid ethyl ester | 055 | AnalpH2_MeOH_QC; Rt 7.02 min (86%); m/z 304 (MH$^+$); yellow solid | 15 mg 27% |

TABLE 8-continued

Final Compounds Synthesized by Route A

| Compound | $I_{HSF}$ Int.* | Analytical Data | Yield |
|---|---|---|---|
| 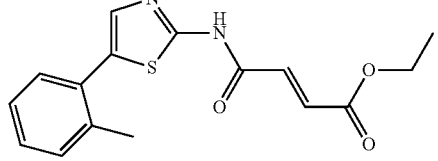<br>(E)-3-(5-o-Tolyl-thiazol-2-ylcarbamoyl)-acrylic acid ethyl ester | 059 AH1 | AnalpH2_MeCN_QC; Rt 7.54 min (89%); m/z 317 (MH+); $^1$H NMR (d$^6$-DMSO) δ 1.32-1.35 (t, 3H), δ 2.47 (s, 3H), δ 4.27-4.32 (q, 2H), δ 6.88-6.92 (d, 1H, J = 15.6 Hz), δ 7.33-7.37 (d, 1H, J = 15.6 Hz), δ 7.34-7.38 (m, 2H), δ 7.40-7.42 (d of m, 1H), δ 7.46-7.48 (d of d, 1H), δ 7.71 (s, 1H), δ 12.88 (s, br, 1H); yellow solid | 19 mg 66% |
| 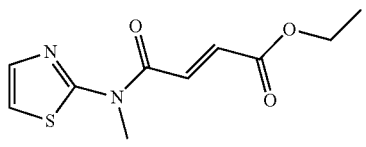 [SMILES: CCOC(=O)/C=C/C(=O)N(C)c1nccs1]<br>(E)-3-(Methyl-thiazol-2-yl-carbamoyl)-acrylic acid ethyl ester | 070 | AnalpH2_MeOH_QC; Rt 7.32 min (92%); m/z 241 (MH+); $^1$H NMR (d$^6$-DMSO) δ 1.26-1.3 (t, 3H), δ 3.78 (s, 3H), δ 4.22-4.27 (q, 2H), δ 6.78-6.82 (d, 1H, J = 15.4 Hz), δ 7.38-7.39 (d, 1H), δ 7.60-7.61 (d, 1H), δ 7.62-7.66 (d, 1H, J = 15.4 Hz); yellow solid | 36 mg 75% |

* Where the intermediate column is left blank, the starting material(s) was/were commercially available.

1.3.2 Final Compounds Synthesized by Route B

TABLE 9

Final Compounds Synthesized by Route B

| Compound | $I_{HSF}$ Int. | Analytical Data | Yield |
|---|---|---|---|
| 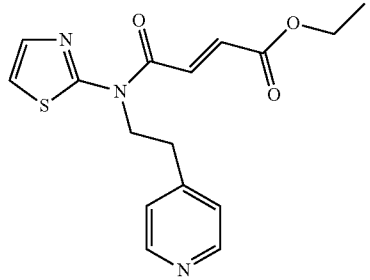 [SMILES: CCOC(=O)/C=C/C(=O)N(CCc1ccncc1)c1nccs1]<br>(E)-3-[(2-Pyridin-4-yl-ethyl)-thiazol-2-yl-carbamoyl]-acrylic acid ethyl ester | 099 AH4 | AnalpH2_MeOH_QC; Rt 5.75 min (90%); m/z 332 (MH+); $^1$H NMR (d$^6$-DMSO) - δ 1.26 (t, 3H), δ 3.03-3.07 (t, 2H), δ 4.19-4.24 (q, 2H), δ 4.57-4.60 (t, 2H), δ 6.54-6.58 (d, 1H, J = 15.2 Hz), δ 7.17-7.18 (d, 2H), δ 7.34-7.42 (d, 1H, J = 15.2 Hz), δ 7.43-7.44 (d, 1H), δ 7.66-7.67 (d, 1H), δ 8.43-8.44 (d of d, 2H); beige solid | 5.2 mg 5% |
| 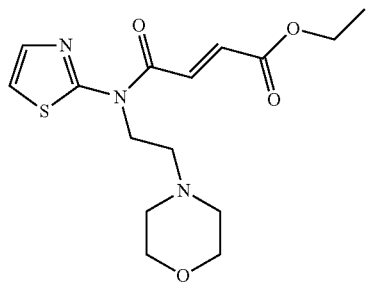 [SMILES: CCOC(=O)/C=C/C(=O)N(CCN1CCOCC1)c1nccs1]<br>(E)-3-[(2-Morpholin-4-yl-ethyl)-thiazol-2-yl-carbamoyl]-acrylic acid ethyl ester | 101 AH5 | AnalpH2_MeOH_QC; Rt 4.6 min (92%); m/z 340 (MH+); $^1$H NMR (d$^6$-DMSO) - δ 1.06-1.09 (t, 3H), δ 2.19-2.22 (t, 4H), δ 2.38-2.41 (t, 2H), δ 3.28-3.30 (t, 4H), δ 4.02-4.07 (q, 2H), δ 4.21-4.23 (t, 2H), δ 6.61-6.65 (d, 1H, J = 15 Hz), δ 7.2-7.21 (d, 1H), δ 7.41-7.42 (d, 1H), δ 7.51-7.55 (d, 1H, J = 15 Hz); cream solid | 30.6 mg 45% |

TABLE 9-continued

Final Compounds Synthesized by Route B

| Compound | $I_{HSF}$ | Int. | Analytical Data | Yield |
|---|---|---|---|---|
| 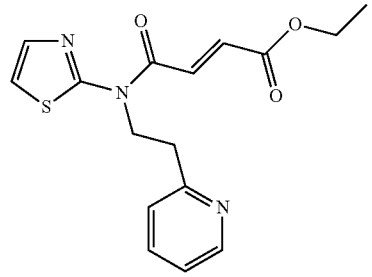 [SMILES: CCOC(=O)/C=C/C(=O)N(CCc1ccccn1)c1nccs1]<br>(E)-3-[(2-Pyridin-2-yl-ethyl)-thiazol-2-yl-carbamoyl]-acrylic acid ethyl ester | 112 | AH6 | AnalpH2_MeOH_QC; Rt 6.16 min (89%); m/z 332 (MH+); orange solid | 2.4 mg 4% |
| 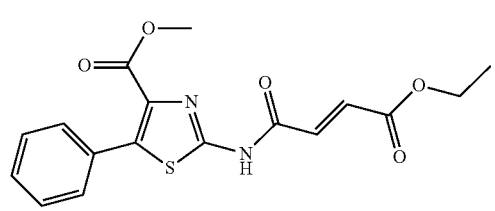 [SMILES: CCOC(=O)/C=C/C(=O)Nc1nc(C(=O)OC)c(-c2ccccc2)s1]<br>2-((E)-3-Ethoxycarbonyl-acryloylamino)-5-phenyl-thiazole-4-carboxylic acid methyl ester | 105 | AH8 | AnalpH2_MeOH_QC; Rt 8.43 min (>95%); m/z 361 (MH+); pale gold solid | 3.5 mg 6% |
| 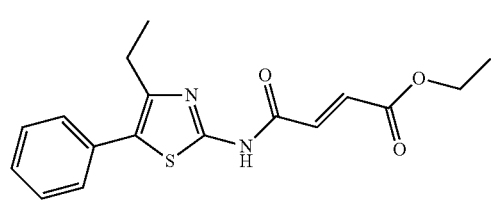 [SMILES: CCOC(=O)/C=C/C(=O)Nc1nc(CC)c(-c2ccccc2)s1]<br>(E)-3-(4-Ethyl-5-phenyl-thiazol-2-ylcarbamoyl)-acrylic acid ethyl ester | 107 | AH9 | AnalpH2_MeOH_QC; Rt 8.79 min (>95%); m/z 331 (MH+); pale lemon solid | 11.2 mg 3.5% |
| 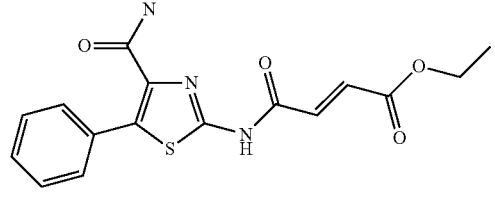 [SMILES: CCOC(=O)/C=C/C(=O)Nc1nc(C(N)=O)c(-c2ccccc2)s1]<br>(E)-3-(4-Carbamoyl-5-phenyl-thiazol-2-ylcarbamoyl)-acrylic acid ethyl ester | 109 | AH10 | AnalpH2_MeOH_QC; Rt 7.9 min (>95%); m/z 346 (MH+); $^1$H NMR (d$^6$-DMSO) - δ 1.39-1.43 (t, 3H), δ 4.35-4.40 (q, 2H), δ 6.97-7.01 (d, 1H, J = 15.5 Hz), δ 7.40-7.44 (d, 1H, J = 15.5 Hz), δ 7.52-7.59 (m, 3H), δ 7.65 (s, br, 1H), δ 7.69-7.71 (d of t, 2H), δ 13.07 (s, br, 2H); yellow solid | 6.3 mg 10% |

1.3.3 Final Compounds Synthesised by Route C

TABLE 10

Compounds Synthesised by Route C

| Compound | $I_{HSF}$ Int. | Analytical Data | Yield |
|---|---|---|---|
| 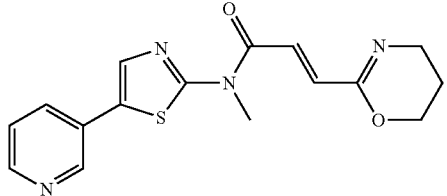 [SMILES: CN(C(=O)/C=C/C1=NCCCO1)c1ncc(-c2cccnc2)s1]<br>(E)-3-(5,6-Dihydro-4H-[1,3]oxazin-2-yl)-N-methyl-N-(5-pyridin-3-yl-thiazol-2-yl)-acrylamide | 115 AH3, E1 | AnalpH9_MeOH _QC; Rt 7.19 min (99.2); m/z 329 (MH$^+$);$^1$ H NMR (d$^6$-DMSO) - δ 1.83-1.89 (m, 2H), δ 3.48-3.51 (t, 2H), δ 3.79 (s, 3H), δ 4.28-4.30 (t, 2H), δ 6.77-6.80 (d, 1H, J = 15.4 Hz), δ 7.23-7.27 (d, 1H, J = 15.4 Hz), δ 7.44-7.48 (q of d, 1H), δ 8.04-8.07 (d of t, 1H), δ 8.13 (s, 1H), δ 8.51-8.52 (d of d, 1H), δ 8.89-8.90 (d, 1H); cream solid | 259 mg 21.5% |
| 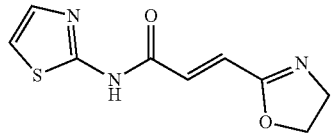 [SMILES: O=C(/C=C/C1=NCCO1)Nc1nccs1]<br>(E)-3-(5,6-Dihydro-4H-[1,3]oxazin-2-yl)-N-thiazol-2-yl-acrylamide | 090 E1 | Method_4_TFA_UPLC_2; Rt 1.94 min (96%); m/z 238 (MH$^+$); $^1$H NMR (CD$_3$CO$_2$D) - δ 2.29-2.31 (t, 2H), δ 3.79-3.82 (t, 2H), δ 4.78-4.80 (t, 2H), 87.17-7.21 (d, 1H, J = 15.6 Hz), δ 7.22-7.23 (d, 1H), δ 7.36-7.40 (d, 1H, J = 15.6 Hz), δ 7.53-7.54 (d, 1H); mp - 205-208° C; pale brown solid | 38 mg, 9% |
| 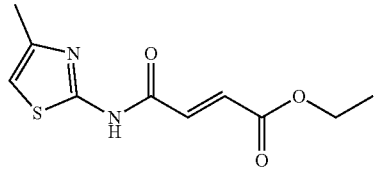<br>(E)-3-(4,5-Dihydro-oxazol-2-yl)-N-thiazol-2-yl-acrylamide | 092 E2 | Method_4_TFA_UPLC_2; Rt 2.30 min (88%); m/z 224 (MH$^+$); $^1$H NMR (CD$_3$CO$_2$D) - δ 4.06-4.11 (t, 2H), δ 4.53-4.58 (t, 2H), δ 6.94-6.98 (d, 1H, J = 16 Hz), 87.19-7.20 (d, 1H), 87.32-7.36 (d, 1H, J = 16 Hz), 87.50-7.51 (d, 1H); mp - 221-226° C.; yellow solid | 38 mg, 9% |

1.3.4 Final Compounds Synthesised by Route D

TABLE 11

Final Compounds Synthesised by Route D

| Compound | ID | Int. | Analytical Data | Yield |
|---|---|---|---|---|
| 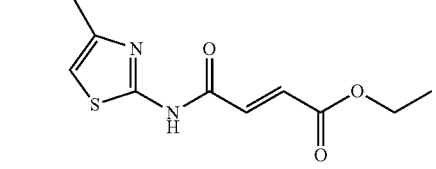<br>(E)-3-(4-Methyl-thiazol-2-ylcarbamoyl)-acrylic acid ethyl ester | 011 | | AnalpH2_MeOH_QC; Rt 7.51 min (95%); m/z 241 (MH$^+$); $^1$H NMR (d$^6$-DMSO) - δ 1.25-1.29 (t, 3H), δ 2.29 (d, 3H) δ 4.20-4.25 (q, 2H), δ 6.79-6.83 (d, 1H, J = 15 Hz), 86.87 (d, 1H) δ 7.21-7.25 (d, 1H, J = 15 Hz), δ 12.61 (s, br, 1H); yellow solid | 31 mg, 64% |
| (E)-3-(4-Phenyl-thiazol-2-ylcarbamoyl)-acrylic acid ethyl ester | 012 | | AnalpH2_MeOH_QC; Rt 8.48 min (100%); m/z 303 (MH$^+$); tan solid | 24 mg, 40% |

TABLE 11-continued

Final Compounds Synthesised by Route D

| Compound | ID Int. | Analytical Data | Yield |
|---|---|---|---|
| 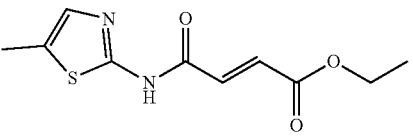 [SMILES: CCOC(=O)/C=C/C(=O)Nc1ncc(C)s1]<br>(E)-3-(5-Methyl-thiazol-2-ylcarbamoyl)-acrylic acid ethyl ester | 013 | AnalpH2_MeOH_QC; Rt 7.58 min (100%); m/z 241 (MH$^+$); yellow solid | 21 mg, 44% |
| 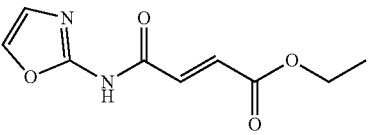<br>(E)-3-(Oxazol-2-ylcarbamoyl)-acrylic acid ethyl ester | 015 | AnalpH9_MeOH_QC; Rt 5.27 min (88%); m/z 211 (MH$^+$); cream solid | 21 mg 51% |
| 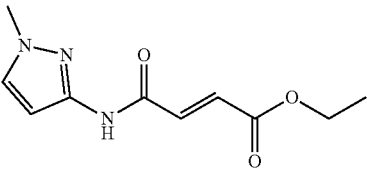 [SMILES: CCOC(=O)/C=C/C(=O)Nc1ccn(C)n1]<br>(E)-3-(1-Methyl-1H-pyrazol-3-ylcarbamoyl)-acrylic acid ethyl ester | 016 | AnalpH2_MeOH_QC; Rt 6.30 min (100%); m/z 224 (MH$^+$); cream solid | 32 mg 73% |
| 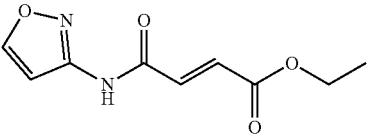<br>(E)-3-(Isoxazol-3-ylcarbamoyl)-acrylic acid ethyl ester | 017 | AnalpH2_MeOH_QC; Rt 6.48 min (100%); m/z 211 (MH$^+$); cream solid<br>$^1$H NMR (d$^6$-DMSO) - δ 1.25-1.28 (t, 3H), δ 4.2-4.25 (q, 2H), δ 6.76-6.80 (d, 1H, J = 15.7 Hz), δ 7.0-7.01 (d, 1H) δ 7.20-7.24 (d, 1H, J = 15.7 Hz), δ 8.85-8.86 (d, 1H), δ 11.63 (s, br, 1H) | 33 mg 79% |
| 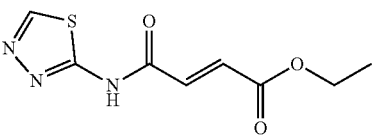<br>(E)-3-([1,3,4]Thiadiazol-2-yl carbamoyl)-acrylic acid ethyl ester | 018 | AnalpH2_MeOH_QC; Rt 6.50 min (100%); m/z 228 (MH$^+$); tan solid | 13 mg 29% |
| 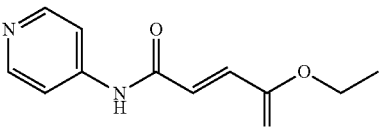<br>(E)-3-(Pyridin-4-ylcarbamoyl)-acrylic acid ethyl ester | 020 | AnalpH2_MeOH_QC; Rt 4.16 min (98%); m/z 221 (MH$^+$); pale yellow solid | 7 mg 15% |
| 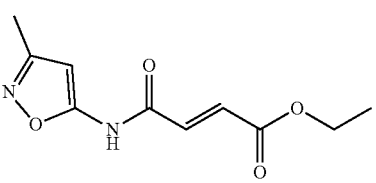 [SMILES: CCOC(=O)/C=C/C(=O)Nc1cc(C)no1]<br>(E)-3-(3-Methyl-isoxazol-5-ylcarbamoyl)-acrylic acid ethyl ester | 046 | AnalpH2_MeCN_QC; Rt 5.52 min (100%); m/z 225 (MH$^+$); $^1$H NMR (d$^6$-DMSO) δ 1.24-1.28 (t, 3H), δ 2.20 (s, 3H), δ 4.19-4.24 (q, 2H), δ 6.27 (s, 1H), δ 6.76-6.80 (d, 1H, J = 15.4 Hz), δ 7.13-7.17 (d, 1H, J = 15.4 Hz), δ 12.15 (s, br, 1H);<br>pale brown solid | 28 mg 62% |

TABLE 11-continued

Final Compounds Synthesised by Route D

| Compound | ID | Int. | Analytical Data | Yield |
|---|---|---|---|---|
| (E)-3-(2-Methyl-pyridin-4-ylcarbamoyl)-acrylic acid ethyl ester | 048 | | AnalpH2_MeCN_QC; Rt 5.30 min (100%); m/z 235 (MH+); pale brown solid | 14 mg 30% |
| (E)-3-(2-Phenyl-pyridin-4-ylcarbamoyl)-acrylic acid ethyl ester | 049 | | AnalpH2_MeCN_QC; Rt 6.82 min (97%); m/z 297 (MH+); pale brown solid | 37 mg 63% |
| (E)-3-(Quinolin-4-ylcarbamoyl)-acrylic acid ethyl ester | 050 | | AnalpH2_MeCN_QC; Rt 5.91 min (86%); m/z 271 (MH+); pale brown solid | 25 mg 46% |
| (E)-3-(4-Pyridin-4-yl-thiazol-2-lcarbamoyl)-acrylic acid ethyl ester | 056 | | AnalpH2_MeCN_QC; Rt 6.02 min (87%); m/z 304 (MH+); pale orange solid | 10 mg 16% |
| (E)-3-(5-Cyano-thiazol-2-yl carbamoyl)-acrylic acid ethyl ester | 057 | | AnalpH2_MeCN_QC; Rt 4.27 min (99%); m/z 252 (MH+); $^1$H NMR (d$^6$-DMSO) δ 1.33-1.37 (t, 3H), δ 4.29-4.34 (q, 2H), δ 6.95-6.99 (d, 1H, J = 15.4 Hz), δ 7.30-7.34 (d, 1H, J = 15.4 Hz), δ 8.54 (s, 1H), δ 13.57 (s, br, 1H); pale brown solid | 21 mg 42% |
| (E)-3-(5-Pyridm-3-yl-thiazol-2-ylcarbamoyl)-acrylic acid ethyl ester | 058 | AH2 | AnalpH2_MeCN_QC; Rt 4.28 min (99%); m/z 304 (MH+); $^1$H NMR (DMSO-d6): δ 12.91 (brs, 1H), 8.89 (dd, J = 2.3, 0.8 Hz, 1H), 8.51 (dd, J = 4.8, 1.5 Hz, 1H), 8.11 (s, 1H), 8.07-8.04 (m, 1H), 7.48-7.44 (m, 1H), 7.28 (d, J = 15.5 Hz, 1H), 6.86 (d, J = 15.5 Hz, 1H), 4.23 (q, J = 7.2 Hz, 2H), 1.27 (t, J = 7.2 Hz, 3H); pale brown solid | 9 mg 43% |

TABLE 11-continued

Final Compounds Synthesised by Route D

| Compound | ID Int. | Analytical Data | Yield |
|---|---|---|---|
| 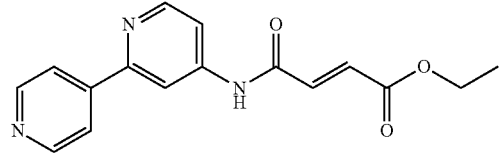<br>(E)-3-([2,4']Bipyridinyl-4-ylcarbamoyl)-acrylic acid ethyl ester | 076 | AnalpH2_MeOH_QC; Rt 6.56 min (100%); m/z 298 (MH$^+$); $^1$H NMR (d$^6$-DMSO) δ 1.26-1.30 (t, 3H), δ 4.21-4.26 (q, 2H), δ 6.78-6.81 (d, 1H, J = 15.4 Hz), δ 7.20-7.24 (d, 1H, J = 15.4 Hz), δ 7.67-7.69 (d of d, 1H), δ 7.93-7.95 (d of d, 2H), 8.31 (d, 1H), δ 8.65-8.67 (d, 1H), δ 8.72-8.73 (d of d, 2H), δ 11.14 (s, br, 1H); beige solid | 21 mg 36% |
| 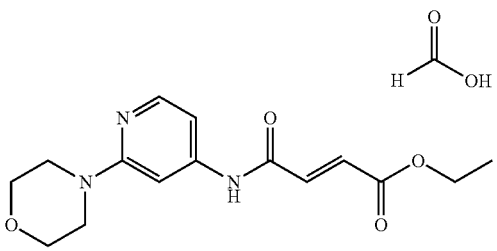<br>(E)-3-(2-Morpholin-4-yl-pyridin-4-ylcarbamoyl)-acrylic acid ethyl ester formic acid salt | 077 | AnalpH2_MeOH_QC; Rt 5.08 min (100%); m/z 306 (MH$^+$); $^1$H NMR (d$^6$-DMSO) δ 1.25-1.29 (1, 3H), δ 3.37-3.39 (m, 4H), δ 3.69-3.71 (m, 4H) δ 4.20-4.25 (q, 2H), δ 6.70-6.74 (d, 1H, J = 15.4 Hz), δ 6.87-6.89 (d of d, 1H) δ 7.16-7.20 (d, 2H, J = 15.4 Hz), δ 8.05-8.06 (d, 1H), δ 8.16 (s, 1H), δ 10.71 (s, br, 1H), δ 12.83 (s, br, 1H); pale yellow solid | 42 mg 60% |
| 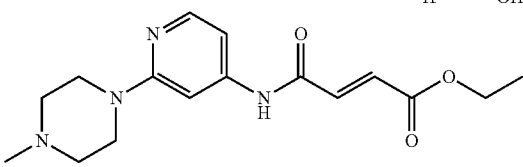<br>(E)-3-[2-(4-Methyl-piperazin-1-yl)-pyridin-4-ylcarbamoyl]-acrylic acid ethyl ester formic acid salt | 078 | AnalpH2_MeOH_QC; Rt 3.88 min (95%); m/z 319 (MH$^+$); yellow solid | 29 mg 40% |
| 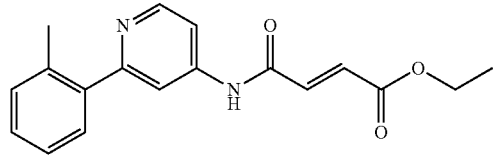 [SMILES: CCOC(=O)/C=C/C(=O)Nc1ccnc(-c2ccccc2C)c1]<br>(E)-3-(2-o-Tolyl-pyridin-4-ylcarbamoyl)-acrylic acid ethyl ester | 079 | AnalpH2_MeOH_QC; Rt 6.78 min (97%); m/z 311 (MH$^+$); tan solid | 40 mg 65% |

TABLE 11-continued

Final Compounds Synthesised by Route D

| Compound | ID Int. | Analytical Data | Yield |
|---|---|---|---|
| 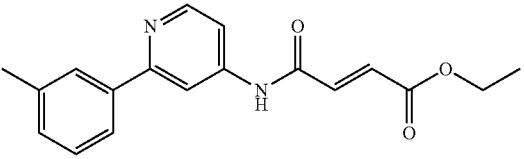 [SMILES: CCOC(=O)/C=C/C(=O)Nc1ccnc(-c2cccc(C)c2)c1]<br>(E)-3-(2-m-Tolyl-pyridin-4-ylcarbamoyl)-acrylic acid ethyl ester | 080 | AnalpH2_MeOH_QC; Rt 7.43 min (100%); m/z 311 (MH$^+$); pale brown solid | 46 mg 74% |
| 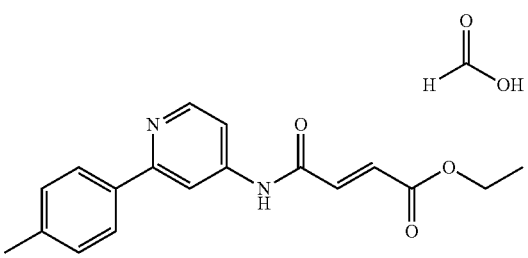<br>(E)-3-(2-p-Tolyl-pyridin-4-ylcarbamoyl)-acrylic acid ethyl ester formic acid salt | 081 | AnalpH2_MeOH_QC; Rt 7.23 min (99%); m/z 311 (MH$^+$); tan solid<br>$^1$H NMR (d$^6$-DMSO) δ 1.26-1.30 (t, 3H), δ 2.37 (s, 3H), δ 4.21-4.26 (q, 2H), δ 6.76-6.80 (d, 1H, J = 15.6 Hz), δ 7.20-7.24 (d, 1H, J = 15.4 Hz), δ 7.31-7.33 (d, 2H), δ 7.53-7.55 (d of d, 1H), δ 7.88-7.9 (d, 2H), δ 8.15 (s, 1H), δ 8.16-8.17 (d, 1H), δ 8.55-8.56 (d, 1H), δ 10.99 (s, 1H), δ 12.95 (s, br, 1H) | 39 mg 55% |
| 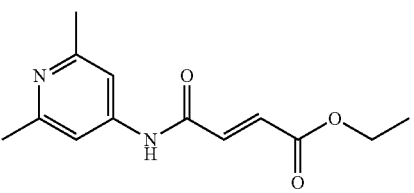 [SMILES: CCOC(=O)/C=C/C(=O)Nc1cc(C)nc(C)c1]<br>(E)-3-(2,6-Dimethyl-pyridin-4-ylcarbamoyl)-acrylic acid ethyl ester | 082 | AnalpH2_MeOH_QC; Rt 4.53 min (88%); m/z 249 (MH$^+$); yellow solid | 9 mg 18% |
| 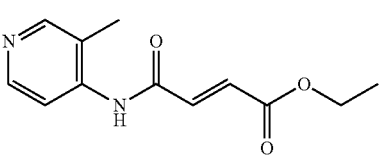 [SMILES: CCOC(=O)/C=C/C(=O)Nc1ccncc1C]<br>(E)-3-(3-Methyl-pyridin-4-ylcarbamoyl)-acrylic acid ethyl ester | 083 | AnalpH2_MeOH_QC; Rt 4.17 min (88%); m/z 235 (MH$^+$); off-white solid | 15 mg 32% |
| 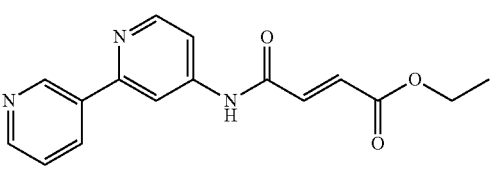 [SMILES: CCOC(=O)/C=C/C(=O)Nc1ccnc(-c2cccnc2)c1]<br>(E)-3-([2,3']Bipyridmyl-4-ylcarbamoyl)-acrylic acid ethyl ester | 086 | AnalpH2_MeOH_QC; Rt 6.92 min (100%); m/z 298 (MH$^+$); tan solid | 28 mg 47% |

*Where the intermediate column is left blank, the starting material(s) was/were commercially available.

Synthesis of Final Compound 108 via Amino Heterocycle Intermediate AH7: (E)-3-{[2-1-Methyl-1H-imidazol-4-yl)-ethyl]-thiazol-2-yl-carbamoyl}-acrylic Acid Ethyl Ester

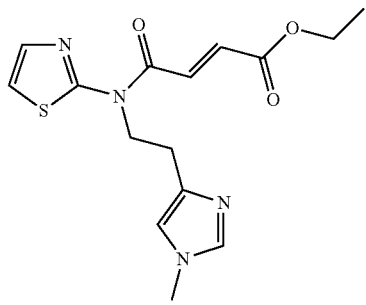 [SMILES: CCOC(=O)/C=C/C(=O)N(CCc1cn(C)cn1)c1nccs1]

To a solution of [2-(1-Methyl-1H-imidazol-4-yl)-ethyl]-2-yl-amine (thiazole intermediate AH7), (120 mg, 1 equiv., 0.57 mmol) in DCM (1 mL) was added ethyl fumaroyl chloride (70 µL, 1.1 equiv., 0.63 mmol), dropwise, and triethylamine (204 µL, 3 equiv., 1.72 mmol), and the reaction was stirred at ambient temperature for 1 h after which time the solvent was removed and the crude residue purified by preparative LC-MS to afford the title compound, $I_{HSF}$ 108 as a golden colored glass (3.4 mg, 1.78%). AnalpH2_MeOH_QC; Rt 4.51 min (>95%); m/z 335 (MH$^+$).

1.3.5 Final Compounds Synthesised by Route E

TABLE 12

Final Compounds Synthesised by Route E

| Compound | $I_{HSF}$ Int. | Analytical Data | Yield |
|---|---|---|---|
| (E)-But-2-enedioic acid ethylamide thiazol-2-ylamide | 030 A1 | AnalpH2_MeOH_QC; Rt 5.90 min (85%); m/z 226 (MH$^+$); beige solid | 34 mg, 89% |
| (E)-But-2-enedioic acid isopropylamide thiazol-2-ylamide | 031 A1 | AnalpH2_MeOH_QC; Rt 6.40 min (98%); m/z 240 (MH$^+$); beige solid | 36 mg, 90% |
| (E)-But-2-enedioic acid diethyl-amide (4-methyl-thiazol-2-yl)-amide | 060 A2 | AnalpH2_MeOH_QC; Rt 7.20 min (95%); m/z 268 (MH$^+$); pale brown solid | 26 mg, 58% |
| (E)-But-2-enedioic acid dimethyl-amide (4-methyl-thiazol-2-yl)-amide | 061 A2 | AnalpH2_MeOH_QC; Rt 6.38 min (98%); m/z 240 (MH$^+$); $^1$H NMR (d$^6$-DMSO) - δ 2.37 (s, 3H), δ 3.02 (s, 3H), δ 3.20 (s, 3H), δ 6.93 (s, 1H), δ 7.09-7.12 (d, 1H, J = 15.1 Hz), δ 7.57-7.61 (d, 1H, J = 15.1 Hz), δ 12.61 (s, br, 1H); off-white solid | 5 mg, 13% |

1.3.6 Final Compounds Synthesised by Route F

TABLE 13

Final Compounds Synthesised by Route F

| Compound | $I_{HSF}$ Int.* | Analytical Data | Yield |
|---|---|---|---|
| (E)-3-(Thiazol-2-ylcarbamoyl)-acrylic acid butyl ester | 042 | AnalpH2_MeCN_QC; Rt 5.98 min (100%); m/z 255 (MH+); $^1$H NMR (CDCl$_3$) - δ 0.85-0.89 (t, 3H), δ 1.28-1.37 (m, 2H), δ 1.57-1.64 (m, 2H), δ 4.18-4.22 (t, 2H) δ 6.27-6.30 (d, 1H, J = 13.4 Hz), δ 6.44-6.47 (d, 1H, J = 13.4 Hz), δ 6.93-6.94 (d, 1H), δ 7.44-7.45 (d, 1H) δ 12.90 (s, br, 1H); white solid | 15 mg, 46% |

*Where the intermediate column is left blank, the starting material(s) was/were commercially available.

1.4 Final Compounds Route G 1.4.1 Synthesis of Final Compounds Via Route G

Synthesis of Acid Intermediate (A1):

Step 1: (E)-Ethyl-4-oxo-4-(thiazol-2-ylamino)-but-2-enoate. To a stirred solution of fumaric acid monoethyl ester (1 g, 6.94 mmol) in DCM (100 mL) at 0° C. was added EDC (1.6 g, 8.33 mmol), HOBt (1.14 g, 8.33 mmol) and 2-aminothiazole (694 mg, 6.94 mmol) sequentially and stirred at ambient temperature for 16 h. The reaction mixture was diluted with water, and extracted with DCM (2×200 mL). The combined organics were washed with water (2×100 mL), brine (2×100 mL), dried over Na$_2$SO$_4$ and concentrated in vacuo. The crude compound was purified by column chromatography (silica gel, 100-200 mesh, EtOAc/pet. ether) to afford (E)-ethyl 4-oxo-4-(thiazol-2-yl)amino-2-enoate as a pale yellow solid (500 mg, 32%). R$_f$: 0.4 (20% EtOAc/pet. ether). $^1$H NMR (d$^6$ DMSO) –δ1.23-1.28 (t, 3H), δ4.19-4.25 (q, 2H), δ6.8-6.84 (d, 1H), δ7.25-7.29 (d, 1H), δ7.33-7.34 (d, 1H), δ7.55-7.56 (d, 1H), δ12.72 (s, br, 1H).

Step 2: (E)-4-Oxo-4-(thiazol-2-ylamino)-but-2-enoic acid (Acid Intermediate A1). To a solution of (E)-ethyl 4-oxo-4-(thiazol-2-ylamino)-but-2-enoate (500 mg, 2.37 mmol) in THF/water (1:1) was added LiOH (199 mg, 4.74 mmol) and stirred at ambient temperature for 2 h. The reaction mixture was concentrated in vacuo, and the residue was acidified with sat. aq. KHSO$_4$, diluted with water, and the precipitated solid was collected by filtration to afford (E)-4-oxo-4-(thiazol-2-ylamino)-but-2-enoic acid (acid intermediate A1) as a pale yellow solid (350 mg, 75%). R$_f$: 0.1 (10% MeOH/CHCl$_3$). $^1$H NMR (d$^6$ DMSO) –δ6.75-6.79 (d, 1H), δ7.17-7.21 (d, 1H), δ7.32-7.33 (d, 1H), δ7.55-7.56 (d, 1H), δ12.72 (s, br, 1H), δ13.16 (s, br, 1H).

Synthesis of Final Compound $I_{HSF}$ 089 Via Acid Intermediate A1:

Step 3: N$^1$-(Thiazol-2-yl)fumaramide. To a stirred suspension of (E)-4-oxo-4-(thiazol-2-ylamino)but-2-enoic acid (A1) (200 mg, 1.01 mmol) in dry THF at –40° C. was added NMM (122 mg, 1.21 mmol) and isobutyl chloroformate (166 mg, 1.21 mmol), and the reaction was stirred for 20 min. Ammonium carbonate (484 mg, 5.05 mmol) was added, and the reaction mixture was allowed to warm to ambient temperature over 2 h. The solvent was evaporated in vacuo, and the residue was diluted with water. The precipitated solid was collected by filtration, and washed with Et$_2$O to obtain N$^1$-(thiazol-2-yl)fumaramide as a light brown solid (180 mg, 90%). R$_f$: 0.2 (10% MeOH/CHCl$_3$). $^1$H NMR (d$^6$ DMSO) –δ7.07 (s, br, 2H), 67.3-7.31 (d, 1H), δ7.50 (s, br, 1H), δ7.54-7.55 (d, 1H), δ7.95 (s, br, 1H), δ12.62 (s, br, 1H)

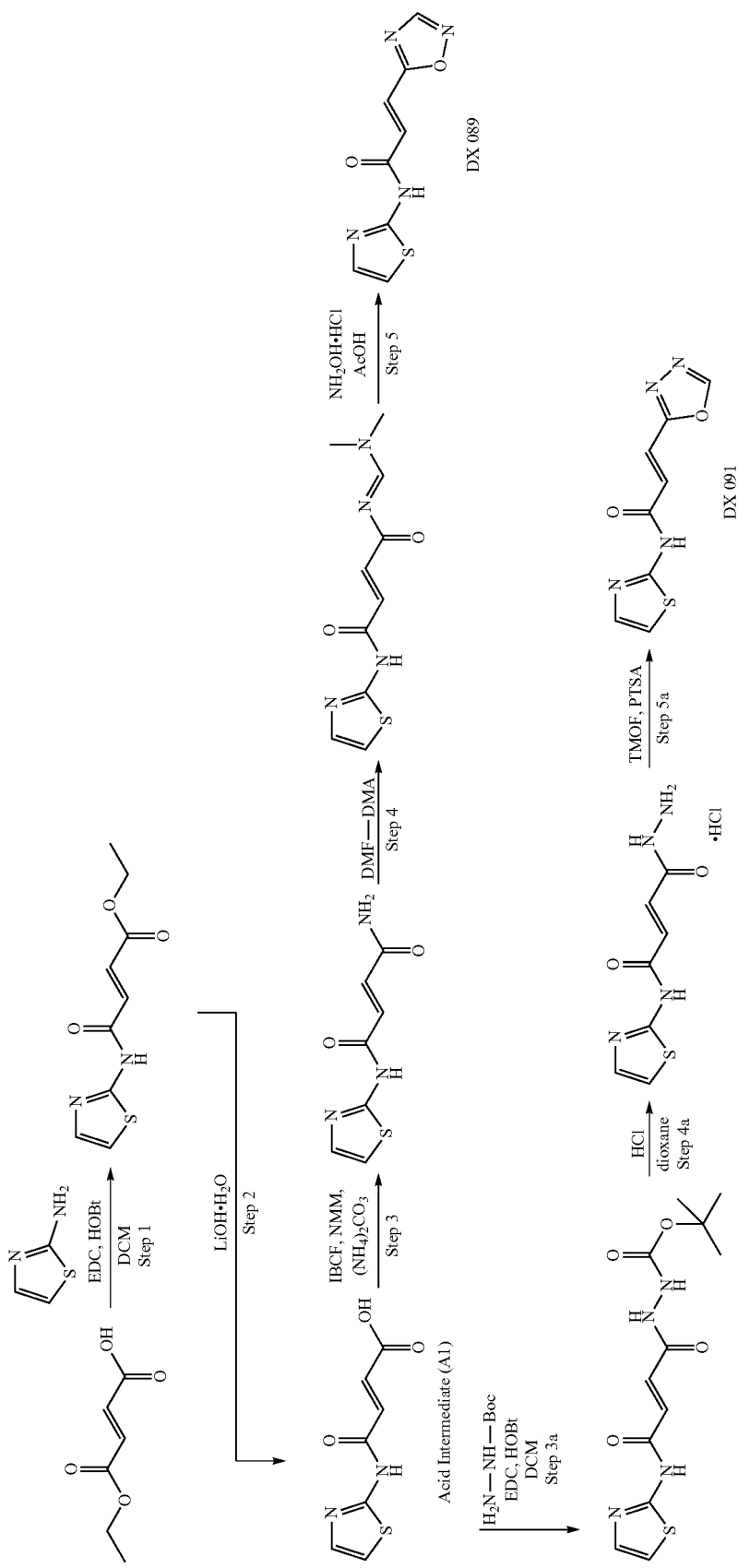

Step 4: (E)-N¹-(Dimethylamino)methylene-N⁴-(thiazol-2-yl)fumaramide. To a stirred solution of N¹-(thiazol-2-yl)fumaramide (300 mg, 1.52 mmol) in dry 1,4-dioxane (20 mL) was added DMF-DMA and heated at 80° C. for 2 h. The organic volatiles were evaporated in vacuo, and the crude solid was washed with Et₂O (2×20 mL) to afford (E)-N¹-(Dimethylamino)methylene-N⁴-(thiazol-2-yl)fumaramide as a brown solid (150 mg, 99%). R_f: 0.3 (10% MeOH/CHCl₃). ¹H NMR (d⁶ DMSO) –δ3.10 (s, 3H), δ 3.19 (s, 3H), δ6.92-6.96 (d, 1H), δ7.26-7.30 (d, 1H), δ7.30-7.31 (d, 1H), δ7.53-7.54 (d, 1H), δ8.54 (s, br, 1H), δ12.59 (s, br, 1H)

Step 5: (E)-3-(1,2,4-Oxadiazol-5-yl)-N-(thiazol-2-yl)acrylamide (I_HSF 089, identified as DX 089 in the above scheme). To a stirred solution of hydroxylamine hydrochloride (50 mg, 0.72 mmol) in 5 M aq. NaOH (0.15 mL, 0.72 mmol) and acetic acid (1.5 mL) in 1,4 dioxane was added N¹-(Dimethylamino)methylene-N⁴-(thiazol-2-yl)fumaramide (150 mg, 0.60 mmol). The reaction mixture was heated to 90° C. for 16 h. The reaction mixture was cooled to ambient temperature and suspended in water (50 mL) and extracted with EtOAc (2×50 mL). The organic layer was washed with brine (50 mL), dried over Na₂SO₄ and concentrated in vacuo. The crude compound was purified by column chromatography (silica gel, 100-200 mesh, 40% EtOAc/pet. ether) to obtain I_HSF 089 as a yellow solid (25 mg, 19%). R_f: 0.7 (10% MeOH/CHCl₃). Method_2 TFA_UPLC_2; Rt 1.74 min (94%); m/z 223 (MH⁺); ¹H NMR (d⁶ DMSO) δ7.35-7.36 (d, 1H), δ7.47-7.51 (d, 1H, J=15.8 Hz), δ7.57-7.58 (d, 1H), δ7.58-7.62 (d, 1H, J=15.8 Hz), δ9.16 (s, 1H), δ12.81 (s, br, 1H).

Synthesis of Final Compound I_HSF 091 Via Acid Intermediate A1:

Step 3a: (E)-tert-Butyl-2-(4-oxo-4-(thiazol-2-ylamino)but-2-enoyl)hydrazinecarboxylate. To a stirred suspension of (E)-4-oxo-4-(thiazol-2-ylamino)but-2-enoic acid (A1) (500 mg, 2.52 mmol) in DCM (50 mL) at 0° C. was added sequentially, DIPEA (0.62 mL, 3.53 mmol), EDC (540 mg, 2.83 mmol), HOBt (390 mg, 2.83 mmol) and Boc-hydrazine (340 mg, 2.59 mmol), and the reaction mixture was stirred at ambient temperature for 16 h. The reaction mixture was diluted with water (50 mL), extracted with DCM (2×200 mL), the organic layer was washed with brine (50 mL), dried over Na₂SO₄ and concentrated in vacuo. The crude compound was purified by column chromatography (silica gel, 100-200 mesh, 60% EtOAc/pet ether) to obtain (E)-tert-butyl-2-(4-oxo-4-(thiazol-2-ylamino)but-2-enoyl)hydrazinecarboxylate as a white solid (200 mg, 26%). R_f: 0.6 (10% MeOH/CHCl₃). ¹H NMR (d⁶ DMSO) δ1.42 (s, 9H), δ7.02-7.06 (d, 1H), δ7.17-7.21 (d, 1H), δ7.31-7.32 (d, 1H), δ7.54-7.56 (d, 1H), δ9.04 (s, br, 1H), δ10.23 (s, br, 1H), δ12.69 (s, br, 1H); MS (APCI) m/z 313 (MH⁺).

Step 4a: (E)-4-Hydrazinyl-oxo-N-(thiazol-2-yl)but-2-enamide hydrochloride. To a stirred solution of (E)-tert-butyl-2-(4-oxo-4-(thiazol-2-ylamino)but-2-enoyl)hydrazinecarboxylate (200 mg, 0.64 mmol) in dry 1, 4-dioxane (20 mL), cooled to 0° C. was added slowly HCl in dioxane (5 mL), and the reaction was allowed to stir at ambient temperature for 16 h. The organic volatiles were evaporated in vacuo, and the precipitated solid was washed with Et₂O (2×20 mL) to give (E)-4-hydrazinyl-oxo-N-(thiazol-2-yl)but-2-enamide hydrochloride as a white solid (150 mg, 99% crude yield). R_f: 0.2 (10% MeOH/CHCl₃). ¹H NMR (d⁶ DMSO) δ7.10-7.13 (d, 1H), δ7.28-7.31 (d, 1H), δ7.34-7.35 (d, 1H), δ7.56-7.57 (d, 1H), δ11.74 (s, br, 1H), δ12.75 (s, br, 1H) some exchangeable protons not visible; MS (APCI) m/z 213 (MH⁺).

Step 5a: (E)-3-(1,3,4-Oxadiazol-2-yl)-N-(thiazol-2-yl)acrylamide (I_HSF 091, identified as DX 091 in the above scheme). To a solution of (E)-4-hydrazinyl-oxo-N-(thiazol-2-yl)but-2-enamide hydrochloride (200 mg, 0.81 mmol) in triethyl orthoformate (6 mL) was added PTSA (catalytic) and heated to 100° C. in a sealed tube for 16 h. The reaction mixture was cooled to ambient temperature, poured onto water (50 mL) and extracted with EtOAc (2×50 mL). The organic layer was washed with brine (50 mL), dried over Na₂SO₄ and concentrated in vacuo. The crude compound was purified by column chromatography (silica gel, 100-200 mesh, 75% EtOAc/pet. ether) to obtain compound (E)-3-(1,3,4-oxadiazol-2-yl)-N-(thiazol-2-yl)acrylamide, I_HSF 091 as a yellow solid (50 mg, 28%). R_f: 0.5 (10% MeOH/CHCl₃). AK4; Rt 1.09 min (96%); m/z 223 (MH⁺); ¹H NMR (d⁶ DMSO) δ7.28-7.32 (d, 1H, J=15.6 Hz), δ7.34-7.35 (d, 1H), δ7.56-7.60 (d, 1H, J=15.6 Hz), δ7.56-7.57 (d, 1H), δ9.38 (s, 1H), δ12.74 (s, br, 1H).

1.5 Final Compounds—Route H 1.5.1 Synthesis of Final Compound I_HSF 088 Via Route H

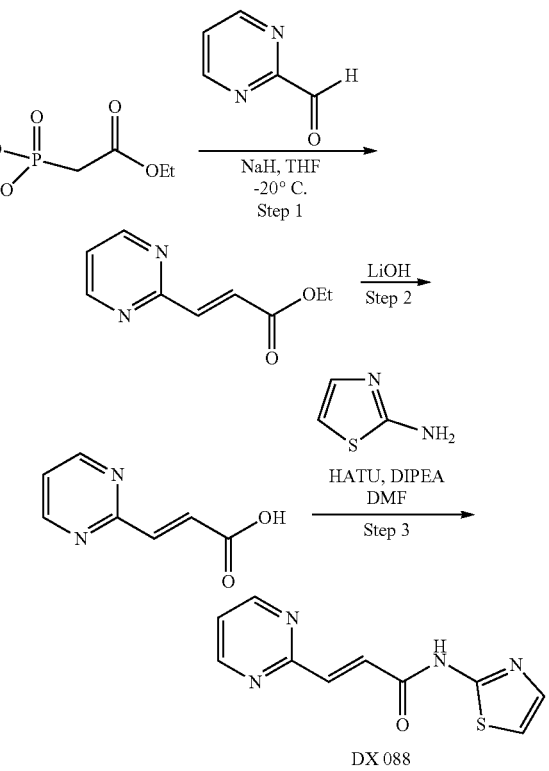

DX 088

Step 1: (E)-Ethyl 3-(pyrimidin-2-yl)acrylate. A pre-mixed solution of triethylphosphonoacetate (270 mg, 1.2 mmol) in THF (5 mL) was added to a suspension of NaH (40 mg, 1.01 mmol) in THF at −15° C. over a period of 10 min. The reaction was stirred at −15° C. for 30 min. To the reaction mixture was added a pre-mixed solution of pyrimidine-2-carbaldehyde (100 mg, 0.92 mmol) in THF (15 mL) at −20° C. over a period of 10 min. The reaction mixture was quenched with ice-cold water and extracted with EtOAc (2×20 mL). The combined organics were washed with water (2×10 mL), brine solution (2×10 mL), dried over Na₂SO₄ and concentrated in vacuo. The crude compound was purified by column chromatography (silica gel, 100-200 mesh, eluting with 10-20% EtOAc/pet. ether) to afford (E)-ethyl 3-(pyrimidin-2-yl)acrylate as a pale yellow liquid (60 mg, 36%). $R_f$: 0.6 (50% EtOAc/pet. ether). XTERRA; Rt 2.92 min (99%); m/z 179 (MH$^+$); $^1$H NMR (CDCl$_3$) δ1.33-1.37 (t, 3H), δ4.27-4.32 (q, 2H), δ7.17-7.27 (m, 2H), δ7.68-7.72 (d, 1H), δ8.77-8.79 (d, 2H).

Step 2: (E)-3-(Pyrimidin-2-yl)acrylic acid. To a stirred solution of (E)-ethyl 3-(pyrimidin-2-yl)acrylate (80 mg, 0.44 mmol) in THF (10 mL) was added an aqueous solution of LiOH.H$_2$O (75 mg, 1.79 mmol) at ambient temperature. After 3 h the reaction mixture was concentrated in vacuo, and the residue was extracted with EtOAc (10 mL). The combined organic layers were washed with brine (2×10 mL), dried over anhydrous Na$_2$SO$_4$ and concentrated in vacuo to afford (E)-3-(pyrimidin-2-yl)acrylic acid as an off-white solid (40 mg, 59%). $R_f$: 0.2 (70% EtOAc/pet. ether). $^1$H NMR (d$^6$-DMSO) δ6.98-7.02 (d, 1H), δ7.43-7.47 (d, 1H), δ7.49-7.51 (t, 1H), δ8.88-8.90 (d, 2H), δ12.88 (s, br, 1H).

Step 3: (E)-3-(Pyrimidin-2-yl)-N-(thiazol-2-yl)acrylamide (I$_{HSF}$ 088, identified as DX 088 in the above scheme). To a stirred suspension of (E)-3-(pyrimidin-2-yl)acrylic acid (50 mg, 0.32 mmol) in DMF (3 mL) was added DIPEA (0.1 mL, 0.64 mmol), HATU (187 mg, 0.49 mmol), and 2-aminothiazole (35 mg, 0.35 mmol) sequentially at 0° C. The reaction was slowly warmed to ambient temperature and stirred for 30 min. The reaction mixture was diluted with EtOAc and washed with water then brine, dried over anhydrous Na$_2$SO$_4$ and concentrated under reduced pressure to obtain crude product. The crude product was triturated with MeOH, filtered and washed with MeOH to afford (E)-3-(pyrimidin-2-yl)-N-(thiazol-2-yl)acrylamide, I$_{HSF}$ 088, as a yellow solid (18 mg, 24%). $R_f$: 0.3 (70% EtOAc/pet. ether). Method_2_TFA_UPLC_2; Rt 1.49 min (99%); m/z 233 (MH$^+$); $^1$H NMR (CD$_3$CO$_2$D) δ7.19-7.20 (d, 1H), δ7.49-7.53 (d, 1H,), δ7.5-7.52 (d, 2H), δ7.83-7.87 (d, 1H, J=14.95 Hz), δ9.00 (d, 1H), δ11.67 (s, br, 1H).

1.6 Final Compounds Route I

Synthesis of Final Compound I$_{HSF}$ 095 Via Route I

Step 1: N$^1$,N$^1$-Dimethyl-N$^4$-(thiazol-2-yl)fumaramide. To a stirred solution of 3-(thiazol-2-ylcarbamoyl)-acrylic acid (500 mg, 2.52 mmol) in dry THF at −40° C. was added NMM (306 mg, 3.03 mmol) and isobutyl chloroformate (413 mg, 3.03 mmol), and the solution was stirred for 20 min. N,O-dimethylhydroxylamine hydrochloride (154 mg, 2.52 mmol) was added to the reaction mixture which was allowed to warm to ambient temperature and was stirred for 2 h. The solvent was evaporated in vacuo, and the residue was diluted with water, extracted with EtOAc (2×100 mL) and the combined organics washed with water (2×100 mL), brine (2×100 mL), dried over Na$_2$SO$_4$ and concentrated in vacuo. The crude compound was purified by column chromatography (silica gel, 100-200 mesh, 60% EtOAc/pet. ether as eluent) to afford N$^1$,N$^1$dimethyl-N$^4$-(thiazol-2-yl) fumaramide as an off-white solid (250 mg, 41%). $R_f$: 0.2 (40% EtOH/pet. ether). $^1$H NMR (d$^6$-DMSO) δ3.2 (s, 3H), δ3.73 (s, 3H), δ7.15-7.19 (d, 1H), δ7.3-7.31 (d of d, 1H), δ7.41-7.44 (d, 1H), δ7.53-7.54 (d of d, 1H), δ12.68 (s, br, 1H).

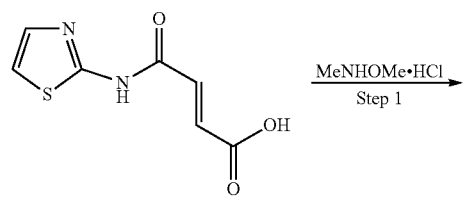

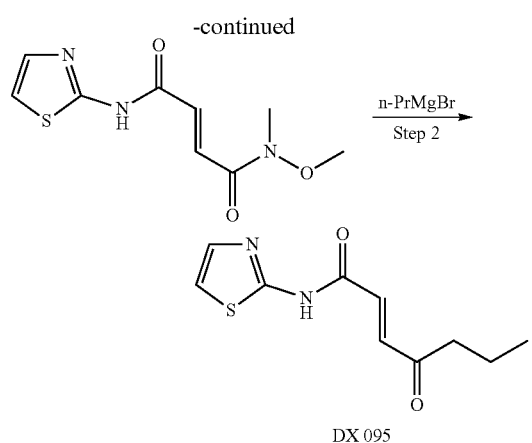

Step 2: (E)-4-Oxo-N-(thiazol-2-yl)hept-2-enamide (I$_{HSF}$ 095, identified as DX 095 in the above scheme). To a stirred solution of N$^1$,N$^1$-dimethyl-N$^4$-(thiazol-2-yl)fumaramide (150 mg, 0.63 mmol) in dry THF, cooled to 0° C., was added slowly a freshly prepared solution of n-propylmagnesium bromide (37 mg, 1.55 mmol). The reaction was stirred at 0° C. for 2 h. The reaction mixture was quenched with sat. aq. NH$_4$Cl solution, the solvent was evaporated in vacuo, and the residue was diluted with water and extracted with EtOAc (2×100 mL). The combined organics were washed with water (2×100 mL), brine (2×100 mL), dried over Na$_2$SO$_4$ and concentrated in vacuo. The crude compound was purified by column chromatography (silica gel, 100-200 mesh, 18% EtOAc/pet. ether) to afford (E)-4-oxo-N-(thiazol-2-yl)hept-2-enamide, I$_{HSF}$ 095, as a white solid (25 mg, 18%). $R_f$: 0.6 (30% EtOH/pet. ether). LCMS-2; Rt 1.32 min (97%); m/z 225 (MH$^+$); $^1$H NMR (CDCl$_3$) δ0.96-1.00 (t, 3H), δ1.68-1.77 (m, 2H), δ2.65-2.68 (t, 2H), δ7.09-7.13 (d, 1H, J=15.8 Hz), δ7.12-7.13 (d, 1H), δ7.33-7.37 (d, 1H, J=15.82 Hz), δ7.67-7.68 (d, 1H), δ12.24 (s, br, 1H).

Example 2: Pharmaceutical Compositions for Parenteral Administration 2.1 Formulation of I$_{HSF}$ 115 in Kleptose HPB

TABLE 14

| IHSF 115 in aqueous Kleptose HPB | |
|---|---|
| Component | Amount |
| I$_{HSF}$ 115 | 85 mg |
| Kleptose HPB | 3.035 g |
| Water | 8.5 g |

Preparation of a Parenteral Formulation for Use in the Experiments Described Under Example 3:

1. Prepare 15 ml of a 357 mg/ml stock solution of Kleptose HPB (Roquette Pharma) in water (of which the amount not used under 2 is reserved for vehicle controls).

2. Dissolve 85 mg of compound 0115 in 8.5 ml of Kleptose stock solution by incubating the solution overnight with slow agitation (at room temperature). Over 90% of the drug substance will be dissolved after this incubation.

3. Vortex briefly and sterile-filter the solution of step 2 through MillexR-GV, Syringe Driven Filter Unit (cat. No. SLGV 004 SL, Milipore).

4. For 2 mg and 1 mg doses, dose undiluted at 200 μL, and 100 μL, respectively.

2.2 Suspension formulations of $I_{HSF}$ 115
2.2.1 Formulation with Solutol HS15 and Lecithin

TABLE 15

Formulation with Solutol HS15 and Lecithin

| Component | Amount/volume |
|---|---|
| $I_{HSF}$ 115 | 25 mg |
| Solutol HS15 (1 g/ml in water)* | 37.5 µl |
| Phosphatidylcholine (0.25 g/ml water)* | 400 µl |
| Water | 537.5 µl |

*Chemicals obtained from Sigma-Aldrich

Preparation of a Parenteral Formulation for Use in the Experiments Described Under Example 4:
1. Mix solvents (Solutol HS15, phosphatidylcholine and water).
2. Autoclave and add water to compensate for losses, if any.
2. Use the autoclaved solvent mixture to dissolve $I_{HSF}$ 115 (sterilized by β-irradiation (25 kGy)) by stirring the complete mixture at 60° C. for approximately 10 min.

2.2.2 Formulation with Cremophor EL and Lecithin

TABLE 16

Formulation with Cremophor EL and Lecithin

| Component | Amount/volume |
|---|---|
| $I_{HSF}$ 115 | 25 mg |
| Cremophor EL (1 g/ml in water)* | 25 µl |
| Phosphatidylcholine (0.25 g/ml water)* | 400 µl |
| Water | 270 µl |
| Glucose 5% | 280 µl |

*Chemicals obtained from Sigma-Aldrich

Preparation of a Parenteral Formulation:
1. Mix solvents (Cremophor EL, phosphatidylcholine, glucose and water).
2. Autoclave and add water to compensate for losses, if any.
2. Use the autoclaved solvent mixture to dissolve $I_{HSF}$ 115 (sterilized by β-irradiation (25 kGy)) by stirring the complete mixture at 60° C. for approximately 10 min.

Example 3: Anti-Tumor Activity of $I_{HSF}$ 115 as a Single Agent in a Human Prostate Cancer Xenograft Model Prostate cancer cell line PC-3 was obtained from ATTC and grown in tissue culture under standard conditions. Groups (8 animals) of athymic mice (6-7 weeks old, male, obtained from Harlan) were inoculated subcutaneously on the right flank with $5 \times 10^6$ PC-3 cells. Cells were administered as a 1:1 mixture of cells in medium and Matrigel. Treatment was initiated when tumor size reached about 200 mg, at which time the mice were randomized. Of the various groups in the experiment, one group received a daily intravenous dose (via the tail vein) of 2 mg $I_{HSF}$ 115 in an aqueous solution of Kleptose HPB (see Example 2.1) for 7 days, followed by additional dosing with 2 mg $I_{HSF}$ 115 every other day. Another group received a daily dose of 0.8 mg $I_{HSF}$ 115 in an aqueous solution of Kleptose HPB (see Example 2.1) for 7 days, followed by additional dosing with 0.8 mg $I_{HSF}$ 115 every other day. A control group was subjected to same regimen, administering vehicle (Kleptose HPB solution) only. Tumor size and weight were assessed periodically and recorded. Tumor size was estimated using calipers. Calculation: tumor weight (mg)=$(a \times b^2/2)$ where 'b' is the smallest diameter and 'a' is the largest diameter. The results for the period of daily administration are shown in FIG. 9. Daily administration of 2 mg $I_{HSF}$ 115 resulted in a substantial (and statistically significant) reduction in tumor growth. The 0.8 mg dose had a smaller effect. Loss of weight for the period was less than 4%. No toxicity was observed, except for some local swelling in the inoculation region.

The invention claimed is:

1. An HSF inhibitor, wherein the inhibitor is an acrylamide derivative of (a) formula (II)

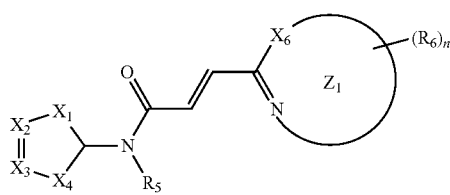

(II)

or a salt thereof, wherein $Z_1$ is a 5-8 membered, non-aromatic heterocycle, n is 0-8 (or 0-6 if Z1 is a 5-membered heterocycle);

$X_1$ is N or C(—$R_1$);

$X_2$ is C(—$R_2$), N, or S or O (double bond between $X_3$ and $X_4$ instead of between $X_2$ and $X_3$);

$X_3$ is C(—R) or N;

$X_4$ is S or O, or C(—$R_4$) or N if $X_2$ is O or S (double bond between $X_3$ and $X_4$ instead of between $X_2$ and $X_3$), $X_6$ is O, S, N, NH, ($C_1$-$C_4$)alkylN, CH or C(($C_1$-$C_4$)alkyl), $CH_2$ or CH(($C_1$-$C_4$)alkyl);

$R_1$ is H, halo, ($C_1$-$C_4$)alkyl or halo($C_1$-$C_4$)alkyl;

$R_2$, $R_3$, $R_5$ and $R_8$ are independently selected, and each can be H or any substituent, provided that its presence is compatible with the small molecule nature of the inhibitor and, statistically, no more than 10% of any ionizable group it may contain is ionized at neutral pH; whereby $R_2$ and $R_3$ can form a substituted or unsubstituted 5 to 8 membered aromatic or non-aromatic ring or heterocycle including $X_2$ and $X_3$;

$R_4$ is H, halo, ($C_1$-$C_4$)alkyl or halo($C_1$-$C_4$)alkyl, (b) formula (V),

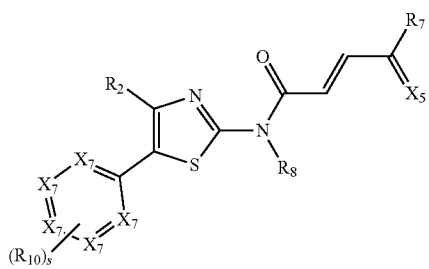

(V)

or a salt thereof, whereby $R_2$ and $R_5$ are independently selected, and each can be any substituent, provided that its presence is compatible with the small molecule nature of the inhibitor and, statistically, no more than 10% of any ionizable group it may contain is ionized at neutral pH; $X_5$ is O, S or N(—$R_6$); $R_6$ is H or is selected from halogen, OH, SH, $NH_2$ and $Z_2$ whereby $Z_2$ is a residue comprising from 1 to 4 carbon atoms; $R_7$ is —O—$Z_2$, —S—$Z_2$, —NH—$Z_2$ or —N—($Z_2$)$_2$; $X_7$ is CH or N (with 3 or less of the $X_7$ being N); $R_{10}$ is defined as $R_5$; and s is 0, 1, 2, 3 or 4, with the proviso that the inhibitor in which both $R_2$ and $R_5$ are H, s is 0, $R_7$ is ethoxy, $X_5$ is O and all $X_7$ are CH is excluded, (c) formula (IX)

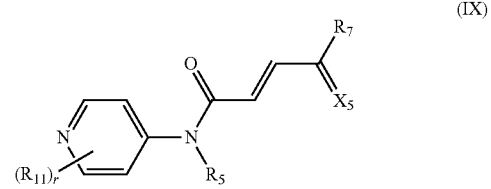

(IX)

or a salt thereof, whereby $R_5$ can be any substituent, provided that its presence is compatible with the small molecule nature of the inhibitor and, statistically, no more than 10% of any ionizable group it may contain is ionized at neutral pH; $X_5$ is O, S or N(—$R_6$); $R_6$ is H or is selected from halogen, OH, SH, $NH_2$ and $Z_2$ whereby $Z_2$ is a residue comprising from 1 to 4 carbon atoms; $R_7$ is —O—$Z_2$, —S—$Z_2$, —NH—$Z_2$ or —N—($Z_2$)$_2$; r is 0-4 and $R_{11}$ is defined as $R_5$, with the proviso that, if r is 0, $R_5$, $R_7$ and $X_5$ cannot be simultaneously H, methoxy and O, respectively, or (d) formula (X)

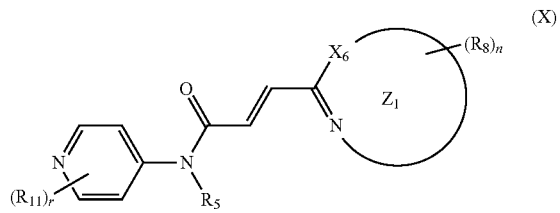

(X)

or a salt thereof, whereby Z1 is a 5-8 membered, non-aromatic heterocycle; n is 0-8 (or 0-6 if Z1 is a 5-membered heterocycle); $X_6$ is O, S, N, NH, ($C_1$-$C_4$) alkylN, CH or C(($C_1$-$C_4$)alkyl), $CH_2$ or CH(($C_1$-$C_4$) alkyl), $R_5$ and $R_8$ are independently selected, and each can be any substituent, provided that its presence is compatible with the small molecule nature of the inhibitor and, statistically, no more than 10% of any ionizable group it may contain is ionized at neutral pH; r is 0-4 and $R_{11}$ is defined as $R_5$.

2. The HSF inhibitor of claim 1, wherein the inhibitor is a compound of formula (IV) or a salt thereof, whereby n, $R_2$, $R_3$, $R_5$, $R_8$, $X_6$ and $Z_1$ are as defined in claim 1

(a) formula (I)

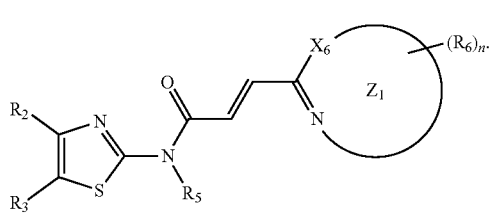
(IV)

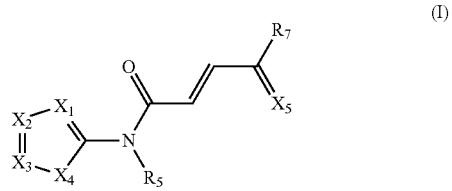
(I)

or a salt thereof, whereby $X_1$, $X_2$, $X_3$, $X_4$, $X_5$, $R_5$ and $R_7$ are defined as in claim 1,
(b) formula (II)

3. The HSF inhibitor of claim 1, wherein the inhibitor is a compound of formula (VI) or a salt thereof, whereby n, s, $R_2$, $R_5$, $R_8$, $R_{10}$, $X_6$, $X_7$ and $Z_1$ are as defined in claim 1.

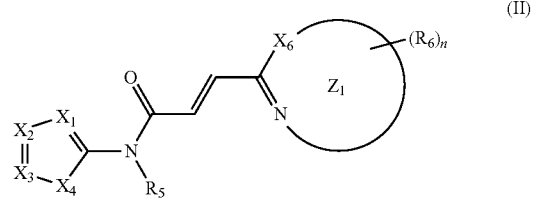
(II)

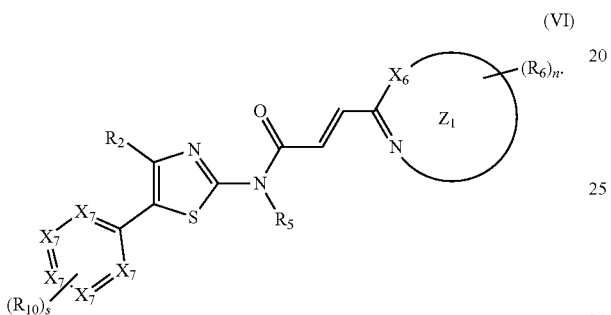
(VI)

or a salt thereof wherein $Z_1$, n, $X_1$, $X_2$, $X_3$, $X_4$, $X_6$, $R_5$ and $R_8$ are defined as in claim 1,
(c) formula (IX)

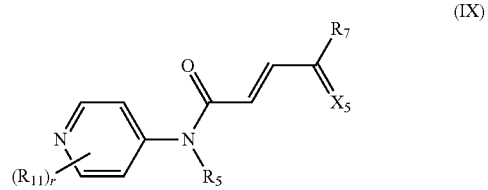
(IX)

4. The HSF inhibitor of claim 1, wherein the inhibitor is a compound of formula (VIII) or a salt thereof, whereby n, s, $R_2$, $R_5$, $R_8$, $R_{10}$, $X_6$, $X_7$ and $Z_1$ are as defined in claim 1.

or a salt thereof, whereby r, $R_5$, $R_7$, $R_{11}$ and $X_5$ are defined as in claim 1, or
(d) formula (X)

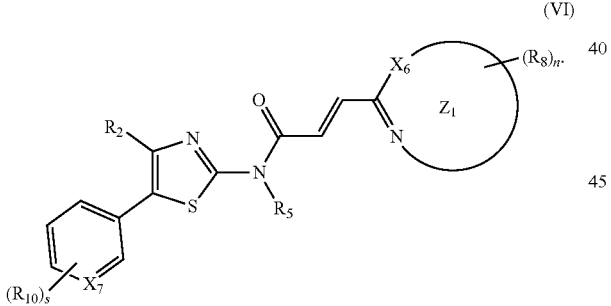
(VI)

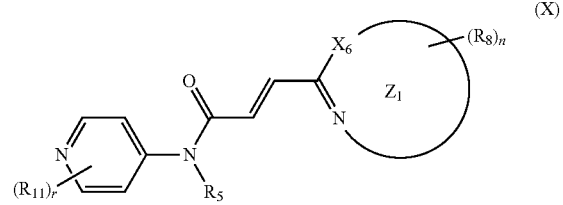
(X)

5. The HSF inhibitor of claim 1, wherein the inhibitor is (E)-3-(5,6-dihydro-4H-[1,3]oxazin-2-yl)-N-methyl-N-(5-(pyridin-3-yl-thiazol-2-yl)acrylamide or a salt thereof.

6. A pharmaceutical composition comprising an effective amount of an HSF inhibitor or a pharmaceutically acceptable salt or prodrug thereof and one or more pharmaceutically acceptable carriers or excipients, wherein the HSF inhibitor is a compound of or a salt thereof, whereby $Z_1$, n, r, $R_5$, $R_8$, $R_{11}$ and $X_6$ are defined as in claim 1.

7. The HSF inhibitor of claim 1, wherein the inhibitor is E-3-(5-Pyridin-3-yl-thiazol-2-yl carbamoyl)-acrylic acid ethyl ester or a salt thereof.

* * * * *

SEQUENCE LISTING

<160> NUMBER OF SEQ ID NOS: 1

<210> SEQ ID NO 1
<211> LENGTH: 529
<212> TYPE: PRT
<213> ORGANISM: HOMO SAPIENS

<400> SEQUENCE: 1

Met Asp Leu Pro Val Gly Pro Gly Ala Ala Gly Pro Ser Asn Val Pro
1               5                   10                  15

Ala Phe Leu Thr Lys Leu Trp Thr Leu Val Ser Asp Pro Asp Thr Asp
            20                  25                  30

Ala Leu Ile Cys Trp Ser Pro Ser Gly Asn Ser Phe His Val Phe Asp
        35                  40                  45

Gln Gly Gln Phe Ala Lys Glu Val Leu Pro Lys Tyr Phe Lys His Asn
    50                  55                  60

Asn Met Ala Ser Phe Val Arg Gln Leu Asn Met Tyr Gly Phe Arg Lys
65                  70                  75                  80

Val Val His Ile Glu Gln Gly Gly Leu Val Lys Pro Glu Arg Asp Asp
                85                  90                  95

Thr Glu Phe Gln His Pro Cys Phe Leu Arg Gly Gln Glu Gln Leu Leu
            100                 105                 110

```
Glu Asn Ile Lys Arg Lys Val Thr Ser Val Ser Thr Leu Lys Ser Glu
            115                 120                 125
Asp Ile Lys Ile Arg Gln Asp Ser Val Thr Lys Leu Leu Thr Asp Val
        130                 135                 140
Gln Leu Met Lys Gly Lys Gln Glu Cys Met Asp Ser Lys Leu Leu Ala
145                 150                 155                 160
Met Lys His Glu Asn Glu Ala Leu Trp Arg Glu Val Ala Ser Leu Arg
                165                 170                 175
Gln Lys His Ala Gln Gln Lys Val Val Asn Lys Leu Ile Gln Phe
            180                 185                 190
Leu Ile Ser Leu Val Gln Ser Asn Arg Ile Leu Gly Val Lys Arg Lys
            195                 200                 205
Ile Pro Leu Met Leu Asn Asp Ser Gly Ser Ala His Ser Met Pro Lys
        210                 215                 220
Tyr Ser Arg Gln Phe Ser Leu Glu His Val His Gly Ser Gly Pro Tyr
225                 230                 235                 240
Ser Ala Pro Ser Pro Ala Tyr Ser Ser Ser Leu Tyr Ala Pro Asp
                245                 250                 255
Ala Val Ala Ser Ser Gly Pro Ile Ile Ser Asp Ile Thr Glu Leu Ala
            260                 265                 270
Pro Ala Ser Pro Met Ala Ser Pro Gly Gly Ser Ile Asp Glu Arg Pro
        275                 280                 285
Leu Ser Ser Ser Pro Leu Val Arg Val Lys Glu Glu Pro Pro Ser Pro
290                 295                 300
Pro Gln Ser Pro Arg Val Glu Glu Ala Ser Pro Gly Arg Pro Ser Ser
305                 310                 315                 320
Val Asp Thr Leu Leu Ser Pro Thr Ala Leu Ile Asp Ser Ile Leu Arg
                325                 330                 335
Glu Ser Glu Pro Ala Pro Ala Ser Val Thr Ala Leu Thr Asp Ala Arg
            340                 345                 350
Gly His Thr Asp Thr Glu Gly Arg Pro Pro Ser Pro Pro Thr Ser
            355                 360                 365
Thr Pro Glu Lys Cys Leu Ser Val Ala Cys Leu Asp Lys Asn Glu Leu
370                 375                 380
Ser Asp His Leu Asp Ala Met Asp Ser Asn Leu Asp Asn Leu Gln Thr
385                 390                 395                 400
Met Leu Ser Ser His Gly Phe Ser Val Asp Thr Ser Ala Leu Leu Asp
                405                 410                 415
Leu Phe Ser Pro Ser Val Thr Val Pro Asp Met Ser Leu Pro Asp Leu
            420                 425                 430
Asp Ser Ser Leu Ala Ser Ile Gln Glu Leu Leu Ser Pro Gln Glu Pro
        435                 440                 445
Pro Arg Pro Pro Glu Ala Glu Asn Ser Ser Pro Asp Ser Gly Lys Gln
        450                 455                 460
Leu Val His Tyr Thr Ala Gln Pro Leu Phe Leu Leu Asp Pro Gly Ser
465                 470                 475                 480
Val Asp Thr Gly Ser Asn Asp Leu Pro Val Leu Phe Glu Leu Gly Glu
                485                 490                 495
Gly Ser Tyr Phe Ser Glu Gly Asp Gly Phe Ala Glu Asp Pro Thr Ile
            500                 505                 510
```

Ser Leu Leu Thr Gly Ser Glu Pro Pro Lys Ala Lys Asp Pro Thr Val
            515                 520                 525
Ser